United States Patent

Okeda et al.

[11] Patent Number: 6,043,380
[45] Date of Patent: Mar. 28, 2000

[54] RUTHENIUM-IODO-OPTICALLY ACTIVE PHOSPHINE COMPLEX

[75] Inventors: Yoshiki Okeda; Tsutomu Hashimoto; Yoji Hori; Toshimitsu Hagiwara, all of Kanagawa, Japan

[73] Assignee: Takasago International Corporation, Tokyo, Japan

[21] Appl. No.: 09/307,750

[22] Filed: May 10, 1999

[30] Foreign Application Priority Data

May 8, 1998 [JP] Japan ..................... 10-142233
Mar. 31, 1999 [JP] Japan ..................... 11-093644

[51] Int. Cl.[7] ................. C07F 9/02; C07F 15/00; C07D 305/00
[52] U.S. Cl. .............. 549/206; 549/263; 556/18; 556/21; 556/136; 502/162
[58] Field of Search ............... 556/18, 21, 136; 549/206, 263

[56] References Cited

U.S. PATENT DOCUMENTS 4,691,037 9/1987 Yoshikawa et al. ............ 556/18
5,306,834 4/1994 Takaya et al. ............ 549/263
5,412,109 5/1995 Takaya et al. ............ 549/263

Primary Examiner—Porfirio Nazario-Gonzalez
Attorney, Agent, or Firm—Sughrue, Mion, Zinn Macpeak & Seas, PLLC

[57] ABSTRACT

This invention is concerned with a ruthenium-iodo-optically active bidentate phosphine complex of the formula (I):

$$[Ru-(I)_q-(T^1)_n(SOL)_r(L)]_m(T^2)_p(I)_s \quad (I)$$

wherein $T^1$ represents a carboxylic acid anion, SOL represents a polar solvent, L represents an optically active bidentate phosphine ligand, $T^2$ represents an anion different from halogen atom anions and carboxylic acid anions, n denotes 0 or 1, r denotes 0, 3 or 4, m denotes 1 or 2, q denotes 0 or 1, or where m is 2, q may represent 1 or 1.5, p denotes 0 or 1, and s denotes 0, 1 or 2 is prepared. Said phosphine complex is usefull as an efficient catalyst for asymmetrically hydrogenating 4-methylene-2-oxetanone into optically active 4-methyl-2-oxetanone.

25 Claims, 10 Drawing Sheets

RUTHENIUM-IODO-OPTICALLY ACTIVE PHOSPHINE COMPLEX

BACKGROUND OF THE INVENTION

1. Field of the Invention

The present invention relates to a novel ruthenium-iodo-optically active phosphine complex and a method for the production thereof and a method for the production of an optically active 4-methyl-2-oxetanone by using the ruthenium-iodo-optically active phosphine complex, and, particularly, to the above ruthenium-iodo-optically active phosphine complex used as a catalyst for a variety of organic synthetic reactions, especially, an asymmetric hydrogenation reaction, to a method for the production of the ruthenium-iodo-optically active phosphine complex and to a method for the production of an optically active 4-methyl-2-oxetanone which is useful as intermediates, such as raw materials for polymers, raw materials for synthesizing medicines and liquid crystal materials, which are used in organic synthetic chemical industries.

2. Description of Background Information

Many transition metal complexes have been used as the catalyst for organic synthetic reactions. In particular, metal complexes of a ruthenium metal and tertiary phosphine are well-known as the catalyst for asymmetric hydrogenation reactions. As ruthenium-optically active phosphine complex having, as a ligand, an optically active tertiary phosphine such as 2,2'-bis(diphenylphosphino)-1,1'-binaphthyl (hereinafter abbreviated as "BINAP"), the following compounds are known:

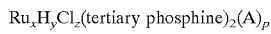

wherein A represents a tertiary amine; when y is 0, x denotes 2, z denotes 4 and p denotes 1; when y is 1, x denotes 1, z denotes 1 and p denotes 0 (Japanese Patent Publication (JP-B) Nos. H4-81596 and H5-12354);

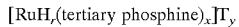

wherein T represents $ClO_4$, $BF_4$ or $PF_6$; when r is 0, x denotes 1 and y denotes 2; when r is 1, x denotes 2 and y denotes 1 (JP-B Nos. H5-12353 and H5-12355);

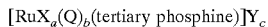

wherein X represents a halogen atom; Q represents a benzene which may have a substituent or an acetonitrile; Y represents a halogen atom, $ClO_4$, $PF_6$, BPh4 (where Ph represents a phenyl group, the same as follows) or $BF_4$; when Q is benzene which may have a substituent, a, b and c all represent 1; when Q is acetonitrile and a is 0, b denotes 4 and c denotes 2; when Q is acetonitrile and a is 1, b denotes 2 and c denotes 1. Incidentally, in the case where Q is p-cymene among benzene which may have a substituent and X and Y are iodine atoms, a, b and c all denote 1 or a, b and c may denote 1, 1 and 3 respectively (JP-B Nos. H7-57758 and H5-111639);

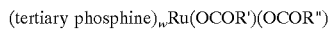

wherein R' and R" respectively represent a lower alkyl group, a halogenated lower alkyl group, a phenyl group which may have a lower alkyl substituent, α-aminoalkyl group or α-aminophenylalkyl group or R' and R" may be combined with each other to form an alkylene group, and w denotes 1 or 2 (JP-B Nos. H5-11119 and H5-12355);

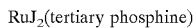

wherein J represents a chlorine atom, a bromine atom or an iodine atom (R. Noyori et al., J. Am. Chem. Soc., Vol. 109, No. 19, pp. 5856–5859 (1987)); and

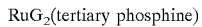

wherein G represents an aryl group or a methacryl group (J. P. Genet et al., Tetrahedron: Asymmetry, Vol. 2, No. 7, pp. 555–567 (1991)).

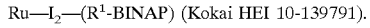

On the other hand, in JP-A No. H10-182678, a method for the production of SEGPHOS and ruthenium complexes containing this SEGPHOS as a ligand, specifically, [RuX(arene)(SEGPHOS)] (wherein X represents a halogen atom and arene represents a hydrocarbon having a benzene ring), $Ru_2X_4(SEGPHOS)_2NEt_3$ and Ru(methylallyl)2 (SEGPHOS) are shown. Also, $[Ru(BINAP)(CH_3CN)_4]_2^+X^-(Y^-)$ (wherein X represents a halogen atom and Y represents a halogen atom or $BF_4$), $[RuX(BINAP)(CH_3CN)_3]^+X^+$, $RuX_2(BINAP)(CH_3CN)_2$ and the like which are similar to the complex of the present invention are shown by K. Mashima et al; J. Chem. Soc. Dalton Trans., pp. 2099–2107 (1992).

However, even if these ruthenium-optically phosphine complexes are used, there is the case where such a problem that only an insufficient catalytic activity and asymmetric yield are obtained depending on the objective reaction or on a reaction substrate is posed in actual industrialization.

While, 4-methyl-2-oxetanone (which is also called "β-butyrolactone" or "β-methyl-β-propiolactone") has been used as raw materials for polymers or the like. Recently, the optically active materials of 4-methyl-2-oxetanone have been found to be useful and attracted considerable attention as described in Japanese Patent Application Laid-Open (JP-A) Nos. H6-256482, H6-329768, H7-53694, H8-53540 and H8-127645.

As the method for the production of optically active 4-methyl-2-oxetanone, the following methods are reported.

(a) A method in which 3-bromobutyric acid obtained by adding hydrobromic acid to crotonic acid is optically resolved using optically active naphthylethylamine and is then cyclized (J. Reid Shelton et al.; Polymer Letters, Vol. 9, pp. 173–178 (1971) and T. Sato et al; Tetrahedron Lett., Vol. 21, pp. 3377–3380 (1980)).

(b) A method in which triethylorthoacetic acid is reacted with optically active 3-hydroxybutyric acid to obtain optically active 2-ethoxy-2,6-dimethyl-1,3-dioxane-4-one, which is then heat-decomposed (A. Griesbeck et al.; Helv. Chim. Acta, Vol. 70, pp. 1320–1325 (1987) and R. Breitschuh et al.; Chimia, Vol. 44, pp. 216–218 (1990)).

(c) A method in which optically active 3-hydroxybutyric acid ester is reacted with methanesulfonyl chloride to mesylate a hydroxide group and the resulting ester is hydrolyzed, followed by condensation-cyclizing using sodium hydrogen carbonate (Y. Zhang et al.; Macromolecules, Vol. 23. pp. 3206–3212 (1990)).

Furthermore, the following method is reported as an instance using the aforementioned ruthenium-optically active phosphine complex.

(d) 4-Methylene-2-oxetanone (also called "diketene") is hydrogenated asymmetrically in an aprotic solvent such as a methylene chloride or tetrahydrofuran by using as a catalyst [RuCl[(S)— or (R)-BINAP (benzene)]Cl or [Ru$_2$Cl$_4$[(S)— or (R)-BINAP]$_2$(NEt$_3$) wherein Et represents an ethyl group (T. Ohta et al.; J. Chem. Soc., Chem. Commun., 1725 (1992)).

These methods however have the following problems. Specifically, in the method (a), a specific optically active amine is required as an optically resolving agent in an amount by mol equivalent to the raw material compound and unnecessary enantiomers are by-produced in an amount equivalent to the objective product. This method therefore involves much usefulness and is hence economically disadvantageous. In the methods (b) and (c), it is not easy to synthesize the raw material compound, specifically, optically active 3-hydroxybutyric acid or its ester. To mention in detail, it is necessary to heat-decompose optically active poly-3-hydroxybutyric acid ester produced by microorganisms or to form acetoacetic acid ester from 4-methylene-2-oxetanone by an alcoholysis reaction followed by asymmetric reduction. This method therefore involves many steps and is complicated. The method (d) succeeds in solving the aforementioned problems involved in the methods (a) to (c) but involves some problems; it has a low catalytic activity and requires long reaction time. Moreover, the optical purity of the resulting product produced in this method is as low as 70–92% e.e. This method has been improved as reported in JP-A No. H6-128245, H7-188201 and H7-206885. However, this method is not an industrially satisfactory method on account of its low catalytic activity.

SUMMARY OF THE INVENTION

Accordingly, it is an object of the present invention to provide a catalyst which has a high catalytic activity and gives a high yield in an asymmetric reaction, specifically, produces a product of optically high purity and also to provide a method for producing optically active 4-methyl-2-oxetanone, which has optically high purity and is useful as the raw materials of polymers and the like, in a short time in an efficient manner by using the catalyst.

The inventors of the present invention have conducted earnest studies to solve the above problems and, as a result, found that a novel ruthenium-iodo-optically active phosphine complex which can be obtained by a relatively simple method has a remarkably high catalytic activity and can be widely used as an asymmetrically synthesizing catalyst and that when it is used as a catalyst for the asymmetric hydrogenation reaction of 4-methylene-2-oxetanone, optically active 4-methyl-2-oxetanone of optically high purity can be produced in a short time in an efficient manner, to complete the present invention.

As a first aspect of the invention, there is provided a ruthenium-iodo-optically active bidentate phosphine complex of the formula (1):

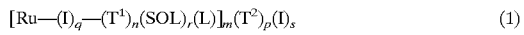
(1)

wherein T$^1$ represents a carboxylic acid anion, SOL represents a polar solvent, L represents an optically active bidentate phosphine ligand, T$^2$ represents an anion different from halogen atom anions and carboxylic acid anions, n denotes 0 or 1, r denotes 0, 3 or 4, m denotes 1 or 2, q denotes 0 or 1, or where m is 2, q may represents 1 or 1.5, p denotes 0 or 1, and s denotes 0, 1 or 2.

In the above formula, r and s each may be 0, whilst q may be 1, or where m is 2, 1 or 1.5; the ruthenium-iodo-optically active bidentate phosphine complex thus having the formula (1a):

(1a)

Further, L may be of the formula (2):

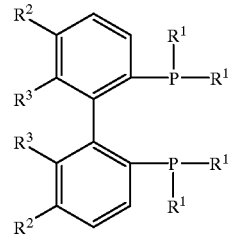
(2)

wherein R$^1$ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms; and R$^2$ and R$^3$, which may be the same or different, each represent a hydrogen atom, a halogen atom, a lower alkyl group having 1 to 4 carbon atoms or a lower alkoxy group having 1 to 4 carbon atoms; or R$^2$ and R$^3$ may be combined to form a five-membered or six-membered ring.

There is also provided a method of preparing the ruthenium-iodo-optically active bidentate phosphine complex. The method comprises reacting, in a polar solvent different from nitrile-type solvents, a ruthenium-iodo-optically active phosphine complex of the formula (3):

(3)

wherein arene represents a hydrocarbon having a benzene ring and L represents an optically active bidentate phosphine ligand, either with (i) a carboxylate of the formula (4):

(4)

wherein Z$^1$ represents an alkali metal or an alkali earth metal, a denotes 1 when Z$^1$ is an alkali metal, or 2 when Z$^1$ is an alkali earth metal, and T$^1$ has the same meaning as that defined in the formula (1); or with (ii) a salt of the formula (5):

(5)

wherein Z$^2$ represents a mono- or di-cation of an alkali metal, an alkali earth metal, an ammonium or the like, T$^2$ represents a mono- or di-anion different from halogen atom anions and carboxylic acid anions, in which when Z$^2$ is a mono-cation and T is a mono-anion, b and c are each 1; when Z$^2$ is a mono-cation and T$^2$ is a di-anion, b and c denote 2 and 1, respectively; when Z$^2$ is a di-cation and T$^2$ is a di-anion, b and c are each 1, and when Z$^2$ is a di-cation and T$^2$ is a mono-anion, b and c denote 1 and 2, respectively.

The method may also comprise reacting, in a polar solvent different from nitrile-type solvents, a compound of formula (6):

(6)

wherein arene represents a hydrocarbon having a benzene ring, with an optically active bidentate phosphine ligand L and either with (i) a carboxylate of the formula (4):

(4)

wherein $Z^1$, a and $T^1$ have the same meaning as above; or with (ii) a salt of the formula (5):

$$Z^2{}_b(T^2)_c \quad (5)$$

wherein $Z^2$, b, $T^2$ and c have the same meaning as above.

The optically active bidentate phosphine ligand L may be a compound selected from the group consisting of an optically active tertiary phosphine ($R^1$-BINAP), in which $R^2$ and $R^3$ in the formula (2) are combined with each other to form a six-membered benzene ring and which is represented by the formula (7):

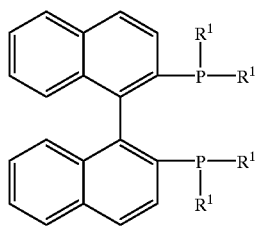

(7)

wherein $R^1$ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms;

an optically active tertiary phosphine ($H^8$—$R^1$-BINAP), in which $R^2$ and $R^3$ in the formula (2) are combined with each other to form a six-membered cyclohexyl ring and which is represented by the formula (8):

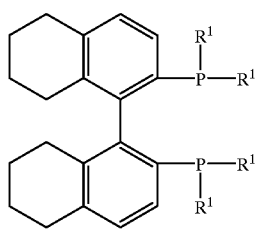

(8)

wherein $R^1$ is defined as indicated above in the formula (7), and;

an optically active tertiary phosphine ($R^1$-SEGPHOS), in which $R^2$ and $R^3$ in the formula (2) are combined with each other to form a five-membered 1,3-dioxolan ring and which is represented by the formula (9):

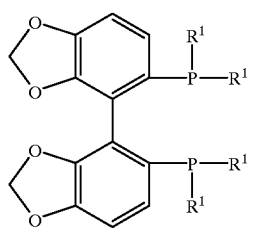

(9)

wherein $R^1$ is defined as indicated above in the formula (7).

In the above method, L in the formula (3) may represent $R^1$-BINAP as shown in the formula (10):

$$[RuI(arene)(R^1\text{-BINAP})]I \quad (10)$$

$R^1$-BINAP being defined in the formula (7).

Likewise, L in the formula (1) may represent $R^1$-BINAP as defined in the formula (7).

There is also provided a method of preparing the ruthenium-iodo-optically active bidentate phosphine complex, wherein the ruthenium-optically active phosphine complex of the formula (3), in which L represents $R^1$-SEGPHOS as shown in the formula (11):

$$[RuI(arene)(R^1\text{-SEGPHOS})]I \quad (11)$$

$R^1$-SEGPHOS being defined in the formula (9); is reacted with the salt of the formula (5).

Further, L in the formula (1) may represent $R^1$-SEGPHOS as defined in the formula (9), and the ruthenium complex and $R^1$-SEGPHOS may reacted with the salt of the formula (5).

As a second aspect of the invention, there is provided a ruthenium-iodo-optically active bidentate phosphine complex of formula (1)

$$[Ru-(I)_q-(T^1)_n(SOL)_r(L)_m(T^2)_p(I)_s \quad (1)$$

wherein; $T^1$ represents a carboxylic acid anion; SOL represents a polar solvent; L represents $R^1$-SEGPHOS as defined in the formula (IX); $T^2$ represents an anion different from halogen atom anions and carboxylic acid anions; n denotes 0; m denotes 1; p denotes 1; q denotes 0 or 1; r denotes 3 or 4; and s denotes 0, 1 or 2.

The above ruthenium-iodo-optically active bidentate phosphine complex may comprise three different complexes of formulae (12), (13) and (14):

$$[Ru(R^1\text{-SEGPHOS})(SOL)_4]I_2 \quad (12)$$

$$[Ru(R^1\text{-SEGPHOS})(SOL)_4]I(\text{anion}) \quad (13)$$

$$[RuI(R^1\text{-SEGPHOS})(SOL)_3](\text{anion}) \quad (14)$$

wherein $R^1$-SEGPHOS represents an optically active tertiary phosphine of the formula (9), SOL represents a nitrile-type polar solvent, and $T^2$ designated as anion represents a perfluoroalkylsulfonyl anion.

To this end, the ruthenium-iodo-optically active bidentate phosphine complex, wherein a ruthenium-optically active tertiary phosphine complex of the formula (11):

$$[RuI(arene)(R^1\text{-SEGPHOS})]I \quad (11)$$

wherein arene represents an hydrocarbon having a benzene ring and $R^1$-SEGPHOS has the same meaning as defined for the formula (9); may be reacted with a perfluoroalkylsulfonate of the formula (5), in a nitrile-type polar solvent.

Alternatively, a ruthenium complex of the formula (6), an optically active phosphine represented by $R^1$-SEGPHOS of the formula (9), and a perfluoroalkylsulfonate of the formula (5) may be reacted in a nitrile-type polar solvent.

There is further provided a process for preparing an optically active 4-methyl-2-oxetanone by asymmetrically hydrogenating 4-methylene-2-oxetanone in the presence of a ruthenium-iodo-optically active bidentate phosphine complex prepared as mentioned above.

Examples of ruthenium-iodo-optically active bidentate phosphine complex used for the above purpose include:

(i) a complex of the formula (1):

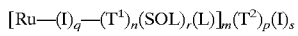

$$[\text{Ru}—(\text{I})_q—(\text{T}^1)_n(\text{SOL})_r(\text{L})]_m(\text{T}^2)_p(\text{I})_s \qquad (1)$$

wherein $T^1$ represents a carboxylic acid anion, SOL represents a polar solvent, L represents an optically active bidentate phosphine ligand, $T^2$ represents an anion different from halogen atom anions and carboxylic acid anions, n denotes 0 or 1, r denotes 0, 3 or 4, m denotes 1 or 2, q denotes 0 or 1, or where m is 2, q may represent 1 or 1.5, p denotes 0 or 1, and s denotes 0, 1 or 2;

(ii) a complex of the formula (1):

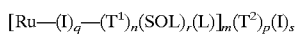

$$[\text{Ru}—(\text{I})_q—(\text{T}^1)_n(\text{SOL})_r(\text{L})]_m(\text{T}^2)_p(\text{I})_s \qquad (1)$$

wherein $T^1$ represents a carboxylic acid anion, SOL represents a polar solvent, L represents an optically active bidentate phosphine ligand, $T^2$ represents an anion different from halogen atom anions and carboxylic acid anions, n denotes 0 or 1, r denotes 0, m denotes 1 or 2, q denotes 1, or where m is 2, q may represent 1 or 1.5, p denotes 0 or 1, and s denotes 0, and wherein said optically active bidentate phosphine ligand L is a compound selected from the group consisting of an optically active tertiary phosphine ($R^1$-BINAP), in which $R^2$ and $R^3$ in said formula (2) are combined with each other to form a six-membered benzene ring and which is represented by the formula (7):

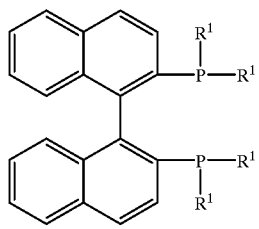

wherein $R^1$ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms;

an optically active tertiary phosphine ($H^8$—$R^1$-BINAP), in which $R^2$ and $R^3$ in said formula 2 are combined with each other to form a six-membered cyclohexyl ring and which is represented by the formula (8):

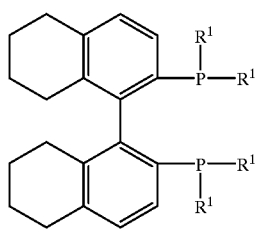

wherein $R^1$ is defined as indicated above in said formula (7), and;

an optically active tertiary phosphine ($R^1$-SEGPHOS), in which $R^2$ and $R^3$ in the formula (2) are combined with each other to form a five-membered 1,3-dioxolan ring and which is represented by the formula (9):

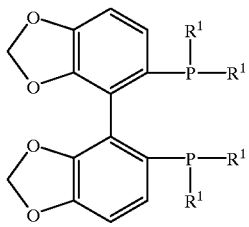

wherein $R^1$ is defined as indicated above in the formula (7); and, (iii) three different complexes of formulae (12), (13) and (14):

$$[\text{Ru}(R^1\text{-SEGPHOS})(\text{SOL})_4]\text{I}_2 \qquad (12)$$
$$[\text{Ru}(R^1\text{-SEGPHOS})(\text{SOL})_4]\text{I(anion)} \qquad (13)$$
$$[\text{RuI}(R^1\text{-SEGPHOS})(\text{SOL})_3](\text{anion}) \qquad (14)$$

wherein $R^1$-SEGPHOS represents an optically active tertiary phosphine of the formula (9), SOL represents a nitrile-type polar solvent, and $T^2$ designated as an anion represents a perfluoroalkylsulfonyl anion.

BRIEF DESCRIPTION OF THE DRAWINGS

The above and other objects, features and advantages of the present invention will be made apparent from the following description of the preferred embodiments, given as non-limiting examples, with reference to the accompanying drawings, in which.

DETAILED DESCRIPTION OF THE PREFERRED EMBODIMENTS

Figure 1:
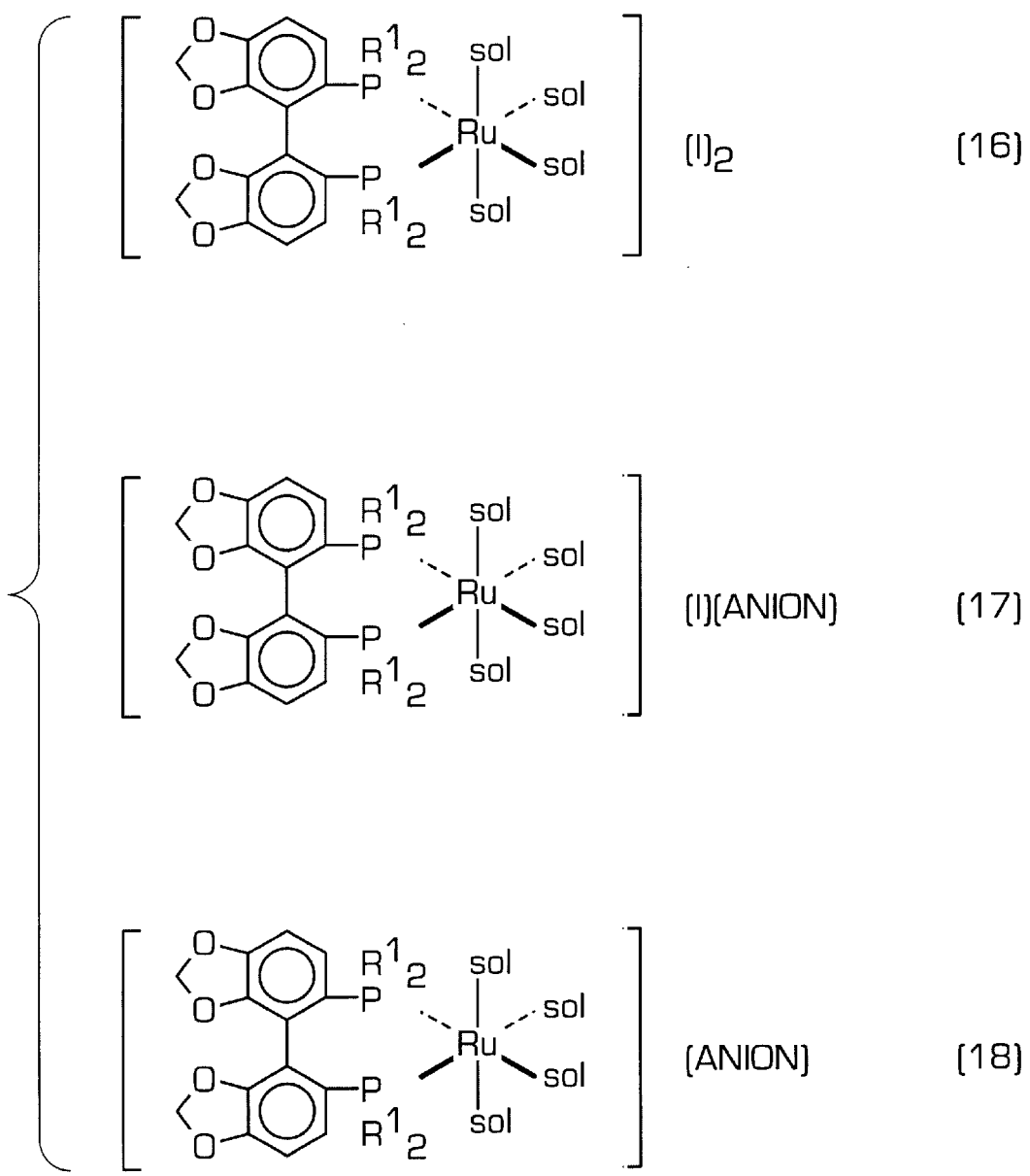
FIG. 1 shows the structures of $[\text{Ru}(R^1\text{-SEGPHOS})(\text{SOL})_4]\text{I}_2$, $[\text{Ru}(R^1\text{-SEGPHOS})(\text{SOL})_4]\text{I(anion)}$ and $[\text{RuI}(R^1\text{-SEGPHOS})(\text{SOL})_3](\text{anion})$ constituting a ruthenium-iodo-optically active phosphine complex mixture of the present invention.

As a first aspect of the invention, the ruthenium-iodo-optically active phosphine complex, hereinafter represented by [Ru—(I)$_q$—(T$^1$)$_n$(L)]$_m$(T$^2$)$_p$, can be produced by the following two methods. In one method, a ruthenium-optically phosphine complex [RuI(arene)(L)]I of the formula (3) is reacted with carboxylates (T$^1$)$_a$Z$^1$ of the formula (4) or with salts Z$^2_b$(T$^2$)$_c$ of the formula (5) in a polar solvent. In another method, a ruthenium complex [RuI$_2$(arene)]$_2$ of the formula (6) is reacted with an optically active bidentate phosphine ligand and carboxylates (T$^1$)$_a$Z$^1$ of the formula (4) or salts Z$^2_b$(T$^2$)$_c$ of the formula (5) in a polar solvent.

Specifically, the ruthenium complex [RuI(arene)(L)]I (formula (3)) and the carboxylates (T$^1$)$_a$Z$^1$ (formula (4)) or the salts Z$^2_b$(T$^2$)$_c$ (formula (5)) are placed in a reaction container in which air is replaced by an inert gas, e.g., nitrogen and heated with stirring in a polar solvent to react, followed by removing the polar solvent. The resulting product is then stirred in a two-layer solvent of methylene chloride/water at room temperature, followed by washing, to obtain the ruthenium-iodo-optically active phosphine complex. Alternatively, the ruthenium phosphine complex [RuI(arene)(L)]I (formula (3)) is heated with stirring in a polar solvent to react, followed by removing the polar solvent, to obtain an intermediate. To the intermediate are added the carboxylates (T$^1$)$_a$Z$^1$ (formula (4)) or the salts Z$^2_b$(T$^2$)$_c$ (formula (5)) and the mixture is stirred at room temperature in a two-layer solvent of methylene chloride/water to react, thereby obtaining the ruthenium-iodo-optically active phosphine complex.

Specifically, the ruthenium complex [RuI$_2$(arene)]$_2$ of the formula (6), the bidentate phosphine ligand (L), and the carboxylates (T$^1$)$_a$Z$^1$ (formula (4)) or the salts Z$^2_b$(T$^2$)$_c$ (formula (5)) are heated with stirring in a polar solvent to react, followed by removing the polar solvent. The resulting product is then stirred in a two-layer solvent of methylene chloride/water at room temperature to obtain the ruthenium-iodo-optically active phosphine complex. Alternatively, the ruthenium complex [RuI$_2$(arene)]$_2$ (6) and the bidentate phosphine ligand (L) are heated with stirring in a polar solvent to react, followed by removing the polar solvent, to obtain an intermediate. To the intermediate are added the carboxylates (T$^1$)$_a$Z$^1$ (formula (4)) or the salts Z$^2_b$(T$^2$)$_c$ (formula (5)) and the mixture is stirred at room temperature in a two-layer solvent of methylene chloride/water at room temperature to react, thereby obtaining the ruthenium-iodo-optically active phosphine complex.

As the optically active bidentate phosphine ligand represented by L in the ruthenium-optically active phosphine complex [RuI(arene)(L)]I (formula (3)) which is the raw material for the production of [Ru—(I)$_q$—(T1)$_n$(L)]$_m$(T$^2$)$_p$ of the present invention, optically active biphenyl tertiary phosphine (hereinafter called "BIPH" as the case may be) represented by the above-mentioned formula (2) is used.

Examples of BIPH include BIPHEP ((XXIII) described later) containing a phenyl group as R$^1$, a hydrogen atom as R$^2$ and a methyl group as R$^3$; BICHEP ((XXIV) described later) containing a cyclohexyl group as R$^1$, a hydrogen atom as R$^2$ and a methyl group as R$^3$; MBIPHEP ((XXV) described later) containing a phenyl group as R$^1$, a hydrogen atom as R$^2$ and a methoxy group as R$^3$; and MBICHEP ((XXVI) described later) containing a cyclohexyl group as R$^1$, a hydrogen atom as R$^2$ and a methoxy group as R$^3$.

Examples of the optically active biphenyl tertiary phosphine also include, other than the above BIPHEP and the like, (i) optically active tertiary phosphine (hereinafter called "R1-BINAP" as the case may be) represented by the above-mentioned formula (7), (ii) optically active tertiary phosphine (hereinafter called "H$^8$—R$^1$-BINAP" as the case may be) represented by the above-mentioned formula (8), and (iii) optically active tertiary phosphine represented by the above-mentioned formula (9):

Examples of the aryl group represented by R$^1$ in R$^1$-BINAP (formula (7)) include a phenyl group, 2-naphthyl group, phenyl groups having a substituent such as a p-substituted phenyl group, m-substituted phenyl group and m-diphenyl group and 2-naphthyl groups having a substituent such as 6-substituted-2-naphthyl group. Examples of the substituent which can be replaced by the phenyl group and the naphthyl group include a lower alkyl group (in which "lower" means a linear or branched chain having 1–4 carbon atoms, the same as follows) such as a methyl group and a tert-butyl group, lower alkoxy group, lower alkylamine group and halogen atom such as a chlorine atom. Cycloalkyl groups having 3 to 8 carbon atoms represented by R$^1$ are preferable and among these groups, a cyclopentyl group and cyclohexyl group are especially preferable.

As specific examples of the compounds represented by R$^1$-BINAP, the following compounds may be given. Incidentally, though all tertiary phosphines embrace an (R) isomer and an (S) isomer, the notation of these isomers is omitted (the same as follows).

(I) 2,2'-bis(diphenylphosphino)-1,1'-binaphthyl (hereinafter abbreviated simply as "BINAP")

(II) 2,2'-bis(di-p-tolylphosphino)-1,1'-binaphthyl (hereinafter abbreviated as "T-BINAP")

(III) 2,2'-bis(di-(p-tert-butylphenyl)phosphino)-1,1'-binaphthyl (hereinafter abbreviated as "tBu-BINAP")

(IV) 2,2'-bis(di-m-tolylphosphino)-1,1'-binaphthyl (hereinafter abbreviated as "m-T-BINAP")

(V) 2,2'-bis[di-(3,5-dimethylphenyl)phosphino]-1,1'-binaphthyl (hereinafter abbreviated as "DM-BINAP")

(VI) 2,2'-bis[di-(3,5-di-tert-butylphenyl)phosphino]-1,1'-binaphthyl (hereinafter abbreviated as "DtBu-BINAP")

(VII) 2,2'-bis[di-(p-methoxyphenyl)phosphino]-1,1'-binaphthyl (hereinafter abbreviated as "MeO-BINAP")

(VIII) 2,2'-bis[di-(p-chlorophenyl)phosphino]-1,1'-binaphthyl (hereinafter abbreviated as "p-Cl-BINAP")

(IX) 2,2'-bis(di-2-naphthylphosphino)-1,1'-binaphthyl (hereinafter abbreviated as "Naph-BINAP")

(X) 2,2'-bis(dicyclopentylphosphino)-1,1'-binaphthyl (hereinafter abbreviated as "cpBINAP")

(XI) 2,2'-bis(dicyclohexylphosphino)-1,1'-binaphthyl (hereinafter abbreviated as "CyBINAP")

These tertiary phosphines may be prepared by the methods described in JP-B Nos. H4-81596, H7-33392 and H7-68260 and JP-A Nos. H1-68386 or H4- 74192 and H9-124669.

The ruthenium-optically active phosphine complex [RuI(arene)(L)]I (formula (3)) can be obtained by the method described in JP-B No. H7-57758 or JP-A No. H5-111639. As specific examples of the ruthenium-optically active phosphine complex thus produced, the following compounds may be given.

[RuI(benzene)(BINAP)]I
[RuI(benzene)(T-BINAP)]I
[RuI(benzene)(tBu-BINAP)]I
[RuI(benzene)(m-T-BINAP)]I
[RuI(benzene)(DM-BINAP)]I
[RuI(benzene)(DtBu-BINAP)]I
[RuI(benzene)(MeO-BINAP)]I
[RuI(benzene)(p-Cl-BINAP)]I
[RuI(benzene)(Naph-BINAP)]I
[RuI(benzene)(cpBINAP)]I

[RuI(benzene)(CyBINAP)]I
[RuI(p-cymene)(BINAP)]I
[RuI(p-cymene)(T-BINAP)]I
[RuI(p-cymene)(tBu-BINAP)]I
[RuI(p-cymene)(m-T-BINAP)]I
[RuI(p-cymene)(DM-BINAP)]I
[RuI(p-cymene)(DtBu-BINAP)]I
[RuI(p-cymene)(MeO-BINAP)]I
[RuI(p-cymene)(p-Cl-BINAP)]I
[RuI(p-cymene)(Naph-BINAP)]I
[RuI(p-cymene)(cpBINAP)]I
[RuI(p-cymene)(CyBINAP)]I As examples of 2,2'-bis(diphenylphosphino)-1,1'-octahydrobinaphthyl represented by H8-R1-BINAP of the formula (8), the same compounds as in the case of R1-BINAP can be given.

$R^1$-SEGPHOSs can be obtained from 3,4-methylenedioxybenzene through 5 steps according to the method described in JP-A No. H8-311211 (Publication No. H10-182678): diphenyl (3,4-methylenedioxyphenyl) phosphine oxide is prepared from a Grignard reagent of 3,4-methylenedioxybromobenzene and diphenylphosphinylchloride. The product obtained is iodized and coupled in the presence of copper powder, whereby racemic $R^1$-SEGPHOS oxides are obtained. The resultant product is optically resolved and reduced by trichlorosilane, so that an optically active R1-SEGPHOS is obtained.

As specific examples of the tertiary phosphine, the following compounds may be given. Although all tertiary phosphines embrace an (R) isomer and an (S) isomer, the notation of these isomers is omitted (the same as follows).

As a second aspect of the invention, the ruthenium-iodo-optically active phosphine complexes represented by the formulae (12), (13) and (14) (hereinafter collectively abbreviated as "[RuI$_a$(R$^1$-SEGPHOS)(SOL)$_b$](I)$_c$(anion)$_d$", and in this formula, a, b, c and d respectively denote numerals comprising a combination of a=0, b=4, c=2 and d=0, a combination of a=0, b=4, c=1 and d=1 or a combination of a=1, b=3, c=0 and d=1) can be obtained using the aforementioned two methods, which are indicated by the reaction formulae 1 and 2 shown below:

[Reaction formula 1]

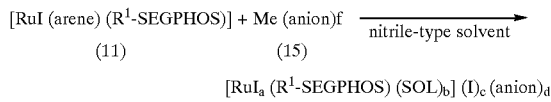

[Reaction formula 2]

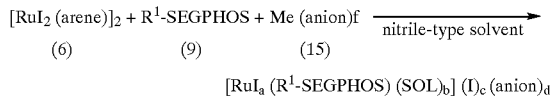

Specifically, as indicated by the reaction formula 1, the ruthenium-phosphine complex (11) and the perfluoroalkylsulfonate (15) are placed in a reaction container in which air is replaced by an inert gas, e.g., nitrogen and heated with stirring in a nitrile type solvent to react, followed by distilling the solvent. The resulting product is then stirred in a two-layer solvent of methylene chloride/water at room temperature, followed by washing, to obtain the ruthenium-iodo-optically active phosphine complex. Alternatively, as indicated by the reaction formula 2, the ruthenium complex (6), the phosphine ligand (9) and the perfluoroalkylsulfonates (15) are heated with stirring in a nitrile type solvent to react, followed by distilling the nitrile type solvent. The resulting product is then stirred in a two-layer solvent of methylene chloride/water at room temperature, followed by washing, to obtain the ruthenium-iodo-optically active phosphine complex.

Judging from the result of $^{31}$P NMR and the descriptions in the aforementioned literature: K. Mashima et al; J. Chem. Soc. Dalton Trans., pp. 2099–2107 (1992), the complex thus obtained is a mixture of [Ru(SEGPHOS)(sol)$_4$]$_2^+$(anion)$_2$, [Ru(SEGPHOS)(sol)$_4$]$_2^+$(I$^-$)$_2$, [Ru(SEGPHOS)(SOL)$_4$]$_2^+$I$^-$ (anion) and [RuI(SEGPHOS)(SOL)$_3$]$^+$(anion).

The perfluoroalkylsulfonates represented by the compound (15) used in the present invention are used to substitute part or all of iodine ions present in the precursor of catalyst represented by the compound (5) or (7) with perfluoroalkylsulfone anions. A metal or ammonium cation contained in the perfluoroalkyl-sulfonates represented by the compound (15) is combined with an iodine anion to form salts thereby removing the iodine anion from the system. Therefore, no particular limitation is imposed on the metal or ammonium cation in the perfluoroalkylsulfonates insofar as it combines with the iodine anion to form salts. Incidentally, there is no large difference between the compositions of the complexes produced by the aforementioned two methods.

Examples of the aryl group represented by $R^1$ in $R^1$-SEGPHOS of the formula (4) in the ruthenium-optically active phosphine complex (11) which is the raw material used in the production of RuI$_a$(R$^1$-SEGPHOS)(SOL)$_b$](I)$_c$ (anion)$_d$ include a phenyl group, 2-naphthyl group, phenyl groups having a substituent such as a p-substituted phenyl group, m-substituted phenyl group and m-di-substituted-phenyl group and 2-naphthyl groups having a substituent such as 6-substituted-2-naphthyl group. Examples of the substituent which can be substituted with the phenyl group and the naphthyl group include a lower alkyl group (in which "lower" means a linear or branched chain having 1–4 carbon atoms, the same as follows) such as a methyl group, ethyl group, n-propyl group, iso-propyl group, n-butyl group, sec-butyl group and tert-butyl group and lower alkoxy group, lower alkylamine group and halogen atom such as a chlorine atom. As the cycloalkyl group, represented by R1, having 3 to 8 carbon atoms, a cyclopentyl group and a cyclohexyl group are especially preferable.

$R^1$-SEGPHOSs can be obtained from 3,4-methylenedioxybenzene through 5 steps as mentioned above (JP-A No. H10-182678).

In the first and second aspect of the invention, the following compounds may be given as specific examples of the tertiary phosphine. Although all tertiary phosphines embrace an (R) isomer and an (S) isomer, the notation of these isomers is omitted (the same as follows).

(XII) [(5,6),(5',6')-bis(methylenedioxy)biphenyl-2,2'-diyl] bis(diphenylphosphine) (hereinafter abbreviated simply as "SEGPHOS")

(XIII) [(5,6),(5',6')-bis(methylenedioxy)biphenyl-2,2'-diyl] bis(di-p-tolylphosphine) (hereinafter abbreviated as "T-SEGPHOS")

(XIV) [(5,6),(5',6')-bis(methylenedioxy)biphenyl-2,2'-diyl] bis(di-(p-tert-butylphenyl)phosphine) (hereinafter abbreviated as "tBu-SEGPHOS")

(XV) [(5,6),(5',6')-bis(methylenedioxy)biphenyl-2,2'-diyl] bis(di-m-tolyl-phosphine) (hereinafter abbreviated as "m-T-SEGPHOS")

(XVI) [(5,6),(5',6')-bis(methylenedioxy)biphenyl-2,2'-diyl] bis[di-(3,5-dimethylphenyl)phosphine] (hereinafter abbreviated as "DM-SEGPHOS")

(XVII) [(5,6),(5',6')-bis(methylenedioxy)biphenyl-2,2'-diyl] bis[di-(3,5-di-tertbutylphenyl)phosphine] (hereinafter abbreviated as "DtBu-SEGPHOS")

(XVIII) [(5,6),(5',6')-bis(methylenedioxy)biphenyl-2,2'-diyl]bis[di-(p-methoxyphenyl)phosphine) (hereinafter abbreviated as "MeO-SEGPHOS")

(XIX) [(5,6),(5',6')-bis(methylenedioxy)biphenyl-2,2'-diyl]bis[di-(p-chlorophenyl)phosphine) (hereinafter abbreviated as "p-Cl-SEGPHOS")

(XX) [(5,6),(5',6')-bis(methylenedioxy)biphenyl-2,2'-diyl]bis(di-2-naphthylphosphine) (hereinafter abbreviated as "Naph-SEGPHOS")

(XXI) [(5,6),(5',6')-bis(methylenedioxy)biphenyl-2,2'-diyl]bis(dicyclopentylphosphine) (hereinafter abbreviated as "cpSEGPHOS")

(XXII) [(5,6),(5',6')-bis(methylenedioxy)biphenyl-2,2'-diyl]bis(dicyclohexylphosphine) (hereinafter abbreviated as "CySEGPHOS")

(XXIII) [Bis(6,6'-dimethylbiphenyl-2,2'-](diphenylphosphine) (hereinafter abbreviated as "BIPHEP")

(XXIV) [Bis(6,6'-dimethylbiphenyl-2,2'-](dicyclohexylphosphine) (hereinafter abbreviated as "BICHEP")

(XXV) [Bis(6,6'-dimethoxybiphenyl-2,2'-](diphenylphosphine) (hereinafter abbreviated as "MBIPHEP")

(XXVI) [Bis(6,6'-dimethoxybiphenyl-2,2'-](dicyclohexylphosphine) (hereinafter abbreviated as "MBICHEP")

In the first aspect of the invention, the ruthenium-optically active phosphine complex represented by either [RuI(arene)(L)]I (3) in which L is $R^1$-SEGPHOS or [RuI(arene)($R^1$-SEGPHOS)]I may be produced according to the methods described in JP-A Nos. H2-191289 and H5-111639.

As specific examples of the ruthenium-optically active phosphine complex having the formula (3) which can be produced in such a manner, the following compounds are given.

[RuI(benzene)(SEGPHOS)]I
[RuI(benzene)(T-SEGPHOS)]I
[RuI(benzene)(tBu-SEGPHOS)]I
[RuI(benzene)(m-T-SEGPHOS)]I
[RuI(benzene)(DM-SEGPHOS)]I
[RuI(benzene)(DtBu-SEGPHOS)]I
[RuI(benzene)(MeO-SEGPHOS)]I
[RuI(benzene)(p-Cl-SEGPHOS)]I
[RuI(benzene)(Naph-SEGPHOS)]I
[RuI(benzene)(cpSEGPHOS)]I
[RuI(benzene)(CySEGPHOS)]I
[RuI(p-cymene)(SEGPHOS)]I
[RuI(p-cymene)(T-SEGPHOS)]I
[RuI(p-cymene)(tBu-SEGPHOS)]I
[RuI(p-cymene)(m-T-SEGPHOS)]I
[RuI(p-cymene)(DM-SEGPHOS)]I
[RuI(p-cymene)(DtBu-SEGPHOS)]I
[RuI(p-cymene)(MeO-SEGPHOS)]I
[RuI(p-cymene)(p-Cl-SEGPHOS)]I
[RuI(p-cymene)(Naph-SEGPHOS)]I
[RuI(p-cymene)(cpSEGPHOS)]I
[RuI(p-cymene)(CySEGPHOS)]I As examples of BIPHEP, BICHEP, MBIPHEP and MBICHEP, similar compounds to those of SEGPHOS may be given.

In the second aspect of the invention, the ruthenium-optically active phosphine complex represented by [RuI(arene)($R^1$-SEGPHOS)] may be obtained by stirring, under heat, the complex of the formula (7a) and $R^1$-SEGPHOS of the formula (4a) in an organic solvent at 50° C. for about 2 hour (Patent Applications JP-A Nos. H2-191289 and H5-111639, supra).

In the above reaction formulae 1 and 2, examples of the hydrocarbon having a benzene ring represented by arene include benzene, toluene, xylene, mesitylene, p-cymene, hexamethylbenzene, methoxybenzene and methyl benzoate.

As specific examples of the ruthenium-optically active phosphine complex [RuI(arene)($R^1$-SEGPHOS)]I represented in the reaction formula 1, which can be produced in such a manner, the following compounds may be given: benzene and p-cymene as examples of arene; the aforementioned SEGPHOS, T-SEGPHOS, tBu-SEGPHOS, m-T-SEGPHOS, DM-SEGPHOS, DtBu-SEGPHOS, MeO-SEGPHOS, p-Cl-SEGPHOS, Naph-SEGPHOS, cpSEGPHOS and CySEGPHOS, as examples of $R^1$-SEGPHOS.

In both aspects of the invention, the ruthenium-iodo complex represented by [RuI$_2$(arene)]$_2$ can be produced according to the method of Zelonka (R. A. Zelonka et al.; Can. J. Chem., Vol 50, 3063 (1972)). Specific Examples of the resulting ruthenium-optically active phosphine complex include the following compounds:

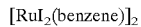

[RuI$_2$(benzene)]$_2$

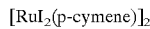

[RuI$_2$(p-cymene)]$_2$

In the first aspect of the invention, the ruthenium-iodo-optically active bidentate phosphine complex represented by the formula (1) is produced by reacting the ruthenium-optically active phosphine complex [RuI(arene)(L)]I of the formula (3) either with carboxylates $(T^1)_aZ^1$ of the formula (4) or with salts $Z^2{}_b(T^2)_c$ of the formula (5) in a polar solvent. It can also be produced by reacting the ruthenium complex [RuI$_2$(arene)]$_2$ of the formula (6) with the phosphine ligand (L) in a polar solvent and further reacting the resulting product with salts represented by either $(T^1)_aZ^1$ of the formula (4) or $Z^2b(T^2)c$ of the formula (5).

Examples of the carboxylates represented by the formula (4) include carboxylates of alkali metals such as lithium formate, lithium acetate, lithium propionate, lithium butyrate, lithium pyruvate, lithium benzoate, lithium trifluoroacetate, sodium formate, sodium acetate, sodium propionate, sodium butyrate, sodium pyruvate, sodium benzoate, sodium trifluoroacetate, potassium formate, potassium acetate, potassium propionate, potassium butyrate, potassium pyruvate, potassium benzoate and potassium trifluoroacetate; carboxylates of alkali earth metals such as calcium formate, calcium acetate, calcium propionate, calcium butyrate, calcium pyruvate, calcium benzoate and calcium trifluoroacetate; and other carboxylates such as silver formate, silver acetate, silver propionate, silver butyrate, silver pyruvate, silver benzoate and silver trifluoroacetate. Among these compounds, sodium acetate and sodium trifluoroacetate are preferred.

Examples of the salts represented by the formula (5) include sodium methane sulfonate (sodium methylate) (hereinafter abbreviated as "NaOMs"), methane sulfonate (sodium tosylate)(hereinafter abbreviated as "NaOTs"), lithium trifluoromethane sulfonate (lithium triflate) (hereinafter abbreviated as "LiOTf"), potassium nonafluorobutane sulfonate (hereinafter abbreviated as "KOS(O)$_2$C$_4$F$_9$"), NaOTf, Mg(Otf)$_2$, AgOTf, NH$_4$OTf, LiBF$_4$, NaBF$_4$, KBF$_4$, AgBF$_4$, Ca(BF$_4$)$_2$, NH$_4$BF$_4$, LiPF$_6$, NaPF$_6$, KPF$_6$, AgPF$_6$, Ca(PF$_6$)$_2$, NH$_4$PF$_6$, LiClO$_4$, NaClO$_4$, KClO$_4$, AgClO$_4$, Ca(ClO$_4$)$_2$, NH$_4$ClO$_4$, LiBPh$_4$, NaBPh$_4$, KBPh$_4$, AgBPh$_4$, Ca(BPh$_4$)$_2$, NH$_4$BPh$_4$, Na$_2$SO$_4$, K$_2$SO$_4$, MgSO$_4$, CaSO$_4$(NH$_4$)$_2$SO$_4$, Na$_2$CO$_3$, K$_2$CO$_3$, MgCO$_3$, CaCO$_3$, (NH$_4$)$_2$CO$_3$ and potassium heptadecafluorooctane sulfonate (hereinafter abbreviated as "KOS(O)$_2$C$_8$F$_7$"). Among these compounds, NaOTf, NaPF$_6$, NH$_4$PF$_6$, NaClO$_4$, NH$_4$ClO$_4$, KOS(O)$_2$C$_4$F$_9$ and KOS(O)$_2$C$_8$F$_{17}$ are particularly preferred.

The amount of the carboxylates (T$^1$)$_a$Z$^1$ of the formula (4) or the salts Z$^2{}_b$(T$^2$)$_c$ of the formula (5) is preferably about 0.5 to 5 equivalents by mol and more preferably about 1 to 4 equivalents by mol based on one mol of the ruthenium optically active phosphine complex [RuI(arene)(L)]I of the formula (3) or of the ruthenium complex [RuI$_2$(arene)]$_2$ of the formula (6).

Given as examples of the polar solvent used in the reaction are lower alcohols such as methanol and ethanol, dimethylformamide, dimethylsulfoxide, dioxane, tetrahydrofuran and a mixed solvent of methanol-methylene chloride. The ruthenium-iodo-optically active bidentate phosphine complex represented by [Ru—(I)$_q$—(T$^1$)$_n$(L)]$_m$(T$^2$)$_p$ of the formula (1) in the present invention is produced either at temperatures ranging from about 40 to 60° C. and preferably from 50 to 55° C. when it is produced using the carboxylates represented by (T$^1$)$_a$Z$^1$ of the formula (4) or at temperatures ranging from about 60 to 90° C. and preferably from 70 to 80° C. when it is produced using the salts Z$^2{}_b$(T$^2$)$_c$ of the formula (5). The reaction time is about 10 to 40 hours and preferably about 15 to 20 hours. After the reaction is completed, the hydrophobic organic solvent layer is taken out and distilled. The resulting product is dried, to obtain the objective compound.

The objective ruthenium-iodo-optically active bidentate phosphine complex [Ru—(I)$_q$—(T$^1$)$_n$(L)]$_m$(T$^2$)$_p$ of the formula (1) of the present invention is formed by reacting the ruthenium-optically phosphine complex [RuI(arene)(L)]I of the formula (3) with either the carboxylates (T$^1$)$_a$Z$^1$ of the formula (4) or the salts Z$^2{}_b$(T$^2$)$_c$ of the formula (5), so that the arene molecule is removed from the complex formed. The ruthenium-iodo-optically active bidentate phosphine complex of the formula (1) may also be formed by reacting a ruthenium complex [RuI$_2$(arene)]$_2$ of the formula (6), an optically active bidentate phosphine, and a carboxylate (T$^1$)$_a$Z$^1$ of the formula (4) or a salt Z$^2{}_b$(T$^2$)$_c$ of the formula (5), so that the arene molecule is removed from the complex formed. When the carboxylates are used, the complex formed has a carboxyl group in place of the iodine atom. Consequently, the complex formed consists of a prerequisite minimum constituents of the invention, i.e., ruthenium, iodine, a carboxyl group or a T$^2$ group of the salts and optically active tertiary phosphine, and is represented by [Ru—(I)$_q$—(T$^1$)$_n$(L)]$_m$(T$^2$)$_p$ of the general formula (1).

As typical examples of the ruthenium-iodo-optically active bidentate phosphine complex (1) of the present invention, the following compounds may be given. Each of the absolute configurations of the complex can be obtained, depending on which of the absolute configuration of the phosphine, (R) isomer or (S) isomer, is used. However, the notation of these isomers is omitted.

[RuI(HCOO)(BINAP)]$_2$
[RuI(HCOO)(T-BINAP)]$_2$
[RuI(CH$_3$COO)(BINAP)]$_2$
[RuI(CH$_3$COO)(T-BINAP)]$_2$
[RuI(CH$_3$COO)(tBu-BINAP)]$_2$
[RuI(CH$_3$COO)(m-T-BINAP)]$_2$
[RuI(CH$_3$COO)(DM-BINAP)]$_2$
[RuI(CH$_3$COO)(DtBu-BINAP)]$_2$
[RuI(CH$_3$COO)(MeO-BINAP)]$_2$
[RuI(CH$_3$COO)(p-Cl-BINAP)]$_2$
[RuI(CH$_3$COO)(Naph-BINAP)]$_2$
[RuI(CH$_3$COO)(cpBINAP)]$_2$
[RuI(CH$_3$COO)(CyBINAP)]$_2$
[RuI(CH$_3$CH$_2$COO)(BINAP)]$_2$
[RuI(CH$_3$CH$_2$COO)(T-BINAP)]$_2$
[RuI(CH$_3$CH$_2$CH$_2$COO)(BINAP)]$_2$
[RuI(CH$_3$CH$_2$CH$_2$COO)(T-BINAP)]$_2$
[RuI(CH$_3$COCOO)(BINAP)]$_2$
[RuI(CH$_3$COCOO)(T-BINAP)]$_2$
[RuI(PhCOO)(BINAP)]$_2$
[RuI(PhCOO)(T-BINAP)]$_2$
[RuI(CF$_3$COO)(BINAP)]$_2$
[RuI(CF$_3$COO)(T-BINAP)]$_2$
[Ru—I-(BINAP)](OMs)
[Ru—I-(BINAP)](OTs)
[Ru—I-(BINAP)](OTf)
[Ru—I-(BINAP)]{OS(O)$_2$C$_4$F$_9$}
[Ru—I-(BINAP)](BF$_4$)
[Ru—I-(BINAP)](PF$_6$)
[Ru—I-(BINAP)](ClO$_4$)
[Ru—I-(BINAP)](BPh$_4$)
[Ru—I-(BINAP)](SO$_4$)
[Ru—I-(BINAP)](CO$_3$)
[Ru—I—(T-BINAP)](OMs)
[Ru—I—(T-BINAP)](OTs)
[Ru—I—(T-BINAP)](OTf)
[Ru—I—(T-BINAP)]{OS(O)$_2$C$_4$F$_9$}
[Ru—I—(T-BINAP)](BF$_4$)
[Ru—I—(T-BINAP)](PF$_6$)
[Ru—I—(T-BINAP)](ClO$_4$)
[Ru—I—(T-BINAP)](BPh$_4$)
[Ru—I—(T-BINAP)](SO$_4$)
[Ru—I—(T-BINAP)](CO$_3$)
[Ru—I-(tBu-BINAP)](OMs)
[Ru—I-(tBu-BINAP)](OTs)
[Ru—I-(tBu-BINAP)](OTf)
[Ru—I-(tBu-BINAP)]{OS(O)$_2$C$_4$F$_9$}
[Ru—I-(tBu-BINAP)](BF$_4$)
[Ru—I-(tBu-BINAP)](PF$_6$)
[Ru—I-(tBu-BINAP)](ClO$_4$)
[Ru—I-(tBu-BINAP)](BPh$_4$)
[Ru—I-(tBu-BINAP)](SO$_4$)
[Ru—I-(tBu-BINAP)](CO$_3$)
[Ru—I-(m-T-BINAP)](OMs)
[Ru—I-(m-T-BINAP)](OTs)
[Ru—I-(m-T-BINAP)](OTf)
[Ru—I-(m-T-BINAP)]{OS(O)$_2$C$_4$F$_9$}
[Ru—I-(m-T-BINAP)](BF$_4$)
[Ru—I-(m-T-BINAP)](PF$_6$)
[Ru—I-(m-T-BINAP)](ClO$_4$)
[Ru—I-(m-T-BINAP)](BPh$_4$)
[Ru—I-(m-T-BINAP)](SO$_4$)
[Ru—I-(m-T-BINAP)](CO$_3$)
[Ru—I-(DM-BINAP)](OMs)
[Ru—I-(DM-BINAP)](OTs)
[Ru—I-(DM-BINAP)](OTf)
[Ru—I-(DM-BINAP)]{OS(O)$_2$C$_4$F$_9$}
[Ru—I-(DM-BINAP)](BF$_4$)
[Ru—I-(DM-BINAP)](PF$_6$)
[Ru—I-(DM-BINAP)](ClO$_4$)
[Ru—I-(DM-BINAP)](BPh$_4$)
[Ru—I-(DM-BINAP)](SO$_4$)
[Ru—I-(DM-BINAP)](CO$_3$)
[Ru—I-(DtBu-BINAP)](OMs)
[Ru—I-(DtBu-BINAP)](OTs)
[Ru—I-(DtBu-BINAP)](OTf)
[Ru—I-(DtBu-BINAP)]{OS(O)$_2$C$_4$F$_9$}
[Ru—I-(DtBu-BINAP)](BF$_4$)
[Ru—I-(DtBu-BINAP)](PF$_6$)
[Ru—I-(DtBu-BINAP)](ClO$_4$)

[Ru—I-(DtBu-BINAP)](BPh$_4$)
[Ru—I-(DtBu-BINAP)](SO$_4$)
[Ru—I-(DtBu-BINAP)](CO$_3$)
[Ru—I-(MeO-BINAP)](OMs)
[Ru—I-(MeO-BINAP)](OTs)
[Ru—I-(MeO-BINAP)](OTf)
[Ru—I-(MeO-BINAP)]{OS(O)$_2$C$_4$F$_9$}
[Ru—I-(MeO-BINAP)](BF$_4$)
[Ru—I-(MeO-BINAP)](PF$_6$)
[Ru—I-(MeO-BINAP)](ClO$_4$)
[Ru—I-(MeO-BINAP)](BPh$_4$)
[Ru—I-(MeO-BINAP)](SO$_4$)
[Ru—I-(MeO-BINAP)](CO$_3$)
[Ru—I-(p-Cl-BINAP)](OMs)
[Ru—I-(p-Cl-BINAP)](OTs)
[Ru—I-(p-Cl-BINAP)](OTf)
[Ru—I-(p-Cl-BINAP)]{OS(O)$_2$C$_4$F$_9$}
[Ru—I-(p-Cl-BINAP)](BF$_4$)
[Ru—I-(p-Cl-BINAP)](PF$_6$)
[Ru—I-(p-Cl-BINAP)](ClO$_4$)
[Ru—I-(p-Cl-BINAP)](BPh$_4$)
[Ru—I-(p-Cl-BINAP)](SO$_4$)
[Ru—I-(p-Cl-BINAP)](CO$_3$)
[Ru—I-(Naph-BINAP)](OMs)
[Ru—I-(Naph-BINAP)](OTs)
[Ru—I-(Naph-BINAP)](OTf)
[Ru—I-(Naph-BINAP)]{OS(O)$_2$C$_4$F$_9$}
[Ru—I-(Naph-BINAP)](BF$_4$)
[Ru—I-(Naph-BINAP)](PF$_6$)
[Ru—I-(Naph-BINAP)](ClO$_4$)
[Ru—I-(Naph-BINAP)](BPh$_4$)
[Ru—I-(Naph-BINAP)](SO$_4$)
[Ru—I-(Naph-BINAP)](CO$_3$)
[Ru—I-(cpBINAP)](OMs)
[Ru—I-(cpBINAP)](OTs)
[Ru—I-(cpBINAP)](OTf)
[Ru—I-(cpBINAP)]{OS(O)$_2$C$_4$F$_9$}
[Ru—I-(cpBINAP)](BF$_4$)
[Ru—I-(cpBINAP)](PF$_6$)
[Ru—I-(cpBINAP)](ClO$_4$)
[Ru—I-(cpBINAP)](BPh$_4$)
[Ru—I-(cpBINAP)](SO$_4$)
[Ru—I-(cpBINAP)](CO$_3$)
[Ru—I-(CyBINAP)](OMs)
[Ru—I-(CyBINAP)](OTs)
[Ru—I-(CyBINAP)](OTf)
[Ru—I-(CyBINAP)]{OS(O)$_2$C$_4$F$_8$}
[Ru—I-(CyBINAP)](BF$_4$)
[Ru—I-(CyBINAP)](PF$_6$)
[Ru—I-(CyBINAP)](ClO$_4$)
[Ru—I-(CyBINAP)](BPh$_4$)
[Ru—I-(CyBINAP)](SO$_4$)
[Ru—I-(CyBINAP)](CO$_3$)
[Ru(I)$_{1.5}$(BINAP)]$_2$(OMs)
[Ru(I)$_{1.5}$(BINAP)]$_2$(OTs)
[Ru(I)$_{1.5}$(BINAP)]$_2$(OTf)
[Ru(I)$_{1.5}$(BINAP)]$_2${OS(O)$_2$C$_4$F$_9$}
[Ru(I)$_{1.5}$(BINAP)]$_2$(BF$_4$)
[Ru(I)$_{1.5}$(BINAP)]$_2$(PF$_6$)
[Ru(I)$_{1.5}$(BINAP)]$_2$(ClO$_4$)
[Ru(I)$_{1.5}$(BINAP)]$_2$(BPh$_4$)
[Ru(I)$_{1.5}$(T-BINAP)]$_2$(OMs)
[Ru(I)$_{1.5}$(T-BINAP)]$_2$(OTs)
[Ru(I)$_{1.5}$(T-BINAP)]$_2$(OTf)
[Ru(I)$_{1.5}$(T-BINAP)]$_2${OS(O)$_2$C$_4$F$_9$}
[Ru(I)$_{1.5}$(T-BINAP)]$_2$(BF$_4$)
[Ru(I)$_{1.5}$(T-BINAP)]$_2$(PF$_6$)
[Ru(I)$_{1.5}$(T-BINAP)]$_2$(ClO$_4$)
[Ru(I)$_{1.5}$(T-BINAP)]$_2$(BPh$_4$)
[Ru(I)$_{1.5}$(tBu-BINAP)]$_2$(OMs)
[Ru(I)$_{1.5}$(tBu-BINAP)]$_2$(OTs)
[Ru(I)$_{1.5}$(tBu-BINAP)]$_2$(OTf)
[Ru(I)$_{1.5}$(tBu-BINAP)]$_2${OS(O)$_2$C$_4$F$_9$}
[Ru(I)$_{1.5}$(tBu-BINAP)]$_2$(BF$_4$)
[Ru(I)$_{1.5}$(tBu-BINAP)]$_2$(PF$_6$)
[Ru(I)$_{1.5}$(tBu-BINAP)]$_2$(ClO$_4$)
[Ru(I)$_{1.5}$(tBu-BINAP)]$_2$(BPh$_4$)
[Ru(I)$_{1.5}$(m-T-BINAP)]$_2$(OMs)
[Ru(I)$_{1.5}$(m-T-BINAP)]$_2$(OTs)
[Ru(I)$_{1.5}$(m-T-BINAP)]$_2$(OTf)
[Ru(I)$_{1.5}$(m-T-BINAP)]$_2${OS(O)$_2$C$_4$F$_9$}
[Ru(I)$_{1.5}$(m-T-BINAP)]$_2$(BF$_4$)
[Ru(I)$_{1.5}$(m-T-BINAP)]$_2$(PF$_6$)
[Ru(I)$_{1.5}$(m-T-BINAP)]$_2$(ClO$_4$)
[Ru(I)$_{1.5}$(m-T-BINAP)]$_2$(BPh$_4$)
[Ru(I)$_{1.5}$(DM-BINAP)]$_2$(OMs)
[Ru(I)$_{1.5}$(DM-BINAP)]$_2$(OTs)
[Ru(I)$_{1.5}$(DM-BINAP)]$_2$(OTf)
[Ru(I)$_{1.5}$(DM-BINAP)]$_2${OS(O)$_2$C$_4$F$_9$}
[Ru(I)$_{1.5}$(DM-BINAP)]$_2$(BF$_4$)
[Ru(I)$_{1.5}$(DM-BINAP)]$_2$(PF$_6$)
[Ru(I)$_{1.5}$(DM-BINAP)]$_2$(ClO$_4$)
[Ru(I)$_{1.5}$(DM-BINAP)]$_2$(BPh$_4$)
[Ru(I)$_{1.5}$(DtBu-BINAP)]$_2$(OMs)
[Ru(I)$_{1.5}$(DtBu-BINAP)]$_2$(OTs)
[Ru(I)$_{1.5}$(DtBu-BINAP)]$_2$(OTf)
[Ru(I)$_{1.5}$(DtBu-BINAP)]$_2$(BF$_4$)
[Ru(I)$_{1.5}$(DtBu-BINAP)]$_2$(PF$_6$)
[Ru(I)$_{1.5}$(DtBu-BINAP)]$_2$(ClO$_4$)
[Ru(I)$_{1.5}$(DtBu-BINAP)]$_2$(BPh$_4$)
[Ru(I)$_{1.5}$(MeO-BINAP)]$_2$(OMs)
[Ru(I)$_{1.5}$(MeO-BINAP)]$_2$(OTs)
[Ru(I)$_{1.5}$(MeO-BINAP)]$_2$(OTf)
[Ru(I)$_{1.5}$(MeO-BINAP)]$_2${OS(O)$_2$C$_4$F$_9$}
[Ru(I)$_{1.5}$(MeO-BINAP)]$_2$(BF$_4$)
[Ru(I)$_{1.5}$(MeO-BINAP)]$_2$(PF$_6$)
[Ru(I)$_{1.5}$(MeO-BINAP)]$_2$(ClO$_4$)
[Ru(I)$_{1.5}$(MeO-BINAP)]$_2$(BPh$_4$)
[Ru(I)$_{1.5}$(p-Cl-BINAP)]$_2$(OMs)
[Ru(I)$_{1.5}$(p-Cl-BINAP)]$_2$(OTs)
[Ru(I)$_{1.5}$(p-Cl-BINAP)]$_2$(OTf)
[Ru(I)$_{1.5}$(p-Cl-BINAP)]$_2${OS(O)$_2$C$_4$F$_9$}
[Ru(I)$_{1.5}$(p-Cl-BINAP)]$_2$(BF$_4$)
[Ru(I)$_{1.5}$(p-Cl-BINAP)]$_2$(PF$_6$)
[Ru(I)$_{1.5}$(p-Cl-BINAP)]$_2$(ClO$_4$)
[Ru(I)$_{1.5}$(p-Cl-BINAP)]$_2$(BPh$_4$)
[Ru(I)$_{1.5}$(Naph-BINAP)]$_2$(OMs)
[Ru(I)$_{1.5}$(Naph-BINAP)]$_2$(OTs)
[Ru(I)$_{1.5}$(Naph-BINAP)]$_2$(OTf)
[Ru(I)$_{1.5}$(Naph-BINAP)]$_2${OS(O)$_2$C$_4$F$_9$}
[Ru(I)$_{1.5}$(Naph-BINAP)]$_2$(BF$_4$)
[Ru(I)$_{1.5}$(Naph-BINAP)]$_2$(PF$_6$)
[Ru(I)$_{1.5}$(Naph-BINAP)]$_2$(ClO$_4$)
[Ru(I)$_{1.5}$(Naph-BINAP)]$_2$(BPh$_4$)
[Ru(I)$_{1.5}$(cpBINAP)]$_2$(OMs)
[Ru(I)$_{1.5}$(cpBINAP)]$_2$(OTs)
[Ru(I)$_{1.5}$(cpBINAP)]$_2$(OTf)
[Ru(I)$_{1.5}$(cpBINAP)]$_2${OS(O)$_2$C$_4$F$_9$}
[Ru(I)$_{1.5}$(cpBINAP)]$_2$(BF$_4$)
[Ru(I)$_{1.5}$(cpBINAP)]$_2$(PF$_6$)
[Ru(I)$_{1.5}$(cpBINAP)]$_2$(ClO$_4$)
[Ru(I)$_{1.5}$(cpBINAP)]$_2$(BPh$_4$)
[Ru(I)$_{1.5}$(CyBINAP)]$_2$(OMs)
[Ru(I)$_{1.5}$(CyBINAP)]$_2$(OTs)

[Ru(I)$_{1.5}$(CyBINAP)]$_2$(OTf)
[Ru(I)$_{1.5}$(CyBINAP)]$_2${OS(O)$_2$C$_4$F$_9$}
[Ru(I)$_{1.5}$(CyBINAP)]$_2$(BF$_4$)
[Ru(I)$_{1.5}$(CyBINAP)]$_2$(PF$_6$)
[Ru(I)$_{1.5}$(CyBINAP)]$_2$(ClO$_4$)
[Ru(I)$_{1.5}$(CyBINAP)]$_2$(BPh$_4$)
[Ru(I)$_{1.5}$(BINAP)]$_2${OS(O)$_2$C$_8$F$_{17}$}
[Ru(I)$_{1.5}$(T-BINAP)]$_2${OS(O)$_2$C$_8$F$_{17}$}
[Ru(I)$_{1.5}$(tBu-BINAP)]$_2${OS(O)$_2$C$_8$F$_{17}$}
[Ru(I)$_{1.5}$(m-T-BINAP)]$_2${OS(O)$_2$C$_8$F$_{17}$}
[Ru(I)$_{1.5}$(DM-BINAP)]$_2${OS(O)$_2$C$_8$F$_{17}$}
[Ru(I)$_{1.5}$(DtBu-BINAP)]$_2${OS(O)$_2$C$_8$F$_{17}$}
[Ru(I)$_{1.5}$(MeO-BINAP)]$_2${OS(O)$_2$C$_8$F$_{17}$}
[Ru(I)$_{1.5}$(p-Cl-BINAP)]$_2${OS(O)$_2$C$_8$F$_{17}$}
[Ru(I)$_{1.5}$(cpBINAP)]$_2${OS(O)$_2$C$_8$F$_{17}$}
[Ru(I)$_{1.5}$(CyBINAP)]$_2${OS(O)$_2$C$_8$F$_{17}$}
[Ru(I)$_{1.5}$(BINAP)]$_2${OS(O)$_2$(iso-C$_3$F$_7$)}
[Ru(I)$_{1.5}$(T-BINAP)]$_2${OS(O)$_2$(iso-C$_3$F$_7$)}
[Ru(I)$_{1.5}$(BINAP)]$_2${OS(O)$_2$(tert-C$_4$F$_9$)}
[Ru(I)$_{1.5}$(T-BINAP)]$_2${OS(O)$_2$(tert-C$_4$F$_9$)}
[Ru(I)$_{1.5}$(BINAP)]$_2${OS(O)$_2$(cyclo-C$_6$F$_{11}$)}
[Ru(I)$_{1.5}$(T-BINAP)]$_2${OS(O)$_2$(cyclo-C$_6$F$_{11}$)}
[Ru—I-(SEGPHOS)](OMs)
[Ru—I-(SEGPHOS)](OTs)
[Ru—I-(SEGPHOS)](OTf)
[Ru—I-(SEGPHOS)]{OS(O)$_2$C$_4$F$_9$}
[Ru—I-(SEGPHOS)](BF$_4$)
[Ru—I-(SEGPHOS)](PF$_6$)
[Ru—I-(SEGPHOS)](ClO$_4$)
[Ru—I-(SEGPHOS)](BPh$_4$)
[Ru—I-(SEGPHOS)](SO$_4$)
[Ru—I-(SEGPHOS)](CO$_3$)
[Ru—I—(T-SEGPHOS)](OMs)
[Ru—I—(T-SEGPHOS)](OTs)
[Ru—I—(T-SEGPHOS)](OTf)
[Ru—I—(T-SEGPHOS)]{OS(O)$_2$C$_4$F$_9$}
[Ru—I—(T-SEGPHOS)](BF$_4$)
[Ru—I—(T-SEGPHOS)](PF$_6$)
[Ru—I—(T-SEGPHOS)](ClO$_4$)
[Ru—I—(T-SEGPHOS)](BPh$_4$)
[Ru—I—(T-SEGPHOS)](SO$_4$)
[Ru—I—(T-SEGPHOS)](CO$_3$)
[Ru—I-(tBu-SEGPHOS)](OMs)
[Ru—I-(tBu-SEGPHOS)](OTs)
[Ru—I-(tBu-SEGPHOS)](OTf)
[Ru—I-(tBu-SEGPHOS)]{OS(O)$_2$C$_4$F$_0$}
[Ru—I-(tBu-SEGPHOS)](BF$_4$)
[Ru—I-(tBu-SEGPHOS)](PF$_6$)
[Ru—I-(tBu-SEGPHOS)](ClO$_4$)
[Ru—I-(tBu-SEGPHOS)](BPh$_4$)
[Ru—I-(tBu-SEGPHOS)](SO$_4$)
[Ru—I-(tBu-SEGPHOS)](CO$_3$)
[Ru—I-(m-T-SEGPHOS)](OMs)
[Ru—I-(m-T-SEGPHOS)](OTs)
[Ru—I-(m-T-SEGPHOS)](OTf)
[Ru—I-(m-T-SEGPHOS)]{OS(O)$_2$C$_4$F$_9$}
[Ru—I-(m-T-SEGPHOS)](BF$_4$)
[Ru—I-(m-T-SEGPHOS)](PF$_6$)
[Ru—I-(m-T-SEGPHOS)](ClO$_4$)
[Ru—I-(m-T-SEGPHOS)](BPh$_4$)
[Ru—I-(m-T-SEGPHOS)](SO$_4$)
[Ru—I-(m-T-SEGPHOS)](CO$_3$)
[Ru—I-(DM-SEGPHOS)](OMs)
[Ru—I-(DM-SEGPHOS)](OTs)
[Ru—I-(DM-SEGPHOS)](OTf)
[Ru—I-(DM-SEGPHOS)]{OS(O)$_2$C$_4$F$_9$}
[Ru—I-(DM-SEGPHOS)](BF$_4$)
[Ru—I-(DM-SEGPHOS)](PF$_6$)
[Ru—I-(DM-SEGPHOS)](ClO$_4$)
[Ru—I-(DM-SEGPHOS)](BPh$_4$)
[Ru—I-(DM-SEGPHOS)](SO$_4$)
[Ru—I-(DM-SEGPHOS)](CO$_3$)
[Ru—I-(DtBu-SEGPHOS)](OMs)
[Ru—I-(DtBu-SEGPHOS)](OTs)
[Ru—I-(DtBu-SEGPHOS)](OTf)
[Ru—I-(DtBu-SEGPHOS)]{OS(O)$_2$C$_4$F$_9$}
[Ru—I-(DtBu-SEGPHOS)](BF$_4$)
[Ru—I-(DtBu-SEGPHOS)](PF$_6$)
[Ru—I-(DtBu-SEGPHOS)](ClO$_4$)
[Ru—I-(DtBu-SEGPHOS)](BPh$_4$)
[Ru—I-(DtBu-SEGPHOS)](SO$_4$)
[Ru—I-(DtBu-SEGPHOS)](CO$_3$)
[Ru—I-(MeO-SEGPHOS)](OMs)
[Ru—I-(MeO-SEGPHOS)](OTs)
[Ru—I-(MeO-SEGPHOS)](OTf)
[Ru—I-(MeO-SEGPHOS)]{OS(O)$_2$C$_4$F$_9$}
[Ru—I-(MeO-SEGPHOS)](BF$_4$)
[Ru—I-(MeO-SEGPHOS)](PF$_6$)
[Ru—I-(MeO-SEGPHOS)](ClO$_4$)
[Ru—I-(MeO-SEGPHOS)](BPh$_4$)
[Ru—I-(MeO-SEGPHOS)](SO$_4$)
[Ru—I-(MeO-SEGPHOS)](CO$_3$)
[Ru—I-(p-Cl-SEGPHOS)](OMs)
[Ru—I-(p-Cl-SEGPHOS)](OTs)
[Ru—I-(p-Cl-SEGPHOS)](OTf)
[Ru—I-(p-Cl-SEGPHOS)]{OS(O)$_2$C$_4$F$_9$}
[Ru—I-(p-Cl-SEGPHOS)](BF$_4$)
[Ru—I-(p-Cl-SEGPHOS)](PF$_6$)
[Ru—I-(p-Cl-SEGPHOS)](ClO$_4$)
[Ru—I-(p-Cl-SEGPHOS)](BPh$_4$)
[Ru—I-(p-Cl-SEGPHOS)](SO$_4$)
[Ru—I-(p-Cl-SEGPHOS)](CO$_3$)
[Ru—I-(Naph-SEGPHOS)](OMs)
[Ru—I-(Naph-SEGPHOS)](OTs)
[Ru—I-(Naph-SEGPHOS)](OTf)
[Ru—I-(Naph-SEGPHOS)]{OS(O)$_2$C$_4$F$_9$}
[Ru—I-(Naph-SEGPHOS)](BF$_4$)
[Ru—I-(Naph-SEGPHOS)](PF$_6$)
[Ru—I-(Naph-SEGPHOS)](ClO$_4$)
[Ru—I-(Naph-SEGPHOS)](BPh$_4$)
[Ru—I-(Naph-SEGPHOS)](SO$_4$)
[Ru—I-(Naph-SEGPHOS)](CO$_3$)
[Ru—I-(cpSEGPHOS)](OMs)
[Ru—I-(cpSEGPHOS)](OTs)
[Ru—I-(cpSEGPHOS)](OTf)
[Ru—I-(cpSEGPHOS)]{OS(O)$_2$C$_4$F$_9$}
[Ru—I-(cpSEGPHOS)](BF$_4$)
[Ru—I-(cpSEGPHOS)](PF$_6$)
[Ru—I-(cpSEGPHOS)](ClO$_4$)
[Ru—I-(cpSEGPHOS)](BPh$_4$)
[Ru—I-(cpSEGPHOS)](SO$_4$)
[Ru—I-(cpSEGPHOS)](CO$_3$)
[Ru—I-(CySEGPHOS)](OMs)
[Ru—I-(CySEGPHOS)](OTs)
[Ru—I-(CySEGPHOS)](OTf)
[Ru—I-(CySEGPHOS)]{OS(O)$_2$C$_4$F$_9$}
[Ru—I-(CySEGPHOS)](BF$_4$)
[Ru—I-(CySEGPHOS)](PF$_6$)
[Ru—I-(CySEGPHOS)](ClO4)
[Ru—I-(CySEGPHOS)](BPh$_4$)
[Ru—I-(CySEGPHOS)](SO$_4$)
[Ru—I-(CySEGPHOS)](CO$_3$)
[Ru—I-(SEGPHOS)]{OS(O)$_2$C$_8$F$_{17}$}
[Ru—I—(T-SEGPHOS)]{OS(O)$_2$C$_8$F$_{17}$}

[Ru—I-(tBu-SEGPHOS)]{OS(O)$_2$C$_8$F$_{17}$}
[Ru—I-(m-T-SEGPHOS OS)]{OS(O)$_2$C$_8$F$_{17}$}
[Ru—I-(DM-SEGPHOS)]{OS(O)$_2$C$_8$F$_{17}$}
[Ru—I-(DtBu-SEGPHOS)]{OS(O)$_2$C$_8$F$_{17}$}
[Ru—I-(MeO-SEGPHOS)]{OS(O)$_2$C$_8$F$_{17}$}
[Ru—I-(p-Cl-SEGPHOS)]{OS(O)$_2$C$_8$F$_{17}$}
[Ru—I-(cpSEGPHOS)]{OS(O)$_2$C$_8$F$_{17}$}
[Ru—I-(CySEGPHOS)]{OS(O)$_2$C$_8$F$_{17}$}
[Ru(I)$_{1.5}$(SEGPHOS)]$_2$(OMs)
[Ru(I)$_{1.5}$(SEGPHOS)]$_2$(OTs)
[Ru(I)$_{1.5}$(SEGPHOS)]$_2$(OTf)
[Ru(I)$_{1.5}$(SEGPHOS)]$_2${OS(O)$_2$C$_4$F$_9$}
[Ru(I)$_{1.5}$(SEGPHOS)]$_2$(BF$_4$)
[Ru(I)$_{1.5}$(SEGPHOS)]$_2$(PF$_6$)
[Ru(I)$_{1.5}$(SEGPHOS)]$_2$(ClO$_4$)
[Ru(I)$_{1.5}$(SEGPHOS)]$_2$(BPh$_4$)
[Ru(I)$_{1.5}$(T-SEGPHOS)]$_2$(OMs)
[Ru(I)$_{1.5}$(T-SEGPHOS)]$_2$(OTs)
[Ru(I)$_{1.5}$(T-SEGPHOS)]$_2$(OTf)
[Ru(I)$_{1.5}$(T-SEGPHOS)]$_2${OS(O)$_2$C$_4$F$_9$}
[Ru(I)$_{1.5}$(T-SEGPHOS)]$_2$(BF$_4$)
[Ru(I)$_{1.5}$(T-SEGPHOS)]$_2$(PF$_6$)
[Ru(I)$_{1.5}$(T-SEGPHOS)]$_2$(ClO$_4$)
[Ru(I)$_{1.5}$(T-SEGPHOS)]$_2$(BPh$_4$)
[Ru(I)$_{1.5}$(tBu-SEGPHOS)]$_2$(OMs)
[Ru(I)$_{1.5}$(tBu-SEGPHOS)]$_2$(OTs)
[Ru(I)$_{1.5}$(tBu-SEGPHOS)]$_2$(OTf)
[Ru(I)$_{1.5}$(tBu-SEGPHOS)]$_2${OS(O)$_2$C$_4$F$_9$}
[Ru(I)$_{1.5}$(tBu-SEGPHOS)]$_2$(BF$_4$)
[Ru(I)$_{1.5}$(tBu-SEGPHOS)]$_2$(PF$_6$)
[Ru(I)$_{1.5}$(tBu-SEGPHOS)]$_2$(ClO$_4$)
[Ru(I)$_{1.5}$(tBu-SEGPHOS)]$_2$(BPh$_4$)
[Ru(I)$_{1.5}$(m-T-SEGPHOS)]$_2$(OMs)
[Ru(I)$_{1.5}$(m-T-SEGPHOS)]$_2$(OTs)
[Ru(I)$_{1.5}$(m-T-SEGPHOS)]$_2$(OTf)
[Ru(I)$_{1.5}$(m-T-SEGPHOS)]$_2${OS(O)$_2$C$_4$F$_9$}
[Ru(I)$_{1.5}$(m-T-SEGPHOS)]$_2$(BF$_4$)
[Ru(I)$_{1.5}$(m-T-SEGPHOS)]$_2$(PF$_6$)
[Ru(I)$_{1.5}$(m-T-SEGPHOS)]$_2$(ClO$_4$)
[Ru(I)$_{1.5}$(m-T-SEGPHOS)]$_2$(BPh$_4$)
[Ru(I)$_{1.5}$(DM-SEGPHOS)]$_2$(OMs)
[Ru(I)$_{1.5}$(DM-SEGPHOS)]$_2$(OTs)
[Ru(I)$_{1.5}$(DM-SEGPHOS)]$_2$(OTf)
[Ru(I)$_{1.5}$(DM-SEGPHOS)]$_2${OS(O)$_2$C$_4$F$_9$}
[Ru(I)$_{1.5}$(DM-SEGPHOS)]$_2$(BF$_4$)
[Ru(I)$_{1.5}$(DM-SEGPHOS)]$_2$(PF$_6$)
[Ru(I)$_{1.5}$(DM-SEGPHOS)]$_2$(ClO$_4$)
[Ru(I)$_{1.5}$(DM-SEGPHOS)]$_2$(BPh$_4$)
[Ru(I)$_{1.5}$(DtBu-SEGPHOS)]$_2$(OMs)
[Ru(I)$_{1.5}$(DtBu-SEGPHOS)]$_2$(OTs)
[Ru(I)$_{1.5}$(DtBu-SEGPHOS)]$_2$(OTf)
[Ru(I)$_{1.5}$(DtBu-SEGPHOS)]$_2${OS(O)$_2$C$_4$F$_9$}
[Ru(I)$_{1.5}$(DtBu-SEGPHOS)]$_2$(BF$_4$)
[Ru(I)$_{1.5}$(DtBu-SEGPHOS)]$_2$(PF$_6$)
[Ru(I)$_{1.5}$(DtBu-SEGPHOS)]$_2$(ClO$_4$)
[Ru(I)$_{1.5}$(DtBu-SEGPHOS)]$_2$(BPh$_4$)
[Ru(I)$_{1.5}$(MeO-SEGPHOS)]$_2$(OMs)
[Ru(I)$_{1.5}$(MeO-SEGPHOS)]$_2$(OTs)
[Ru(I)$_{1.5}$(MeO-SEGPHOS)]$_2$(OTf)
[Ru(I)$_{1.5}$(MeO-SEGPHOS)]$_2${OS(O)$_2$C$_4$F$_9$}
[Ru(I)$_{1.5}$(MeO-SEGPHOS)]$_2$(BF$_4$)
[Ru(I)$_{1.5}$(MeO-SEGPHOS)]$_2$(PF$_6$)
[Ru(I)$_{1.5}$(MeO-SEGPHOS)]$_2$(ClO$_4$)
[Ru(I)$_{1.5}$(MeO-SEGPHOS)]$_2$(BPh$_4$)
[Ru(I)$_{1.5}$(p-Cl-SEGPHOS)]$_2$(OMs)
[Ru(I)$_{1.5}$(p-Cl-SEGPHOS)]$_2$(OTs)
[Ru(I)$_{1.5}$(p-Cl-SEGPHOS)]$_2$(OTf)
[Ru(I)$_{1.5}$(p-Cl-SEGPHOS)]$_2${OS(O)$_2$C$_4$F$_9$}
[Ru(I)$_{1.5}$(p-Cl-SEGPHOS)]$_2$(BF$_4$)
[Ru(I)$_{1.5}$(p-Cl-SEGPHOS)]$_2$(PF$_6$)
[RuI(HCOO)(BIPHEP)]$_2$
[RuI(HCOO)(BICHEP)]$_2$
[RuI(HCOO)(MBIPHEP)]$_2$
[RuI(HCOO)(MBICHEP)]$_2$
[RuI(CH$_3$COO)(BIPHEP)]$_2$
[RuI(CH$_3$COO)(BICHEP)]$_2$
[RuI(CH$_3$COO)(MBIPHEP)]$_2$
[RuI(CH$_3$COO)(MBICHEP)]$_2$
[RuI(CH$_3$CH$_2$COO)(BIPHEP)]$_2$
[RuI(CH$_3$CH$_2$COO)(BICHEP)]$_2$
[RuI(CH$_3$CH$_2$COO)(MBIPHEP)]$_2$
[RuI(CH$_3$CH$_2$COO)(MBICHEP)]$_2$
[RuI(CH$_3$CH$_2$CH$_2$COO)(BIPHEP)]$_2$
[RuI(CH$_3$CH$_2$CH$_2$COO)(BICHEP)]$_2$
[RuI(CH$_3$CH$_2$CH$_2$COO)(MBIPHEP)]$_2$
[RuI(CH$_3$CH$_2$CH$_2$COO)(MBICHEP)]$_2$
[RuI(CH$_3$COCOO)(BIPHEP)]$_2$
[RuI(CH$_3$COCOO)(BICHEP)]$_2$
[RuI(CH$_3$COCOO)(MBIPHEP)]$_2$
[RuI(CH$_3$COCOO)(MBICHEP)]$_2$
[RuI(PhCOO)(BIPHEP)]$_2$
[RuI(PhCOO)(BICHEP)]$_2$
[RuI(PhCOO)(MBIPHEP)]$_2$
[RuI(PhCOO)(MBICHEP)]$_2$
[RuI(CF$_3$COO)(BIPHEP)]$_2$
[RuI(CF$_3$COO)(BICHEP)]$_2$
[RuI(CF$_3$COO)(MBIPHEP)]$_2$
[RuI(CF$_3$COO)(MBICHEP)]$_2$
[Ru—I-(BIPHEP)]$_2$(OMs)
[Ru—I-(BIPHEP)]$_2$(OTs)
[Ru—I-(BIPHEP)]$_2$(OTf)
[Ru—I-(BIPHEP)]$_2${OS(O)$_2$C$_4$F$_9$}
[Ru—I-(BIPHEP)]$_2${OS(O)$_2$C$_8$F$_{17}$}
[Ru—I-(BIPHEP)]$_2$(BF$_4$)
[Ru—I-(BIPHEP)]$_2$(PF$_6$)
[Ru—I-(BIPHEP)]$_2$(ClO$_4$)
[Ru—I-(BIPHEP)]$_2$(BPh$_4$)
[Ru—I-(BIPHEP)]$_2$(SO$_4$)
[Ru—I-(BIPHEP)]$_2$(CO$_3$)
[Ru(I)$_{1.5}$(BIPHEP)]$_2$(OMs)
[Ru(I)$_{1.5}$(BIPHEP)]$_2$(OTs)
[Ru(I)$_{1.5}$(BIPHEP)]$_2$(OTf)
[Ru(I)$_{1.5}$(BIPHEP)]$_2${OS(O)$_2$C$_4$F$_9$}
[Ru(I)$_{1.5}$(BIPHEP)]$_2$(BF$_4$)
[Ru(I)$_{1.5}$(BIPHEP)]$_2$(PF$_6$)
[Ru(I)$_{1.5}$(BIPHEP)]$_2$(ClO$_4$)
[Ru(I)$_{1.5}$(BIPHEP)]$_2$(BPh$_4$)
[Ru(I)$_{1.5}$(BIPHEP)]$_2${OS(O)$_2$C$_8$F$_{17}$}
[Ru—I-(BICHEP)]$_2$(OMs)
[Ru—I-(BICHEP)]$_2$(OTs)
[Ru—I-(BICHEP)]$_2$(OTf)
[Ru—I-(BICHEP)]$_2${OS(O)$_2$C$_4$F$_9$}
[Ru—I-(BICHEP)]$_2${OS(O)$_2$C$_8$F$_{17}$}
[Ru—I-(BICHEP)]$_2$(BF$_4$)
[Ru—I-(BICHEP)]$_2$(PF$_6$)
[Ru—I-(BICHEP)]$_2$(ClO$_4$)
[Ru—I-(BICHEP)]$_2$(BPh$_4$)
[Ru—I-(BICHEP)]$_2$(SO$_4$)
[Ru—I-(BICHEP)]$_2$(CO$_3$)
[Ru(I)$_{1.5}$(BICHEP)]$_2$(OMs)
[Ru(I)$_{1.5}$(BICHEP)]$_2$(OTs)
[Ru(I)$_{1.5}$(BICHEP)]$_2$(OTf)
[Ru(I)$_{1.5}$(BICHEP)]$_2${OS(O)$_2$C$_4$F$_9$}
[Ru(I)$_{1.5}$(BICHEP)]$_2$(BF$_4$)

[Ru(I)$_{1.5}$(BICHEP)]$_2$(PF$_6$)
[Ru(I)$_{1.5}$(BICHEP)]$_2$(ClO$_4$)
[Ru(I)$_{1.5}$(BICHEP)]$_2$(BPh$_4$)
[Ru(I)$_{1.5}$(BICHEP)]$_2${OS(O)$_2$C$_8$F$_{17}$}
[Ru—I-(MBIPHEP)]$_2$(OMs)
[Ru—I-(MBIPHEP)]$_2$(OTs)
[Ru—I-(MBIPHEP)]$_2$(OTf)
[Ru—I-(MBIPHEP)]$_2${OS(O)$_2$C$_4$F$_9$}
[Ru—I-(MBIPHEP)]$_2${OS(O)$_2$C$_8$F$_{17}$}
[Ru—I-(MBIPHEP)]$_2$(BF$_4$)
[Ru—I-(MBIPHEP)]$_2$(PF$_6$)
[Ru—I-(MBIPHEP)]$_2$(ClO$_4$)
[Ru—I-(MBIPHEP)]$_2$(BPh$_4$)
[Ru—I-(MBIPHEP)](SO$_4$)
[Ru—I-(MBIPHEP)](CO$_3$)
[Ru(I)$_{1.5}$(MBIPHEP)]$_2$(OMs)
[Ru(I)$_{1.5}$(MBIPHEP)]$_2$(OTs)
[Ru(I)$_{1.5}$(MBIPHEP)]$_2$(OTf)
[Ru(I)$_{1.5}$(MBIPHEP)]$_2${OS(O)$_2$C$_4$F$_9$}
[Ru(I)$_{1.5}$(MBIPHEP)]$_2$(BF$_4$)
[Ru(I)$_{1.5}$(MBIPHEP)]$_2$(PF$_6$)
[Ru(I)$_{1.5}$(MBIPHEP)]$_2$(ClO$_4$)
[Ru(I)$_{1.5}$(MBIPHEP)]$_2$(BPh$_4$)
[Ru(I)$_{1.5}$(MBIPHEP)]$_2${OS(O)$_2$C$_8$F$_{17}$}
[Ru—I-(MBICHEP)]$_2$(OMs)
[Ru—I-(MBICHEP)]$_2$(OTs)
[Ru—I-(MBICHEP)]$_2$(OTf)
[Ru—I-(MBICHEP)]$_2${OS(O)$_2$C$_4$F$_9$}
[Ru—I-(MBICHEP)]$_2${OS(O)$_2$C$_8$F$_{17}$}
[Ru—I-(MBICHEP)]$_2$(BF$_4$)
[Ru—I-(MBICHEP)]$_2$(PF$_6$)
[Ru—I-(MBICHEP)]$_2$(ClO$_4$)
[Ru—I-(MBICHEP)]$_2$(BPh$_4$)
[Ru—I-(MBICHEP)]$_2$(SO$_4$)
[Ru—I-(MBICHEP)]$_2$(CO$_3$)
[Ru(I)$_{1.5}$(MBICHEP)]$_2$(OMs)
[Ru(I)$_{1.5}$(MBICHEP)]$_2$(OTs)
[Ru(I)$_{1.5}$(MBICHEP)]$_2$(OTf)
[Ru(I)$_{1.5}$(MBICHEP)]$_2${OS(O)$_2$C$_4$F$_9$}
[Ru(I)$_{1.5}$(MBICHEP)]$_2$(BF$_4$)
[Ru(I)$_{1.5}$(MBICHEP)]$_2$(PF$_6$)
[Ru(I)$_{1.5}$(MBICHEP)]$_2$(ClO$_4$)
[Ru(I)$_{1.5}$(MBICHEP)]$_2$(BPh$_4$)
[Ru(I)$_{1.5}$(MBICHEP)]$_2${OS(O)$_2$C$_8$F$_{17}$}

In the second aspect of the invention, examples of the salts Me(anion)f represented by the formula (15) which are the raw materials for producing [RuI$_a$(R$^1$-SEGPHOS)(sol)$_b$](I)$_c$(anion)$_d$ from the ruthenium complexes represented by the formulae (11) and (6) may include the following compounds.

(a) Lithium trifluoromethane sulfonate (lithium triflate) (hereinafter abbreviated as "LiOTf"), sodium trifluoromethane sulfonate (Sodium triflate) (hereinafter abbreviated as "NaOTf"), potassium trifluoromethane sulfonate (potassium triflate) (hereinafter abbreviated as "KOTf"), Mg(OTf)$_2$, Al(OTf)$_3$, AgOTf and NH$_4$OTf.

(b) Lithium nonafluorobutane sulfonate (hereinafter abbreviated as "LiONf"), sodium nonafluorobutane sulfonate (hereinafter abbreviated as "NaONf") and potassium nonafluorobutane sulfonate (hereinafter abbreviated as "KONf").

(c) Lithium heptadecafluorooctane sulfonate (hereinafter abbreviated as "LiOhepDf"), sodium heptadecafluorooctane sulfonate (hereinafter abbreviated as "NaOhepDf") and potassium heptadecafluorooctane sulfonate (hereinafter abbreviated as "KOhepDf").

(d) Sodium undecafluorocyclohexane sulfonate (hereinafter abbreviated as "NaOuDCyf") and potassium undecafluorocyclohexane sulfonate (hereinafter abbreviated as "KOuDCyf").

The amount of each of these salts is preferably in a range between about 0.25 to 2 equivalents by mol and more preferably about 0.5 to 1 equivalent by mol based on one mol of the ruthenium complex (11) or (6). Given as examples of the nitrile type solvent used in the reaction formulae 1 and 2 are acetonitrile, benzonitrile and an acetonitrile/benzonitrile mixed solvent.

The temperature at which [RuI$_a$(R$^1$-SEGPHOS)(sol)$_b$](I)$_c$(anion)$_d$ of the present invention is produced according to the methods 1 and 2 is about 60 to 90° C. and preferably 70 to 80° C. The reaction time is about 10 to 40 hours and particularly preferably about 15 to 20 hours. After the reaction is completed, the hydrophobic organic solvent layer is taken out. The solvent is refined by, for instance, distillation and drying, thereby obtaining the objective complex mixture represented by [RuI$_a$(R$^1$-SEGPHOS)(sol)$_b$](I)$_c$(anion)$_d$ (where a, b, c and d respectively denote numerals comprising a combination of a=0, b=4, c=2 and d=0, a combination of a=0, b=4, c=1 and d=1 and a combination of a=1, b=3, c=0 and d=1).

[RuI$_a$(R$^1$-SEGPHOS)(sol)$_b$](I)$_c$(anion)$_d$ obtained in this manner is a complex having a structure in which the arene molecule of the compounds (11) and (6) is removed and the nitrile-type solvent coordinates. Alternatively, it is a mixture of complexes having a structure in which part or all of the iodine atoms are substituted with perfluoroalkylsulfonyl anions. The obtained mixture of complexes can be indicated by the formula comprising ruthenium, iodine, perfluoroalkylsulfonyl anions and optically active tertiary phosphine. Specific examples of the complex mixture include compounds having the structures corresponding to [Ru(R$^1$-SEGPHOS)(SOL)$_4$]I$_2$, [Ru(R$^1$-SEGPHOS)(SOL)$_4$]I(anion) and [RuI(R$^1$-SEGPHOS)(SOL)$_3$](anion) of the formulae (16) to (18) shown in FIG. 1, and [Ru(R$^1$-SEGPHOS)(sol)$_4$](anion)$_2$. These complexes are obtained as either (R) isomer or (S) isomer corresponding to the absolute configuration of R$^1$-SEGPHOS (9) to be used. However, the notation of these isomers is omitted.

R$^1$-SEGPHOS in the formulae (16) and (18) is the aforementioned SEGPHOS, T-SEGPHOS, tBu-SEGPHOS, m-T-SEGPHOS, DM-SEGPHOS, DtBu-SEGPHOS, MeO-SEGPHOS, p-Cl-SEGPHOS, Naph-SEGPHOS, cpSEGPHOS or CySEGPHOS. SOL is acetonitrile (CH$_3$CN) or benzonitrile (PhCN). Anion is the aforementioned OTf, ONf, OhepDf or OuDCyf. The complex [Ru(R$^1$-SEGPHOS)(SOL)$_4$](anion)$_2$ is not an iodo-complex, so that it has a poor activity, it is therefore preferable to decrease the production of [Ru(R$^1$-SEGPHOS)(SOL)$_4$](anion)$_2$. However, the contamination of this product causes no harm. Consequently, the iodo-complex mixture of the present invention may be used as it is prepared, without further separation or purification.

[Ru—(I)$_q$—(T1)$_n$(L)]$_m$(T$^2$)$_p$ of the formula (1) (first aspect of the invention) or the complex mixture [RuI$_a$(R$^1$-SEGPHOS)(SOL)$_b$](I)$_c$(anion)$_d$ (second aspect of the invention) obtained in this manner is a compound which has a remarkably high catalytic activity and can be widely used as an asymmetrically synthesizing catalyst. When this compound is used as a catalyst for an asymmetric hydrogenation reaction of 4-methylene-2-oxetanone, optically active 4-methyl-2-oxetanone of high optical purity can be produced efficiently in a short time.

Optically active 4-methyl-2-oxetanone may be produced by using either [Ru—(I)$_q$—(T$^1$)$_n$(L)]$_m$(T$^2$)$_p$ of the formula (1) or the complex mixture $[RuI_a(R^1\text{-SEGPHOS})(SOL)_b](I)_c(\text{anion})_d$ as follows: either $[RuI(RCOO)(R^1\text{-BINAP})]_2$, a specific example of the formula (1), or $[RuI_a(R^1\text{-SEGPHOS})(SOL)_b](I)_c(\text{anion})_d$, another specific example of the formula (1), and 4-methylene-2-oxetanone (raw material compound) and a solvent are charged into a pressure container in nitrogen atmosphere, and the mixture obtained is asymmetrically hydrogenated under a hydrogen pressure of 5 to 150 kg/cm$^2$, preferably at a temperature ranging from room temperature up to 100° C. In the above method, 4-Methylene-2-oxetanone used as the raw material compound can be easily synthesized subsequent to the heat decomposition of acetic acid or acetic anhydride according to the method reported by R. J. Clemens et al., (Chem. Rev., Vol. 86, pp. 241–318 (1986)).

In $[RuI(RCOO)(R^1\text{-BINAP})]_2$ or $[RuI_a(R^1\text{-SEGPHOS})(SOL)_b](I)_c(\text{anion})_d$ used as the asymmetric hydrogenation catalyst, (R) isomer or (S) isomer thereof is selected depending on which of the absolute configurations of 4-methyl-2-oxetanone is desired.

In order to produce optically active 4-methyl-2-oxetanone efficiently, the catalyst $[RuI(RCOO)(R^1\text{-BINAP})]_2$ or $[RuI_a(R^1\text{-SEGPHOS})(sol)_b](I)_c(\text{anion})_d$ is prepared, such that the molar ratio of metal ruthenium to optically active phosphine ranges from 1:1.05 to 1:0.95. When the optically active complex represented by the formula (3) or (11) is prepared, the optically active phosphine ligand is generally used in an amount of about 1.05 to 1.2 equivalents per equivalent of ruthenium. In this case, if the amount of the phosphine ligand is limited to 1.05 equivalents or less, a side reaction, that is, a polymerization reaction of 4-methylene-2-oxetanone can be avoided. On the other hand, when the amount of the optically active phosphine ligand is 0.95 equivalents or less, the amount of metal ruthenium used becomes excessive, which is economically disadvantageous.

In the case of $[RuI(RCOO)(R^1\text{-BINAP})]_2$ (first aspect of the invention), the amount used as a catalyst is generally in a range between about 0.0001 and 0.01 mols and particularly preferably about 0.0002 and 0.0005 mols based on one mol of 4-methylene-2-oxetanone. When the amount of the catalyst is less than 0.0001 mols, only insufficient catalytic effect is obtained, whereas use of an amount exceeding 0.0005 mols is not economically advantageous.

In the case of $[RuI_a(R^1\text{-SEGPHOS})(sol)_b](I)_c(\text{anion})_d$ (second aspect of the invention), the amount used as a catalyst is generally in a range between about 1/30000 and 1/2000 mols, and particularly preferably about 1/20000 and 1/10000 mols based on one mol of 4-methylene-2-oxetanone. When the amount of the catalyst is less than 1/30000 mols, only insufficient catalytic effect is obtained, whereas use of an amount exceeding 1/2000 mols is not economically advantageous.

In both aspects of the invention, no particular limitation is imposed on the solvent insofar as it can be used in usual asymmetric hydrogenation. Specific examples of the solvent may include linear or cyclic ethers such as diethyl ether, tetrahydrofuran and dioxane; organic halides such as methylene chloride, methylene bromide and dichloroethane; ketones such as acetone, methyl ethyl ketone and methyl butyl ketone; carboxylic acids such as acetic acid and propionic acid; esters such as ethyl acetate, butyl acetate and methyl 3-hydroxybutyric acid; aromatic compounds such as toluene and benzene and alcohols such as methanol, ethanol, isopropanol, tert-butyl alcohol and 1,3-butane diol and mixed solvents of these solvents. About 1% of water may be further added to the above solvent to raise the rate of asymmetric hydrogenation reaction.

The reaction temperature and reaction time in the asymmetric hydrogenation reaction differ depending on the types of catalyst and other reaction condition. The reaction is generally effected at temperatures ranging from room temperature to 100° C. and preferably about 30 to 60° C. for 0.5 to 40 hours. The hydrogenation pressure is in a range between about 5 to 150 kg/cm$^2$ and preferably about 20 to 100 kg/cm$^2$. After the reaction, the reaction product is refined by removal of the solvent or distillation, whereby the objective optically active 4-methyl-2-oxetanone having a high optical purity can be obtained efficiently in a short time span.

The other catalysts mentioned in the present description can work out the same results in the manner as those specifically exemplified above.

The present invention will be explained in detail by way of examples which are not intended to be limiting of the present invention.

The following results will show that, when the ruthenium-iodo-optically active phosphine complex $[\text{Ru}—(I)_q—(T^1)\text{n}(L)]_m(T^2)_p$ or $[RuI_a(R^1\text{-SEGPHOS})(SOL)_b](I)_c(\text{anion})_d$ of the present invention is used as a catalyst, the reaction catalyzed proceeds at a remarkably higher reaction rate than when a conventional ruthenium-optically active phosphine complex is used. Further, the products obtained according to the present invention have a higher optical purity.

Further, such ruthenium-iodo-optically active phosphine complexes can easily be produced according to the methods described in the present invention.

Moreover, the ruthenium-iodo-optically active phosphine complexes of the invention can achieve a high asymmetric activity in asymmetric reactions, and a product of high optical purity can be obtained. Therefore, the phosphine complex of the present invention can be used widely as a catalyst for asymmetric syntheses and bring in a number of economical advantages. Particularly, when it is used as a catalyst for the asymmetric hydrogenation reaction of 4-methylene-2-oxetanone, optically active 4-methyl-2-oxetanone having a high optical purity can be produced efficiently in a short time span. This optically active 4-methyl-2-oxetanone is supplied as a useful raw material for polymer production.

Although the invention has been described with reference to particular products, materials and embodiments, it is to be understood that the invention is not limited to the particulars disclosed and extends to all aquivalents within the scope of the claims.

The present disclosure relates to subject matter contained in priority Japanese Applications Nos. HEI-10-142233 and HEI-11-093644, filed on May 8, 1998 and Mar. 31, 1999, respectively, which are herein expressly incorporated by reference in their entireties.

Examples of the First Aspect of the Invention

In the following examples, the properties of the compounds prepared in examples were measured using the following instruments.

$^{31}$P NMR spectrum: AM-400 model equipment (manufactured by Bruker)

External standard material: 85% phosphoric acid Solvent: chloroform (Measurement of Optical Purity)

Gas chromatograph equipment: HEWLETT PACKARD 5890 SERIES II

Optically active column (Chraldex G-TA 30m (manufactured by ASTEC)

EXAMPLE 1

Production of $[RuI(CH_3COO)((S)—T\text{-BINAP})]_2$

An 80 ml Schlenk's tube was, after the air in the tube was replaced by nitrogen, charged with 1.0 g (1.02 mmol) of

[RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.172 g (2.09 mmol) of sodium acetate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.9 g (yield: 96.4%) of the titled compound.

$^{31}$P NMR spectrum: 20.5(d, J=45 Hz), 74.6(d, J=46 Hz)

EXAMPLE 2

Production of [RuI(CH$_3$COO)((S)—T-BINAP)]$_2$

A 200 ml reaction container was, after the air in the container was replaced by nitrogen, charged with 2.7 g (2.31 mmol) of [RuI(p-cymene)((S)—T-BINAP)]I and 110 ml of methanol, and the mixture was stirred at 55° C. for 16 hours. The mixture was cooled to room temperature, and methanol was withdrawn. Then, under the nitrogen atmosphere, 0.199 g (2.42 mmol) of sodium acetate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.2 g (yield: 98.6%) of the titled compound.

EXAMPLE 3

Production of [RuI(CH$_3$COO)((S)—T-BINAP)]$_2$

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP, 0.172 g (2.09 mmol) of sodium acetate and 40 ml of methanol, and the mixture was stirred at 55° C. for 16 hours. The mixture was cooled to room temperature, and methanol was withdrawn. Then, under the nitrogen atmosphere, 20 ml of methylene chloride and 20 ml of deaerated water were added to the resulting mixture, followed by stirring for 10 minutes. The methylene chloride layer was extracted into a sampling syringe and washed with 20 ml of deaerated water, followed by distilling methylene chloride under reduced pressure. The resulting complex was then dried at room temperature under reduced pressure for 4 hours, to obtain 1.9 g (yield: 96.4%) of the titled compound.

EXAMPLE 4

Production of [RuI(CH$_3$COO)((S)—T-BINAP)]$_2$

A 200 ml reaction container was, after the air in the container was replaced by nitrogen, charged with 2.7 g (2.31 mmol) of [RuI(p-cymene)((S)—T-BINAP)]I, 0.199 g (2.42 mmol) of sodium acetate and 110 ml of methanol, and the mixture was stirred at 55° C. for 16 hours. The mixture was cooled to room temperature, and methanol was withdrawn. Then, under the nitrogen atmosphere, 20 ml of methylene chloride and 20 ml of deaerated water were added to the resulting mixture, followed by stirring for 30 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.2 g (yield: 98.6%) of the titled compound.

EXAMPLE 5

Production of [RuI(CH$_3$CH$_2$COO)((S)—T-BINAP)]$_2$

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.2 g (2.08 mmol) of sodium propionate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.9 g (yield: 95.0%) of the titled compound.

$^{31}$P-NMR spectrum: 20.5(d, J=43 Hz), 73.9(d, J=43 Hz)

EXAMPLE 6

Production of [RuI(PhCOO)((S)—T-BINAP)]$_2$

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.301 g (2.09 mmol) of sodium benzoate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.0 g (yield: 95.4%) of the titled compound.

$^{31}$P NMR spectrum: 21. 1(d, J=44 Hz), 74.2(d, J=44 Hz)

EXAMPLE 7

Production of [RuI(CF$_3$COO)((S)—T-BINAP)]$_2$

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 1.11 g (8.16 mmol) of sodium trifluoroacetate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The

EXAMPLE 8

Production of [RuI(CH$_3$COCOO)((S)—T-BINAP)]$_2$

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.228 g (2.07 mmol) of sodium pyruvate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.9 g (yield: 93.7%) of the titled compound.

$^{31}$P-NMR spectrum: 21.5 (d, J=44 Hz), 72.8 (d, J=44 Hz)

EXAMPLE 9

Production of [RuI(CH$_3$COO)((S)-BINAP)]$_2$

An 80 ml Schlenk's tube was, after the air in the tube was replaced by nitrogen, charged with 1.0 g (1.02 mmol) of [RuI$_2$(p-cymene)]$_2$, 1.28 g (2.06 mmol) of (S)-BINAP and 40 ml of methanol, and the mixture was stirred at 55° C. for 16 hours. The mixture was cooled to room temperature, and methanol was withdrawn. Then, under the nitrogen atmosphere, 0.172 g (2.09 mmol) of sodium acetate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.8 g (yield: 97.0%) of the titled compound.

EXAMPLE 10

Production of [RuI(CH$_3$COO)((S)-tBu-BINAP)]$_2$

An 80 ml Schlenk's tube was, after the air in the tube was replaced by nitrogen, charged with 1.0 g (1.02 mmol) of [RuI$_2$(p-cymene)]$_2$, 1.75 g (2.06 mmol) of (S)-tBu-BINAP and 40 ml of methanol, and the mixture was stirred at 55° C. for 16 hours. The mixture was cooled to room temperature, and methanol was withdrawn. Then, under the nitrogen atmosphere, 0.172 g (2.09 mmol) of sodium acetate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 40° C. under reduced pressure for 4 hours, to obtain 2.2 g (yield: 95.1%) of the titled compound.

EXAMPLE 11

Production of [RuI(CH$_3$COO)((S)-DM-BINAP)]$_2$

An 80 ml Schlenk's tube was, after the air in the tube was replaced by nitrogen, charged with 1.0 g (1.02 mmol) of [RuI$_2$(p-cymene)]$_2$, 1.52 g (2.07 mmol) of (S)-DM-BINAP and 40 ml of methanol, and the mixture was stirred at 55° C. for 16 hours. The mixture was cooled to room temperature, and methanol was withdrawn. Then, under the nitrogen atmosphere, 0.172 g (2.09 mmol) of sodium acetate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.0 g (yield: 95.9%) of the titled compound.

EXAMPLE 12

Production of (R)-4-methyl-2-oxetanone

A stainless autoclave with a volume of 500 ml was charged with 76.65 mg (0.0794 mmol) of [RuI(CH$_3$COO)((S)-BINAP)]$_2$, 20.1 g (239.3 mmol) of 4-methylene-2-oxetanone, 80 ml of tetrahydrofuran and 0.45 ml of deaerated water under nitrogen, and the mixture was stirred at a reaction temperature of 50° C. under a hydrogen pressure of 50 kg/cm2 for 15 hours. The resulting reaction solution was distilled using a Claisen tube distiller, to obtain 18.0 g (yield: 87.5%) of a fraction having a boiling point of 71–73° C./29 mmHg (3866 Pa). The conversion rate of this reaction was 87.5% and the turn-over number measured to evaluate the catalytic activity was 2630. A gas chromatography analysis by comparison to a standard material confirmed that the resulting product was 4-methyl-2-oxetanone. In order to determine the absolute configuration of the resultant product, the product was subjected to a gas chromatography (GC) analysis using an optically active column (Chiraldex G-TA 30 m, manufactured by ASTEC). The result of the analysis showed that the resultant product was an (R) isomer and the optical purity was 94.3% e.e.

EXAMPLE 13

Production of (R)-4-methyl-2-oxetanone

The same procedures as in Example 12 were carried out, except that 81.58 mg (0.0794 mmol) of [RuI(PhCOO)((S)—T-BINAP)]$_2$ and 20.69 g (246.31 mmol) of 4-methylene-2-oxetanone were used, to obtain 17.0 g (yield: 80.3%) of the titled compound. The conversion rate of this reaction was 80.1% and the turn-over number measured to evaluate the catalytic activity was 2480. The measurement of the absolute configuration showed that the resulting product was an (R) isomer and the optical purity was 95.3% e.e.

EXAMPLE 14

Production of (R)-4-methyl-2-oxetanone

The same procedures as in Example 12 were carried out, except that 77.76 mg (0.0794 mmol) of [RuI(CH$_3$CH$_2$COO)((S)—T-BINAP)]$_2$ and 20.37 g (242.5 mmol) of 4-methylene-2-oxetanone were used, to obtain 15.6 g (yield: 74.8%) of the titled compound. The conversion rate of this reaction was 74.97% and the turn-over number measured to evaluate the catalytic activity was 2290. The measurement of the absolute configuration showed that the resulting product was an (R) isomer and the optical purity was 94.9% e.e.

EXAMPLE 15

Production of (R)-4-methyl-2-oxetanone

The same procedures as in Example 12 were carried out, except that 47.32 mg (0.0476 mmol) of [RuI(CH$_3$COCOO)

((S)—T-BINAP)]$_2$ and 20.42 g (243.1 mmol) of 4-methylene-2-oxetanone were used, to obtain 10.6 g (yield: 50.7%) of the titled compound. The conversion rate of this reaction was 50.73% and the turn-over number measured to evaluate the catalytic activity was 2590. The measurement of the absolute configuration showed that the resulting product was an (R) isomer and the optical purity was 94.3% e.e.

EXAMPLE 16

Production of (R)-4-methyl-2-oxetanone

The same procedures as in Example 12 were carried out, except that 68.42 mg (0.068 mmol) of [RuI(CF$_3$COO)((S)—T-BINAP)]$_2$ and 20.0 g (238.1 mmol) of 4-methylene-2-oxetanone were used, to obtain 15.3 g (yield: 74.7%) of the titled compound. The conversion rate of this reaction was 75.0% and the turn-over number measured to evaluate the catalytic activity was 2630. The measurement of the absolute configuration showed that the resulting product was an (R) isomer and the optical purity was 94.0% e.e.

EXAMPLE 17

Production of (R)-4-methyl-2-oxetanone

The same procedures as in Example 12 were carried out, except that 61.81 mg (0.068 mmol) of [RuI(CH$_3$COO)((S)-BINAP)]$_2$ and 20.27 g (241.3 mmol) of 4-methylene-2-oxetanone were used, to obtain 14.5 g (yield: 69.9%) of the titled compound. The conversion rate of this reaction was 69.9% and the turn-over number measured to evaluate the catalytic activity was 2480. The measurement of the absolute configuration showed that the resulting product was an (R) isomer and the optical purity was 94.0% e.e.

EXAMPLE 18

Production of (R)-4-methyl-2-oxetanone

The same procedures as in Example 12 were carried out, except that 77.12 mg (0.068 mmol) of [RuI(CH$_3$COO)((S)-tBu-BINAP)]$_2$ and 20.5 g (244.0 mmol) of 4-methylene-2-oxetanone were used, to obtain 14.6 g (yield: 69.5%) of the titled compound. The conversion rate of this reaction was 69.7% and the turn-over number measured to evaluate the catalytic activity was 2500. The measurement of the absolute configuration showed that the resulting product was an (R) isomer and the optical purity was 94.1% e.e.

EXAMPLE 19

Production of (R)-4-methyl-2-oxetanone

The same procedures as in Example 12 were carried out, except that 69.5 mg (0.068 mmol) of [RuI(CH$_3$COO)((S)-DM-BINAP)]$_2$ and 20.0 g (238.1 mmol) of 4-methylene-2-oxetanone were used, to obtain 15.2 g (yield: 74.2%) of the titled compound. The conversion rate of this reaction was 74.2% and the turn-over number measured to evaluate the catalytic activity was 2600. The measurement of the absolute configuration showed that the resulting product was an (R) isomer and the optical purity was 94.2% e.e.

EXAMPLE 20

Production of [Ru—I$_{1.5}$-{(S)—T-BINAP}]$_2$(OTf)

An 80 ml Schlenk's tube was, after the air in the tube was replaced by nitrogen, charged with 0.5 g (0.51 mmol) of [RuI$_2$(p-cymene)]$_2$, 0.7 g (1.03 mmol) of (S)—T-BINAP and 20 ml of methanol, and the mixture was stirred at 55° C. for 16 hours. The mixture was cooled to room temperature, and methanol was withdrawn. Then, under the nitrogen atmosphere, 88 ml (0.51 mmol) of NaOTf was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.05 g (yield: 97.5%) of the titled compound. The analysis of the resulting product is as follows:

$^{31}$P NMR spectrum: 1.8 (d, J=35 Hz), 4.6 (d, J=33 Hz), 75.0 (d, J=34 Hz), 76.4 (d, J=36 Hz)

Figure 2:
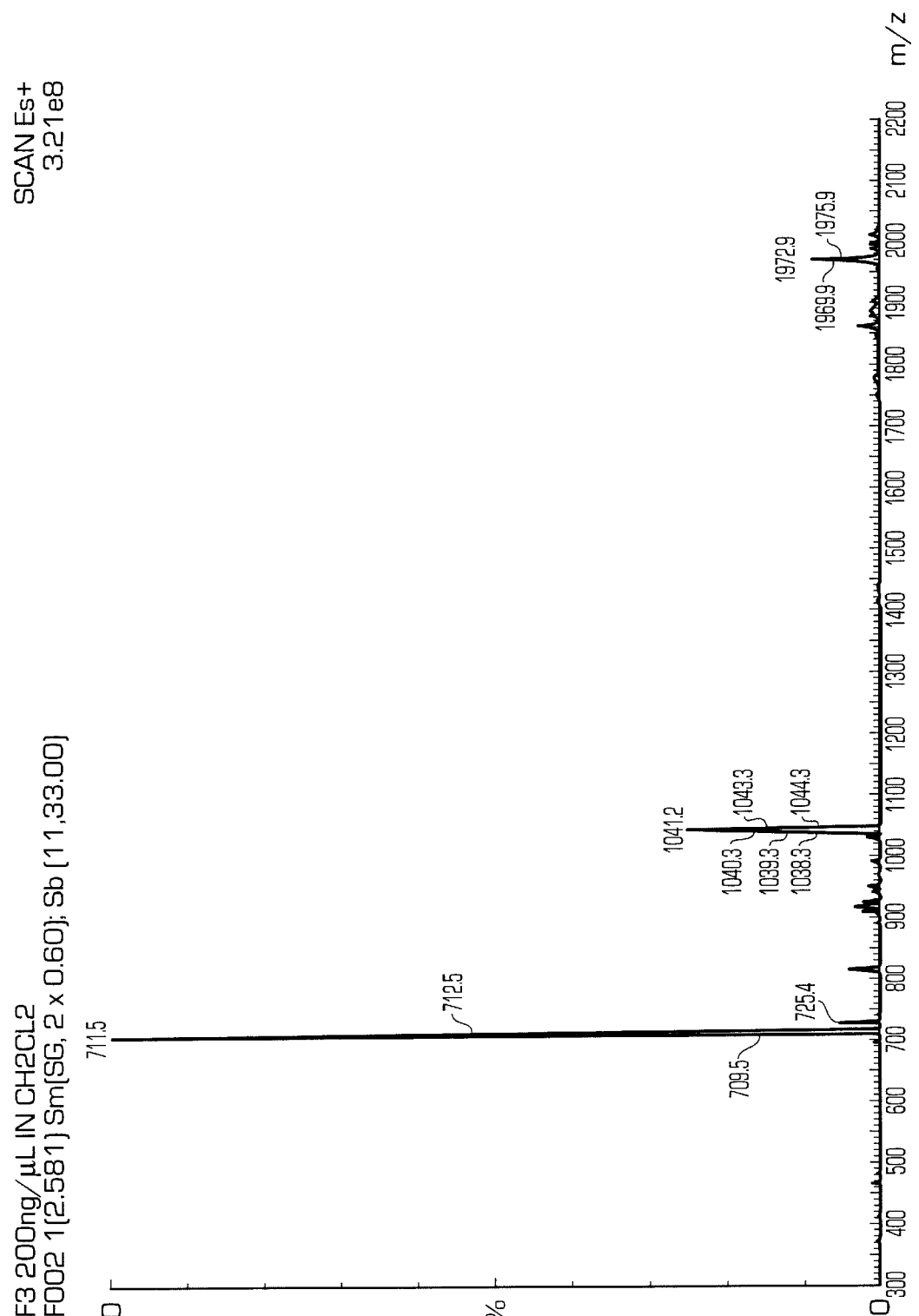
FIG. 2 is a view showing a whole LC mass spectrum of a product of Example 20.

FIG. 2 is a view showing the whole LC mass spectrum of the product of Example 20. In this LC mass spectrum, the molecular weight range between 1950 and 2030 is enlarged (see FIG. 3) for further analysis (Measurement condition of the LC mass spectrum is as follows: HPLC condition; instrument: HP1100, transfer phase: dichloromethane, sample-dilution solvent: dichloromethane; MS condition; instrument: Micromass QUATTRO LC, ionization mode; ESI+.). According to this analysis, the peak at a wavelength of 1972.9 is considered to be that of a compound having the structure below, namely, structure in which methanol is added only to the cationic portion of the product.

[Ru—I$_{1.5}$-{(S)—T-BINAP}]$_2$$^+$+(CH$_3$OH)

EXAMPLE 21

Production of [Ru—I$_{1.5}$-{(S)—T-BINAP}]$_2$(OTf)

A 200 ml reaction container was, after the air in the container was replaced by nitrogen, charged with 2.7 g (2.31 mmol) of [RuI(p-cymene) {(S)T-BINAP}]I and 110 ml of methanol, and the mixture was stirred at 55° C. for 16 hours. The mixture was cooled to room temperature and methanol was withdrawn. Then, under the nitrogen atmosphere, 0.416 g (2.42 mmol) of NaOTf was introduced into the mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.2 g (yield: 90.2%) of the titled compound.

EXAMPLE 22

Production of [Ru—I$_{1.5}$-{(S)—T-BINAP}]$_2$(OTf)

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP, 0.36 g (2.09 mmol) of NaOTf and 40 ml of methanol, and the mixture was stirred at 55° C. for 16 hours. The mixture was cooled to room temperature, and methanol was withdrawn. Then, under the nitrogen atmosphere, 20 ml of methylene chloride and 20 ml of deaerated water were added to the resulting mixture, followed by stirring for 10 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.9 g (yield: 88.2%) of the titled compound.

EXAMPLE 23

Production of [Ru—I$_{1.5}$-{(S)—T-BINAP}]$_2$(OTf)

A 200 ml reaction container was, after the air in the container was replaced by nitrogen, charged with 2.7 g (2.31 mmol) of [RuI(p-cymene) {(S)—T-BINAP}]I, 0.416 g (2.42 mmol) of NaOTf and 110 ml of methanol, and the mixture was stirred at 55° C. for 16 hours. The mixture was cooled to room temperature, and methanol was withdrawn. Then, under the nitrogen atmosphere, 20 ml of methylene chloride and 20 ml of deaerated water were added to the resulting mixture, followed by stirring for 30 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.2 g (yield: 90.2%) of the titled compound.

EXAMPLE 24

Production of [Ru—$_{1.5}$-{(S)—T-BINAP}]$_2$(OTs)

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature and methanol was withdrawn. Then, under the nitrogen atmosphere, 0.404 g (2.08 mmol) of NaOTs was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.03 g (yield: 92.3%) of the titled compound.

$^{31}$P NMR spectrum: 1.8 (d, J=36 Hz), 4.6 (d, J=34 Hz), 75.0 (d, J=34 Hz), 76.4 (d, J=36 Hz)

EXAMPLE 25

Production of [Ru—I$_{1.5}$-{(S)—T-BINAP}]$_2$(OMs)

An 80 ml Schlenk's tube was, after the air in the tube was replaced by nitrogen, charged with 1.0 g (1.02 mmol) of [RuI$_2$ (p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.247 g (2.09 mmol) of NaOMs was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.03 g (yield: 99.3%) of the titled compound.

$^{31}$P NMR spectrum: 1.8 (d, J=36 Hz), 4.6 (d, J=35 Hz), 75.0 (d, J=35 Hz), 76.4 (d, J=36 Hz)

EXAMPLE 26

Production of [Ru—I$_{1.5}$-{(S)—T-BINAP }]$_1$(PF$_6$)

An 80 ml Schlenk's tube was, after the air in the tube was replaced by nitrogen, charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.166 g (1.02 mmol) of NH$_4$PF$_6$ was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.1 g (yield: 97.8%) of the titled compound.

$^{31}$P NMR spectrum: 1.8 (d, J=36 Hz), 4.6 (d, J=34 Hz), 75.0 (d, J=34 Hz), 76.4 (d, J=36 Hz)

EXAMPLE 27

Production of [Ru—I$_{1.5}$-{(S)—T-BINAP}]$_2$(ClO$_4$)

An 80 ml Schlenk's tube was, after the air in the tube was replaced by nitrogen, charged with 1.0 g (1.02 mmol) of [RuI$_2$ (p-cymene)]$_2$, 1.4 g (2.06 mmol) of (S)—T-BINAP and 40 ml of methanol, and the mixture was stirred at 55° C. for 16 hours. The mixture was cooled to room temperature, and methanol was withdrawn. Then, under the nitrogen atmosphere, 0.256 g (2.09 mmol) of sodium perchlorate was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.95 g (yield: 95.0%) of the titled compound.

$^{31}$P NMR spectrum: −15.1 (sep, J=712 Hz), 1.8 (d, J=35 Hz), 4.6 (d, J=34 Hz), 75.0 (d, J=34 Hz), 76.4 (d,J=35 Hz).

EXAMPLE 28

Production of [Ru—I$_{1.5}$-{(S)—T-BINAP}]$_2$(OTf)

An 80 ml Schlenk's tube was, after the air in the tube was replaced by nitrogen, charged with 1.0 g (1.02 mmol) of [RuI$_2$(p-cymene)]$_2$, 1.28 g (2.06 mmol) of (S)-BINAP and 40 ml of methanol, and the mixture was stirred at 55° C. for 16 hours. The mixture was cooled to room temperature, and methanol was withdrawn. Then, under the nitrogen atmosphere, 0.36 g (2.09 mmol) of NaOTf was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.95 g (yield: 95.7%) of the titled compound.

EXAMPLE 29

Production of [Ru—I$_{1.5}$-{(S)-tBu-BINAP}]$_2$(OTf)

An 80 ml Schlenk's tube was, after the air in the tube was replaced by nitrogen, charged with 1.0 g (1.02 mmol) of [RuI$_2$(p-cymene)]$_2$, 1.75 g (2.06 mmol) of (S)-p-tBu-BINAP and 40 ml of methanol, and the mixture was stirred at 55° C.

for 16 hours. The mixture was cooled to room temperature, and methanol was withdrawn. Then, under the nitrogen atmosphere, 0.36 g (2.09 mmol) of NaOTf was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.4 g (yield: 96.1%) of the titled compound.

EXAMPLE 30

Production of [Ru—$I_{1.5}$-{(S)-DM-BINAP}]$_2$(OTf)

An 80 ml Schlenk's tube was, after the air in the tube was replaced by nitrogen, charged with 1.0 g (1.02 mmol) of [RuI$_2$(p-cymene)]$_2$, 1.52 g (2.07 mmol) of (S)-DM-BINAP and 40 ml of methanol, and the mixture was stirred at 55° C. for 16 hours. The mixture was cooled to room temperature, and methanol was withdrawn. Then, under the nitrogen atmosphere, 0.344 g (2.0 mmol) of NaOTf was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.2 g (yield: 96.99%) of the titled compound.

EXAMPLE 31

Production of (R)-4-methyl-2-oxetanone

A stainless autoclave with a volume of 500 ml was charged with 45.71 g (0.0433 mmol) of [Ru—$I_{1.5}$-{(S)—T-BINAP}]$_2$(OTf), 20.32 g (241.905 mmol) of 4-methylene-2-oxetanone, 80 ml of tetrahydrofuran and 0.45 ml of deaerated water under nitrogen, and the mixture was stirred at a reaction temperature of 50° C. under a hydrogen pressure of 50 kg/cm$^2$ for 15 hours. The resulting reaction solution was distilled using a Claisen tube distiller, to obtain 16.9 (yield: 81.2%) of a fraction having a boiling point of 71–73° C./29 mmHg (3866 Pa). The conversion rate of this reaction was 81.42%, and the turn-over number measured to evaluate the catalytic activity was 4550. A gas chromatography analysis effected by comparison to a standard material showed that the resultant product was 4-methyl-2-oxetanone. In order to determine the absolute configuration of the resulting product, the product was subjected to a gas chromatography (GC) analysis using an optically active column (Chiraldex G-TA 30 m, manufactured by ASTEC). The result of the analysis showed that the product obtained was an (R) isomer and the optical purity was 94.5% e.e.

EXAMPLE 32

Production of (R)-4-methyl-2-oxetanone

The same procedures as in Example 31 were carried out, except that 85.55 mg (0.0794 mmol) of [Ru—$I_{1.5}$-{(S)—T-BINAP}]$_2$(OTs) and 20.25 g (241.07 mmol) of 4-methylene-2-oxetanone were used, to obtain 20.45 g (yield: 98.64%) of the titled compound. The conversion rate of this reaction was 98.64%, and the turn-over number measured to evaluate the catalytic activity was 2990. The measurement of the absolute configuration showed that the resulting product was an (R) isomer and the optical purity was 95.6% e.e.

EXAMPLE 33

Production of (R)-4-methyl-2-oxetanone

The same procedures as in Example 31 were carried out, except that 47.71 mg (0.0476 mmol) of [Ru—$I_{1.5}$-{(S)—T-BINAP}]$_2$(OMs) and 20.42 g (243.1 mmol) of 4-methylene-2-oxetanone were used, to obtain 11.1 g (yield: 53.1%) of the titled compound. The conversion rate of this reaction was 53.1%, and the turn-over number measured to evaluate the catalytic activity was 2710. The measurement of the absolute configuration showed that the resultant product was an (R) isomer and the optical purity was 94.1% e.e.

EXAMPLE 34

Production of (R)-4-methyl-2-oxetanone

The same procedures as in Example 31 were carried out, except that 50.94 mg (0.0484 mmol) of [Ru—$I_{1.5}$-{(S)—T-BINAP}]$_2$(PF$_6$) and 20.46 g (243.57 mmol) of 4-methylene-2-oxetanone were used, to obtain 16.3 g (yield: 77.8%) of the titled compound. The conversion rate of this reaction was 77.80%, and the turn-over number measured to evaluate the catalytic activity was 3910. The measurement of the absolute configuration showed that the resultant product was an (R) isomer and the optical purity was 94.7% e.e.

EXAMPLE 35

Production of (R)-4-methyl-2-oxetanone

The same procedures as in Example 31 were carried out, except that 47.91 mg (0.0476 mmol) of [Ru—$I_{1.5}$-{(S)—T-BINAP}]$_2$(ClO$_4$) and 20.29 g (241.55 mmol) of 4-methylene-2-oxetanone were used, to obtain 15.9 g (yield: 76.5%) of the titled compound. The conversion rate of this reaction was 76.5%, and the turn-over number measured to evaluate the catalytic activity was 3880. The measurement of the absolute configuration showed that the resultant product was an (R) isomer and the optical purity was 95.8% e.e.

EXAMPLE 36

Production of (R)-4-methyl-2-oxetanone

The same procedures as in Example 31 were carried out, except that 47.91 mg (0.0479 mmol) of [Ru—$I_{1.5}$-{(S)-BINAP}]$_2$(OTf) and 20.0 g (238.1 mmol) of 4-methylene-2-oxetanone were used, to obtain 15.9 g (yield: 77.65%) of the titled compound. The conversion rate of this reaction was 77.65%, and the turn-over number measured to evaluate the catalytic activity was 3860. The measurement of the absolute configuration showed that the resultant product was an (R) isomer and the optical purity was 95.0% e.e.

EXAMPLE 37

Production of (R)-4-methyl-2-oxetanone

The same procedures as in Example 31 were carried out, except that 70.73 mg (0.0476 mmol) of [Ru—$I_{1.5}$-{(S)-p-tBu-BINAP}]$_2$(OTf) and 20.34 g (242.14 mmol) of 4-methylene-2-oxetanone were used, to obtain 12.4 g (yield:

59.55%) of the titled compound. The conversion rate of this reaction was 59.65%, and the turn-over number measured to evaluate the catalytic activity was 3030. The measurement of the absolute configuration showed that the resultant product was an (R) isomer and the optical purity was 95.8%e.e.

EXAMPLE 38

Production of (R)-4-methyl-2-oxetanone

The same procedures as in Example 31 were carried out, except that 69.5 mg (0.0625 mmol) of [Ru—$I_{1.5}$-{(S)-DM-BINAP}]$_2$(OTf) and 20.0 g (238.1 mmol) of 4-methylene-2-oxetanone were used, to obtain 19.3 g (yield: 94.2%) of the titled compound. The conversion rate of this reaction was 94.2%, and the turn-over number measured to evaluate the catalytic activity was 3580. The measurement of the absolute configuration showed that the resultant product was an (R) isomer and the optical purity was 94.0% e.e.

EXAMPLE 39

Production of [Ru—$I_{1.5}$-{(S)-SEGPHOS)}]$_2$(OTf)

Figure 4:
FIG. 4 is a view showing the $^{31}$P-NMR spectrum of $[\text{Ru}—\text{I}_{1.5}—\{(S)\text{-SEGPHOS}\}]_2(\text{OTf})$ obtained in Example 39.

An 80 ml Schlenk's tube was, after the air in the tube was replaced by nitrogen, charged with 0.5 g (0.51 mmol) of [RuI$_2$(p-cymene)]$_2$, 0.63 mg (1.03 mmol) of (S)-SEGPHOS and 20 ml of deaerated DMF, and the mixture was stirred at 75° C. for 16 hours. The mixture was cooled to 40° C. and DMF was withdrawn. Then, under the nitrogen atmosphere, 88 ml (0.51 mmol) of NaOTf was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 0.95 g (yield: 94.3%) of the titled compound. The $^{31}$P-NMR spectrum of the resultant product is shown in FIG. 4.

EXAMPLE 40

Production of [Ru—$I_{1.5}$-{(S)-SEGPHOS)}]$_2$(OTf)

A 200 ml reaction container was, after the air in the container was replaced by nitrogen, charged with 2.7 g (2.45 mmol) of [RuI(p-cymene) {(S)-SEGPHOS)}]I and 110 ml of deaerated DMF, and the mixture was stirred at 75° C. for 16 hours. The mixture was cooled to 40° C. and DMF was withdrawn. Then, under the nitrogen atmosphere, 0.422 g (2.45 mmol) of NaOTf was introduced into the mixture, and 20 ml of methylene chloride and 20 ml of deaerated water were further added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.3 g (yield: 95.0%) of the titled compound.

EXAMPLE 41

Production of [Ru—$I_{1.5}$-{(S)-SEGPHOS}]$_2$(OTf)

An 80 ml Schlenk's tube was, after the air in the tube was replaced by nitrogen, charged with 1.0 g (1.02 mmol) of [RuI$_2$(p-cymene)]$_2$, 1.26 g (2.06 mmol) of (S)-SEGPHOS, 0.36 g (2.09 mmol) of NaOTf and 40 ml of deaerated DMF, and the mixture was stirred at 75° C. for 16 hours. The mixture was cooled to 40° C., and DMF was withdrawn under reduced pressure. Then, under the nitrogen atmosphere, 20 ml of methylene chloride and 20 ml of deaerated water were added to the resulting mixture, followed by stirring for 10 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.9 g (yield: 94.3%) of the titled compound.

EXAMPLE 42

Production of [Ru—$I_{1.5}$-{(S)-SEGPHOS)}]$_2$(OTf)

A 200 ml reaction container was, after the air in the container was replaced by nitrogen, charged with 2.7 g (2.45 mmol) of [RuI(p-cymene){(S)-SEGPHOS)}]I, 0.421 g (2.45 mmol) of NaOTf and 110 ml of deaerated DMF, and the mixture was stirred at 75° C. for 16 hours. The mixture was cooled to 40° C., and DMF was withdrawn. Then, under the nitrogen atmosphere, 20 ml of methylene chloride and 20 ml of deaerated water were added to the resulting mixture, followed by stirring for 30 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.2 g (yield: 90.9%) of the titled compound.

EXAMPLE 43

Production of [Ru—$I_{1.5}$-{(S)-SEGPHOS)}]$_2$(PF$_6$)

An 80 ml Schlenk's tube was, after the air in the tube was replaced by nitrogen, charged with 1.0 g (1.02 mmol) of [RuI$_2$(p-cymene)]$_2$, 1.26 g (2.06 mmol) of (S)-SEGPHOS and 40 ml of deaerated DMF, and the mixture was stirred at 75° C. for 16 hours. The mixture was cooled to 40° C., and DMF was withdrawn. Then, under the nitrogen atmosphere, 0.171 g (1.02 mmol) of NH$_4$PF$_6$ was introduced into the mixture, and 20 ml of methylene chloride and 20 ml of deaerated water were added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.0 g (yield: 99.7%) of the titled compound.

EXAMPLE 44

Production of [Ru—$I_{1.5}$-{(S)-SEGPHOS)}]$_2$(OTs)

An 80 ml Schlenk's tube was, after the air in the tube was replaced by nitrogen, charged with 1.0 g (1.02 mmol) of [RuI$_2$(p-cymene)]$_2$, 1.26 g (2.06 mmol) of (S)-SEGPHOS and 40 ml of deaerated DMF, and the mixture was stirred at 75° C. for 16 hours. The mixture was cooled to 40° C., and DMF was withdrawn. Then, under the nitrogen atmosphere, 0.404 g (2.08 mmol) of NaOTs was introduced into the mixture, and 20 ml of methylene chloride and 20 ml of deaerated water were added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 2.03 g (yield: 98.5%) of the titled compound.

EXAMPLE 45

Production of [Ru—I$_{1.5}$-{(S)-SEGPHOS)}]$_2$(OMs)

An 80 ml Schlenk's tube was, after the air in the tube was replaced by nitrogen, charged with 1.0 g (1.02 mmol) of [RuI$_2$(p-cymene)]$_2$, 1.26 g (2.06 mmol) of (S)-SEGPHOS and 40 ml of deaerated DMF, and the mixture was stirred at 75° C. for 16 hours. The mixture was cooled to 40° C., and DMF was withdrawn. Then, under the nitrogen atmosphere, 0.247 g (2.09 mmol) of NaOMs was introduced into the mixture, and 20 ml of methylene chloride and 20 ml of deaerated water were added to the resulting mixture, followed by stirring for 16 hours. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.8 g (yield: 94.5%) of the titled compound.

EXAMPLE 46

Production of [Ru—I$_{1.5}$-{(S)-SEGPHOS)}]$_2${OS(O)$_2$C$_4$F$_9$}

An 80 ml Schlenk's tube was, after the air in the tube was replaced by nitrogen, charged with 1.2 g (1.23 mmol) of [RuI$_2$(p-cymene)]$_2$, 1.51 g (2.47 mmol) of (S)-SEGPHOS, 0.47 g (1.39 mmol) of KOS(O)$_2$C$_4$F$_9$ and 36 ml of deaerated DMF, and the mixture was stirred at 75° C. for 16 hours. The mixture was cooled to 40° C., and DMF was withdrawn under reduced pressure. Then, under the nitrogen atmosphere, 30 ml of methylene chloride and 30 ml of deaerated water were added to the resulting mixture, followed by stirring for 10 minutes. The methylene chloride layer was extracted into a sampling syringe and washed with 30 ml of deaerated water, followed by distilling methylene chloride under reduced pressure. The resulting complex was then dried at 30° C. under reduced pressure for 4 hours, to obtain 3.09 g (yield: 119.4%) of the titled compound.

EXAMPLE 47

Production of [Ru—I$_{1.5}$-{(S)-SEGPHOS)}]$_2${OS(O)$_2$C$_8$F$_{17}$}

An 80 ml Schlenk's tube was, after the air in the tube was replaced by nitrogen, charged with 0.304 g (0.311 mmol) of [RuI$_2$(p-cymene)]$_2$, 0.389 g (0.638 mmol) of (S)-SEGPHOS, 0.191 g (0.355 mmol) of KOS(O)$_2$C$_8$F$_{17}$ and 10 ml of deaerated DMF, and the mixture was stirred at 75° C. for 16 hours. The mixture was cooled to 40° C., and DMF was withdrawn under reduced pressure. Then, under the nitrogen atmosphere, 20 ml of methylene chloride and 10 ml of deaerated water were added to the resulting mixture, followed by stirring for 10 minutes. The methylene chloride layer was extracted into a sampling syringe and washed with 10 ml of deaerated water, followed by distilling methylene chloride under reduced pressure. The resulting complex was then dried at 30° C. under reduced pressure for 4 hours, to obtain 0.87 g (yield: 121.6%) of the titled compound.

EXAMPLE 48

Production of (R)-4-methyl-2-oxetanone

A stainless autoclave with a volume of 500 ml was charged with 33.59 g (0.034 mmol) of [Ru—I$_{1.5}$-{(S)-SEGPHOS)}]$_2$(OTf), 20.55 g (244.6 mmol) of 4-methylene-2-oxetanone, 80 ml of tetrahydrofuran and 0.45 g of deaerated water under nitrogen, and the mixture was stirred at a reaction temperature of 50° C. under a hydrogen pressure of 50 kg/cm$^2$ for 15 hours. The resulting reaction solution was distilled using a Claisen tube distiller, to obtain 19.1 g (yield: 90.8%) of a fraction having a boiling point of 71–73° C./29 mmHg (3866 Pa). The conversion rate of this reaction was 90.8%, and the turn-over number measured to evaluate the catalytic activity was 6530. A gas chromatography analysis effected by comparison to a standard material showed that the resultant product was 4-methyl-2-oxetanone. In order to determine the absolute configuration of the resultant product, the product was subjected to a gas chromatography (GC) analysis using an optically active column (Chiraldex G-TA 30 m, manufactured by ASTEC). The result of the analysis showed that the resultant product was an (R) isomer and the optical purity was 94.5% e.e.

EXAMPLE 49

Production of (R)-4-methyl-2-oxetanone

The same procedures as in Example 48 were carried out, except that 35.84 mg (0.0368 mmol) of [Ru—I$_{1.5}$-{(S)-SEGPHOS)}]$_2$(PF$_6$) and 20.38 g (242.62 mmol) of 4-methylene-2-oxetanone were used, to obtain 13.7 g (yield: 65.6%) of the titled compound. The conversion rate of this reaction was 65.6%, and the turn-over number measured to evaluate the catalytic activity was 4320. The measurement of the absolute configuration showed that the resultant product was an (R) isomer and the optical purity was 95.5% e.e.

EXAMPLE 50

Production of (R)-4-methyl-2-oxetanone

The same procedures as in Example 48 were carried out, except that 36.75 mg (0.0364 mmol) of [Ru—I$_{1.5}$-{(S)-SEGPHOS)}]$_2$(OTs) and 20.0 g (238.1 mmol) of 4-methylene-2-oxetanone were used, to obtain 13.88 g (yield: 67.78%) of the titled compound. The conversion rate of this reaction was 68.79%, and the turn-over number measured to evaluate the catalytic activity was 4500. The measurement of the absolute configuration showed that the resultant product was an (R) isomer and the optical purity was 95.6% e.e.

EXAMPLE 51

Production of (R)-4-methyl-2-oxetanone

The same procedures as in Example 48 were carried out, except that 33.98 mg (0.0364 mmol) of [Ru—I$_{1.5}$-{(S)-SEGPHOS)}]$_2$(OMs) and 20.42 mg (243.1 mmol) of 4-methylene-2-oxetanone were used, to obtain 14.55 g (yield: 69.6%) of the titled compound. The conversion rate of this reaction was 69.6%, and the turn-over number measured to evaluate the catalytic activity was 4650. The measurement of the absolute configuration showed that the resultant product was an (R) isomer and the optical purity was 94.8% e.e.

EXAMPLE 52

Production of (R)-4-methyl-2-oxetanone

The same procedures as in Example 48 were carried out, except that 44.65 mg (0.0476 mmol) of [Ru—I$_{1.5}$-{(S)-

SEGPHOS)}]$_2$(ClO$_4$) and 20.29 mg (241.55 mmol) of 4-methylene-2-oxetanone were used, to obtain 17.59 g (yield: 84.7%) of the titled compound. The conversion rate of this reaction was 84.7%, and the turn-over number measured to evaluate the catalytic activity was 4300. The measurement of the absolute configuration showed that the resultant product was an (R) isomer and the optical purity was 95.4% e.e.

EXAMPLE 53

Production of (R)-4-methyl-2-oxetanone

The same procedures as in Example 48 were carried out, except that 25.0 mg (0.0238 mmol) of [Ru—I$_{1.5}$-{(S)-SEGPHOS)}]$_2${OS(O)$_2$C$_4$F$_9$} and 20.34 mg (242.1 mmol) of 4-methylene-2-oxetanone were used, and the stirring was continued for 15 hours at a reaction temperature of 60° C. under a hydrogen pressure of 40 kg/cm$^2$, to obtain 18.99 g (yield: 91.2%) of the titled compound. The conversion rate of this reaction was 100%, and the turn-over number measured to evaluate the catalytic activity was 10180. The measurement of the absolute configuration showed that the resultant product was an (R) isomer and the optical purity was 94.4% e.e.

EXAMPLE 54

Production of (R)-4-methyl-2-oxetanone

The same procedures as in Example 48 were carried out, except that 22.85 mg (0.0198 mmol) of [Ru—I$_{1.5}$-{(S)-SEGPHOS)}]$_2${OS(O)$_2$C$_8$F$_{17}$} and 20.54 g (244.5 mmol) of 4-methylene-2-oxetanone were used, and the stirring was continued for 15 hours at a reaction temperature of 60□ and under a hydrogen pressure of 40 kg/cm2, to obtain 18.45 g (yield: 87.7%) of the titled compound. The conversion rate of this reaction was 87.7% and the turn-over number measured to evaluate the catalytic activity was 10830. The measurement of the absolute configuration showed that the resultant product was an (R) isomer and the optical purity was 93.8% e.e.

Comparative Example 1

Production of (R)-4-methyl-2-oxetanone

The ruthenium-iodo-optically active phosphine complex described in JP-A No. H7-206885 was produced. Using this phosphine complex as catalyst, optically active 4-methyl-2-oxetanone was produced. Specifically, a 300 ml reaction container in which the air was replaced by nitrogen in advance was charged with 0.57 g (0.632 mmol) of Ru$_2$Cl$_4$[(S)—T-BINAP]$_2$NEt$_3$, 0.95 g (6.34 mmol) of NaI, 2.0 mg (0.0063 mmol) of (C$_4$H$_9$)$_4$NBr, 50 ml of methylene chloride and 20 ml of distilled water, and the mixture was stirred at room temperature for 44 hours. After the reaction was completed, the methylene chloride layer was extracted into a sampling syringe, followed by distilling methylene chloride under reduced pressure. The resulting complex was dried under reduced pressure at 50° C. for 4 hours, to obtain 0.65 g of Ru—I—[(S)—T-BINAP]. The same procedures as in Example 12 were carried out, except that 82.0 mg (0.0794 mmol) of this complex Ru—I—[(S)—T-BINAP] and 20.1 g (239.3 mmol) of 4-methylene-2-oxetanone were used, to obtain 10.0 g (yield: 48.8%) of the titled compound. The conversion rate of this reaction was 50.0%, and the turn-over number measured to evaluate the catalytic activity was 1500. The measurement of the absolute configuration showed that the resultant product was an (R) isomer and the optical purity was 93.4% e.e.

Comparative Example 2

Production of (R)-4-methyl-2-oxetanone

The same procedures as in Example 12 were carried out, except that 139.0 mg (0.119 mmol) of [RuI(p-cymene)((S)—T-BINAP)]I and 20.0 g (238.1 mmol) of 4-methylene-2-oxetanone were used, to obtain 9.50 g (yield: 47.5%) of the titled compound. The conversion rate of this reaction was 48.0%, and the turn-over number measured to evaluate the catalytic activity was 960. The measurement of the absolute configuration showed that the resultant product was an (R) isomer and the optical purity was 92.8% e.e.

Comparative Example 3

Production of (R)-4-methyl-2-oxetanone

The same procedures as in Example 12 were carried out, except that 215.5 mg (0.238 mmol) of [Ru(CH$_3$COO)$_2$[(S)—T-BINAP] and 20.0 g (238.1 mmol) of 4-methylene-2-oxetanone were used, to obtain 11.0 g (yield: 55.0%) of the titled compound. The conversion rate of this reaction was 56.6%, and the turn-over number measured to evaluate the catalytic activity was 570. The measurement of the absolute configuration showed that the resultant product was an (R) isomer and the optical purity was 93.6% e.e. The catalytic activity (turn-over number), configuration and optical purity (%e.e.) of 4-methyl-2-oxetanone in Examples 12–19, 31–38, 46–50 and Comparative Examples 1–3 are shown collectively in Table 1.

TABLE 1

| | Catalytic activity | 4-methyl-2-oxetanone | |
|---|---|---|---|
| | (Turn-over number) | Configuration | Optical purity (% e.e.) |
| Example 12 | 2630 | R-isomer | 94.3 |
| Example 13 | 2480 | R-isomer | 95.3 |
| Example 14 | 2290 | R-isomer | 94.9 |
| Example 15 | 2590 | R-isomer | 94.3 |
| Example 16 | 2630 | R-isomer | 94.0 |
| Example 17 | 2480 | R-isomer | 94.0 |
| Example 18 | 2500 | R-isomer | 94.1 |
| Example 19 | 2600 | R-isomer | 94.2 |
| Example 31 | 4550 | R-isomer | 94.5 |
| Example 32 | 2990 | R-isomer | 95.6 |
| Example 33 | 2710 | R-isomer | 94.1 |
| Example 34 | 3910 | R-isomer | 94.7 |
| Example 35 | 3880 | R-isomer | 95.8 |
| Example 36 | 3860 | R-isomer | 95.0 |
| Example 37 | 3030 | R-isomer | 95.8 |
| Example 38 | 3580 | R-isomer | 94.0 |
| Example 48 | 6530 | R-isomer | 94.5 |
| Example 49 | 4320 | R-isomer | 95.5 |
| Example 50 | 4500 | R-isomer | 95.6 |
| Example 51 | 4650 | R-isomer | 94.8 |
| Example 52 | 4300 | R-isomer | 95.4 |
| Example 53 | 10180 | R-isomer | 94.4 |
| Example 54 | 10830 | R-isomer | 93.8 |
| Comparative Example 1 | 1500 | R-isomer | 93.4 |
| Comparative Example 2 | 960 | R-isomer | 92.8 |
| Comparative Example 3 | 570 | R-isomer | 93.6 |

Examples of the Second Aspect of the Invention

In the following examples, the properties of the compounds prepared in examples were measured using the following instruments.

$^{31}$P NMR spectrum: DRX500 model equipment (manufactured by Bruker)

External standard material: 85% phosphoric acid

Solvent: deuterated chloroform (Measurement of optical purity)

Gas chromatograph equipment: HEWLETT PACKARD 5890 SERIES II

Optically active column (Chraldex G-TA 30m (manufactured by ASTEC))

EXAMPLE 55

Production of a Complex Mixture of [Ru((S)-SEGPHOS)(CH$_3$CN)$_4$](ONf)$_2$, [Ru((S)-SEGPHOS)(CH$_3$CN)$_4$](I)$_2$, [Ru ((S)-SEGPHOS)(CH$_3$CN)$_4$](I)(ONf) and [RuI((S)-SEGPHOS)(CH$_3$CN)$_3$](ONf)

A 100 ml eggplant-shape flask was, after the air in the flask was replaced by nitrogen, charged with 685 mg (0.700 mmol) of [RuI$_2$(p-cymene)]$_2$, 863 mg (1.414 mmol) of (S)-SEGPHOS, 239 mg (0.707 mmol) of KONf and 35 ml of deaerated acetonitrile, and the mixture was stirred at 80° C. for 16 hours. The mixture was cooled to 40° C. and acetonitrile was withdrawn under reduced pressure. Then, in the nitrogen atmosphere, 20 ml of methylene chloride and 20 ml of deaerated water were added to the resulting mixture, followed by stirring for 10 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 1.6 g (yield: 89.7%) of the titled compound.

$^{31}$P NMR; δ43.1, 45.9, 47.5 ppm

Figure 3:
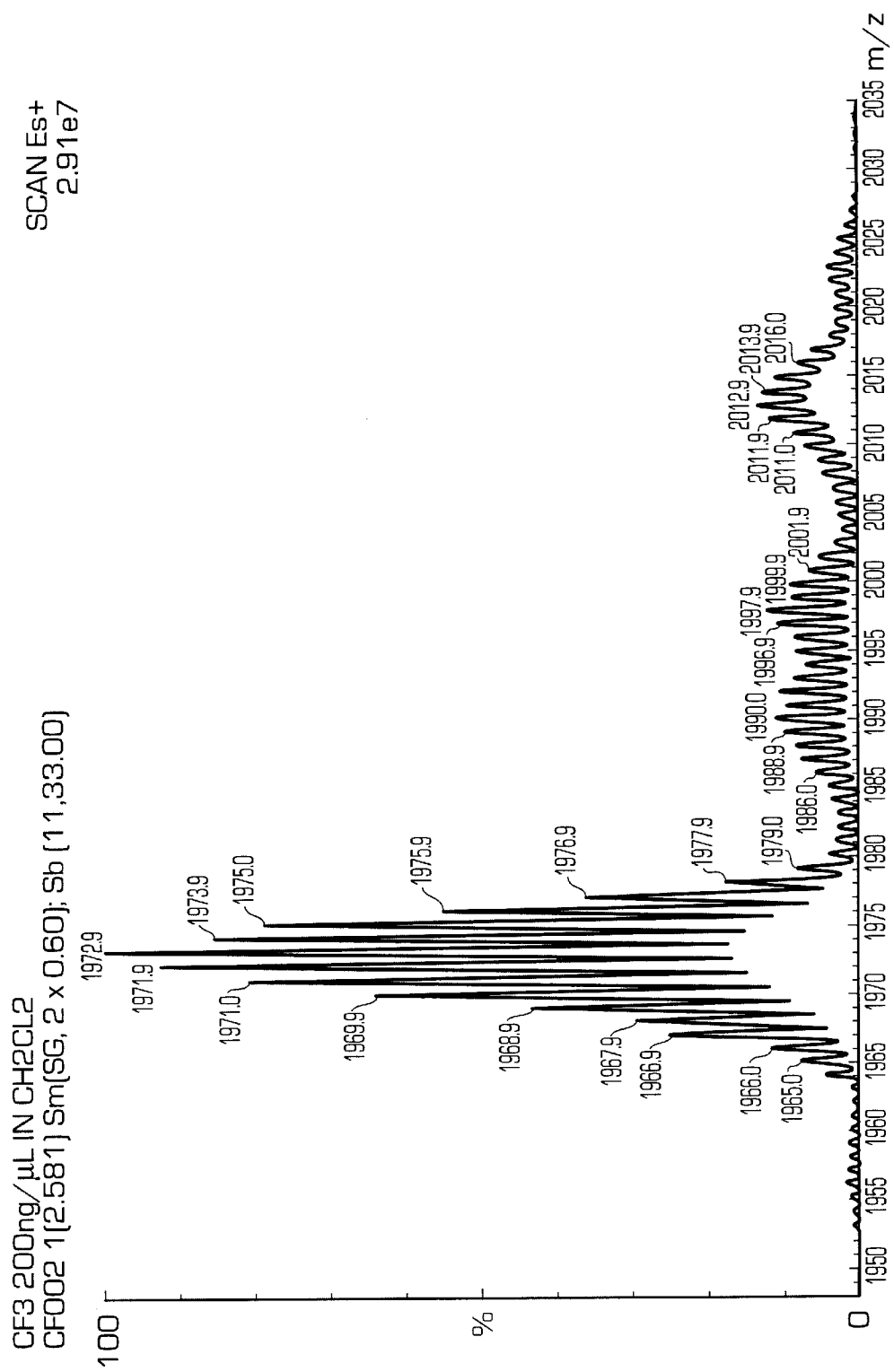
FIG. 3 is an enlarged view of the LC mass spectrum of FIG. 2 in a molecular weight range between 1950 and 2030.

From FIG. 3, the ratio of the amount of [RuI((S)-SEGPHOS)(CH$_3$CN)$_3$](ONf) (at 43.1 and 45.8 ppm) to the total amount of [Ru((S)-SEGPHOS)(CH$_3$CN)$_4$](ONf)$_2$, [Ru(S)-SEGPHOS)(CH$_3$CN)$_4$](I)$_2$ and [Ru((S)-SEGPHOS)(CH$_3$CN)$_4$](I)(ONf) (at 47.5 ppm) was 29:71.

EXAMPLE 56

Production of a Complex Mixture of [Ru((S)-SEGPHOS)(CH$_3$CN)$_4$](ONf)$_2$, [Ru((S)-SEGPHOS)(CH$_3$CN)$_4$](I)$_2$, [Ru((S)-SEGPHOS)(CH$_3$CN)$_4$](I)(ONf) and [RuI((S)-SEGPHOS)(CH$_3$CN)$_3$](ONf)

A 20 ml eggplant-shape flask was, after the air in the flask was replaced by nitrogen, charged with 35 mg (0.122 mmol) of [RuI(p-cymene) {(S)-SEGPHOS}]I, 20.9 mg (0.0619 mmol) of KONf and 3 ml of deaerated acetonitrile, and the mixture was stirred for 16 hours. The mixture was cooled to 40° C., and acetonitrile was withdrawn under reduced pressure. Then, in the nitrogen atmosphere, 10 ml of methylene chloride and 10 ml of deaerated water were added to the resulting mixture, followed by stirring for 10 minutes. The methylene chloride layer was extracted into a sampling syringe and washed with 20 ml of deaerated water, followed by distilling methylene chloride under reduced pressure. The resulting complex was then dried at 30° C. under reduced pressure for 4 hours, to obtain 130mg (yield: 84.1%) of the titled compound.

$^{31}$P NMR; δ43.1, 45.8, 47.5 ppm

From FIG. 4, the ratio of the amount of [RuI((S)-SEGPHOS)(CH$_3$CN)$_3$](ONf) (at 43.1 and 45.8 ppm) to the total amount of [Ru((S)-SEGPHOS)(CH$_3$CN)$_4$](ONf)$_2$, [Ru((S)-SEGPHOS)(CH$_3$CN)$_4$](I)$_2$ and [Ru((S)-SEGPHOS)(CH$_3$CN)$_4$](I)(ONf) (at 47.5 ppm) was 45:54.

EXAMPLE 57

Production of a Complex Mixture of [Ru((S)-SEGPHOS)(CH$_3$CN)$_4$](OTf)$_2$, [Ru((S)-SEGPHOS)(CH$_3$CN)$_4$](I)$_2$, [Ru((S)-SEGPHOS)(CH$_3$CN)$_4$](I)(OTf) and [RuI((S)-SEGPHOS)(CH$_3$CN)$_3$](OTf)

A 20 ml eggplant-shape flask was, after the air in the flask was replaced by nitrogen, charged with 60 mg (0.0613 mmol) of [RuI$_2$(p-cymene)]$_2$, 75.7 mg (0.124 mmol) of (S)-SEGPHOS, 11.7 mg (0.0619 mmol) of KOTf and 3 ml of deaerated acetonitrile, and the mixture was stirred at 80° C. for 16 hours. The mixture was cooled to 40° C., and acetonitrile was withdrawn under reduced pressure. Then, in the nitrogen atmosphere, 10 ml of methylene chloride and 15 ml of deaerated water were added to the resulting mixture, followed by stirring for 10 minutes. The methylene chloride layer was extracted into a sampling syringe and washed with 15 ml of deaerated water, followed by distilling methylene chloride under reduced pressure. The resulting complex was then dried at 30° C. under reduced pressure for 4 hours, to obtain 120 mg (yield: 88.1%) of the titled compound.

$^{31}$P NMR; δ43.1, 45.8, 47.5 ppm

Figure 5:
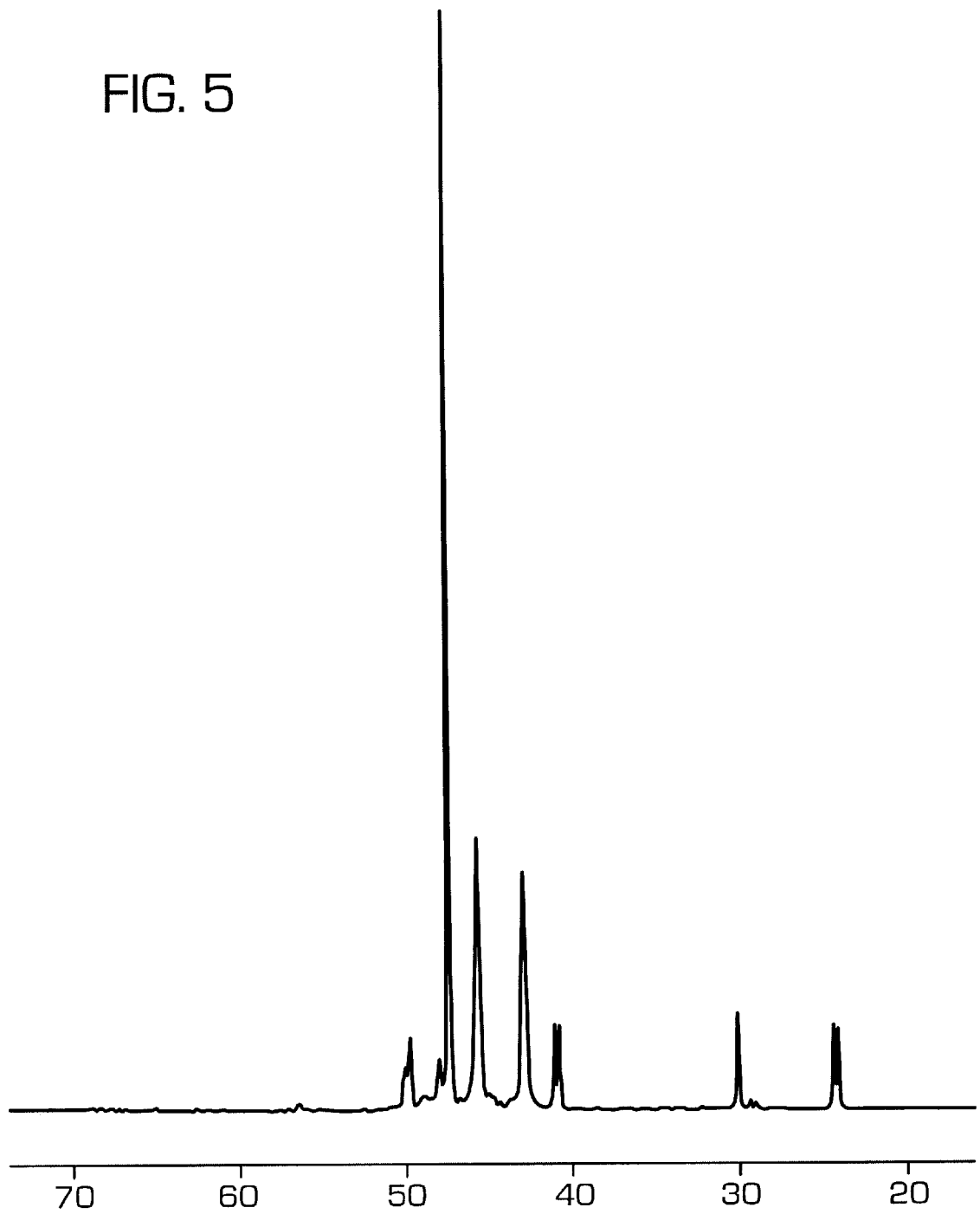
FIG. 5 is a view showing the $^{31}$P NMR spectrum of a ruthenium-iodo-optically active phosphine complex mixture obtained in Example 55.

From FIG. 5, the ratio of the amount of [RuI((S)-SEGPHOS)(CH$_3$CN)$_3$](OTf) (at 43.1 and 45.8 ppm) to the total amount of [Ru((S)-SEGPHOS)(CH$_3$CN)$_4$](OTf)$_2$, [Ru((S)-SEGPHOS)(CH$_3$CN)$_4$](I)$_2$ and [Ru((S)-SEGPHOS)(CH$_3$CN)$_4$](I)(OTf) (at 47.5 ppm) was 37:63.

EXAMPLE 58

Production of a Complex Mixture of [Ru((S)-SEGPHOS)(CH$_3$CN)$_4$](OhepDf)$_2$, [Ru((S)-SEGPHOS)(CH$_3$CN)$_4$](I)$_2$, [Ru((S)-SEGPHOS)(CH$_3$CN)$_4$](I)(OhepDf) and [RuI((S)-SEGPHOS)(CH$_3$CN)$_3$](OhepDf)

A 20 ml eggplant-shape flask was, after the air in the flask was replaced by nitrogen, charged with 60.0 mg (0.0613 mmol) of [RuI$_2$(p-cymene)]$_2$, 75.7 mg (0.124 mmol) of (S)-SEGPHOS, 33.3 mg (0.0619 mmol) of KOhepDf and 3 ml of deaerated acetonitrile, and the mixture was stirred at 80° C. for 16 hours. The mixture was cooled to 40° C., and acetonitrile was withdrawn under reduced pressure. Then, in the nitrogen atmosphere, 10 ml of methylene chloride and 15 ml of deaerated water were added to the resulting mixture, followed by stirring for 10 minutes. The methylene chloride layer was extracted into a sampling syringe and washed with 15 ml of deaerated water, followed by distilling methylene chloride under reduced pressure. The resulting complex was then dried at 30° C. under reduced pressure for 4 hours, to obtain 150 mg (yield: 83.8%) of the titled compound.

$^{31}$P NMR; δ43.2, 45.8, 47.5 ppm

Figure 6:
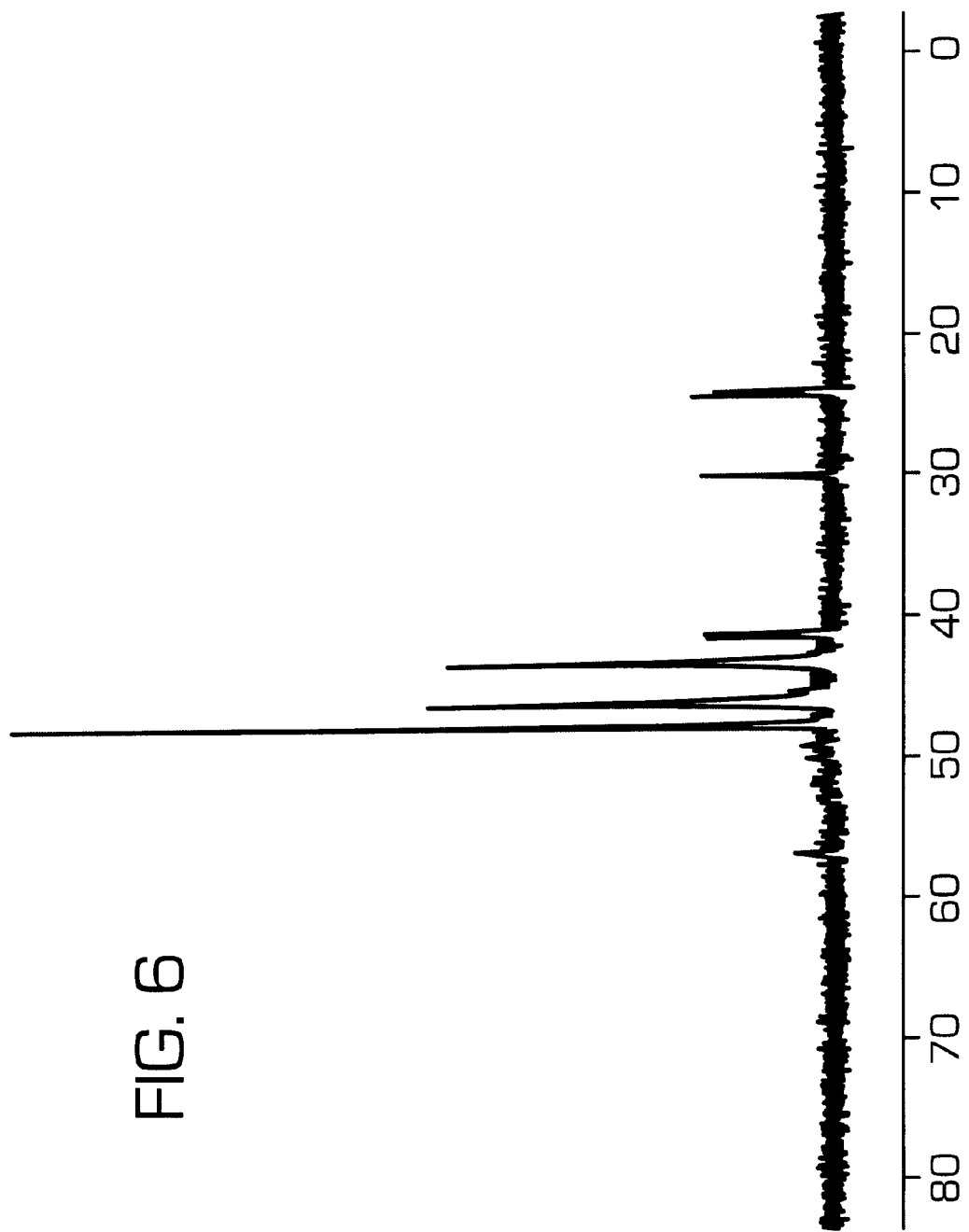
FIG. 6 is a view showing the $^{31}$P NMR spectrum of a ruthenium-iodo-optically active phosphine complex mixture obtained in Example 56.

From FIG. 6, the ratio of the amount of [RuI((S)-SEGPHOS)(CH$_3$CN)$_3$](OhepDf) (at 43.2 and 45.8 ppm) to the total amount of [Ru((S)-SEGPHOS)(CH$_3$CN)$_4$](OhepDf)$_2$, [Ru((S)-SEGPHOS)(CH$_3$CN)$_4$](I)$_2$ and [Ru((S)-SEGPHOS)(CH$_3$CN)$_4$](I)(OhepDf) (at 47.5 ppm) was 42:58.

EXAMPLE 59

Production of a Complex Mixture of [Ru((S)-SEGPHOS)(PhCN)$_4$](ONf)$_2$, [Ru((S)-SEGPHOS)(PhCN)$_4$](I)$_2$, [Ru((S)-SEGPHOS)(PhCN)$_4$](I)(ONf) and [RuI((S)-SEGPHOS)(PhCN)$_3$](ONf)

A 20 ml eggplant-shape flask was, after the air in the flask was replaced by nitrogen, charged with 60.0 mg (0.0613 mmol) of [RuI$_2$(p-cymene)]$_2$, 75.7 mg (0.124 mmol) of (S)-SEGPHOS, 20.9 mg (0.0619 mmol) of KONf and 3 ml of deaerated benzonitrile, and the mixture was stirred at 80° C. for 16 hours. The mixture was cooled to 40° C., and benzonitrile was withdrawn under reduced pressure. Then, in the nitrogen atmosphere, 10 ml of methylene chloride and 15 ml of deaerated water were added to the resulting mixture, followed by stirring for 10 minutes. The methylene chloride layer was extracted into a sampling syringe and washed with 15 ml of deaerated water, followed by distilling methylene chloride under reduced pressure. The resulting complex was then dried at 30° C. under reduced pressure for 4 hours, to obtain 140 mg (yield: 78.9%) of the titled compound.

$^{31}$P NMR; δ42.1, 44.0, 46.6 ppm

Figure 7:
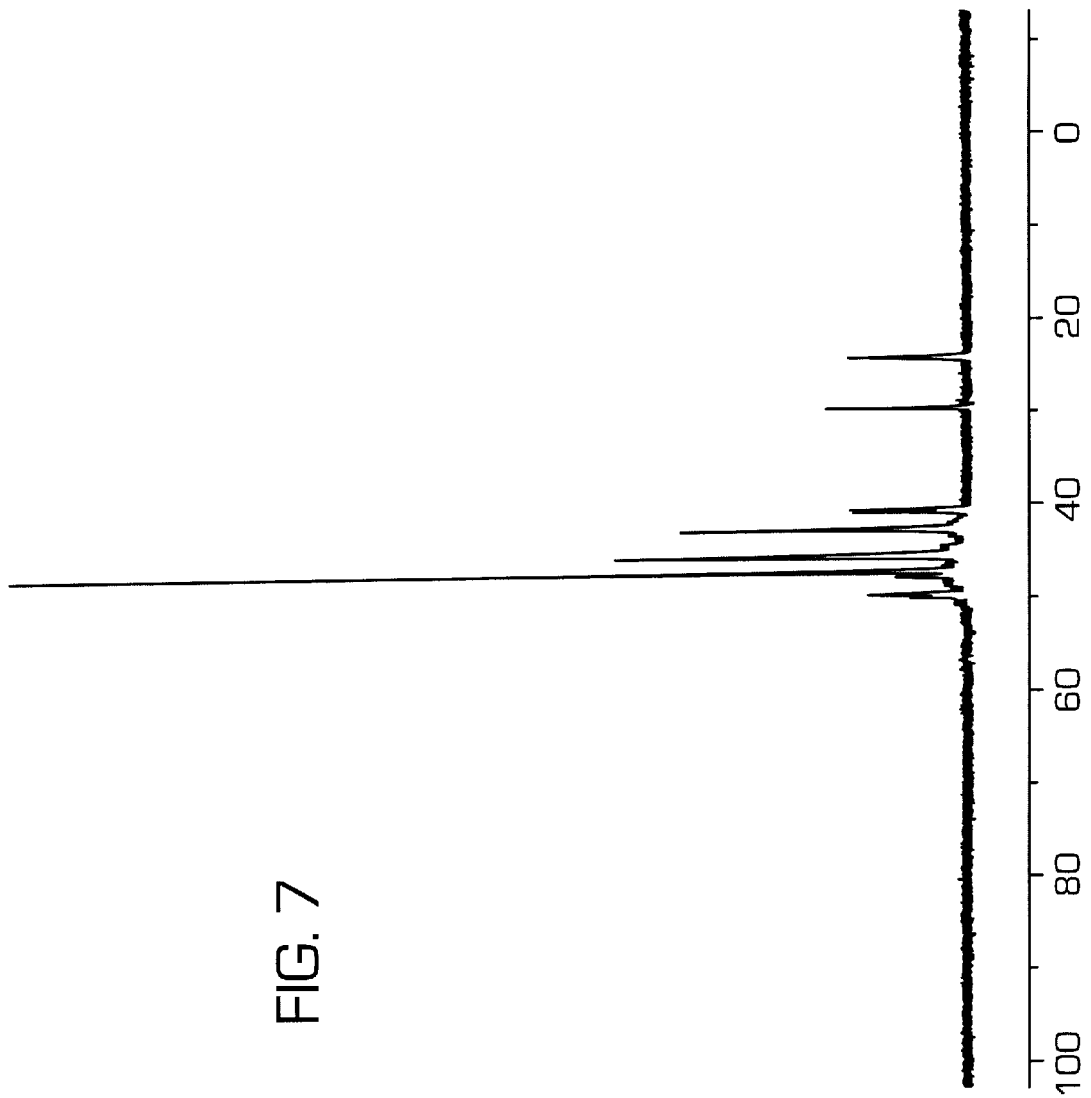
FIG. 7 is a view showing the $^{31}$P NMR spectrum of a ruthenium-iodo-optically active phosphine complex mixture obtained in Example 57.

From FIG. 7, the ratio of the amount of [RuI((S)-SEGPHOS)(PhCN)$_3$](ONf) (at 42.1 and 44.0 ppm) to the total amount of [Ru((S)-SEGPHOS)(PhCN)$_4$](ONf)$_2$, [Ru((S)-SEGPHOS)(PhCN)$_4$](I)$_2$ and [Ru((S)-SEGPHOS)(PhCN)$_4$](I)(ONf) (at 46.6 ppm) was 16:84.

EXAMPLE 60

Production of a Complex Mixture of [Ru((S)-DM-SEGPHOS)(CH$_3$CN)$_4$](OhepDf)$_2$, [Ru((S)-DM-SEGPHOS)(CH$_3$CN)$_4$](I)$_2$, [Ru((S)-DM-SEGPHOS)(CH$_3$CN)$_4$](I)(OhepDf) and [RuI((S)-DM-SEGPHOS)(CH$_3$CN)$_3$](OhepDf)

A 100 ml eggplant-shape flask was, after the air in the flask was replaced by nitrogen, charged with 166.0 mg (0.170 mmol) of [RuI$_2$(p-cymene)]$_2$, 250.0 mg (0.344 mmol) of (S)-DM-SEGPHOS, 93.3 mg (0.172 mmol) of KOhepDf and 8 ml of deaerated acetonitrile, and the mixture was stirred at 80° C. for 16 hours. The mixture was cooled to 40° C., and acetonitrile was withdrawn under reduced pressure. Then, in the nitrogen atmosphere, 10 ml of methylene chloride and 15 ml of deaerated water were added to the resulting mixture, followed by stirring for 10 minutes. The methylene chloride layer was extracted into a sampling syringe and washed with 15 ml of deaerated water, followed by distilling methylene chloride under reduced pressure. The resulting complex was then dried at 30° C. under reduced pressure for 4 hours, to obtain 400 mg (yield: 74.6%) of the titled compound.

$^{31}$P NMR; δ45.8, 44.3, 41.9 ppm

Figure 8:
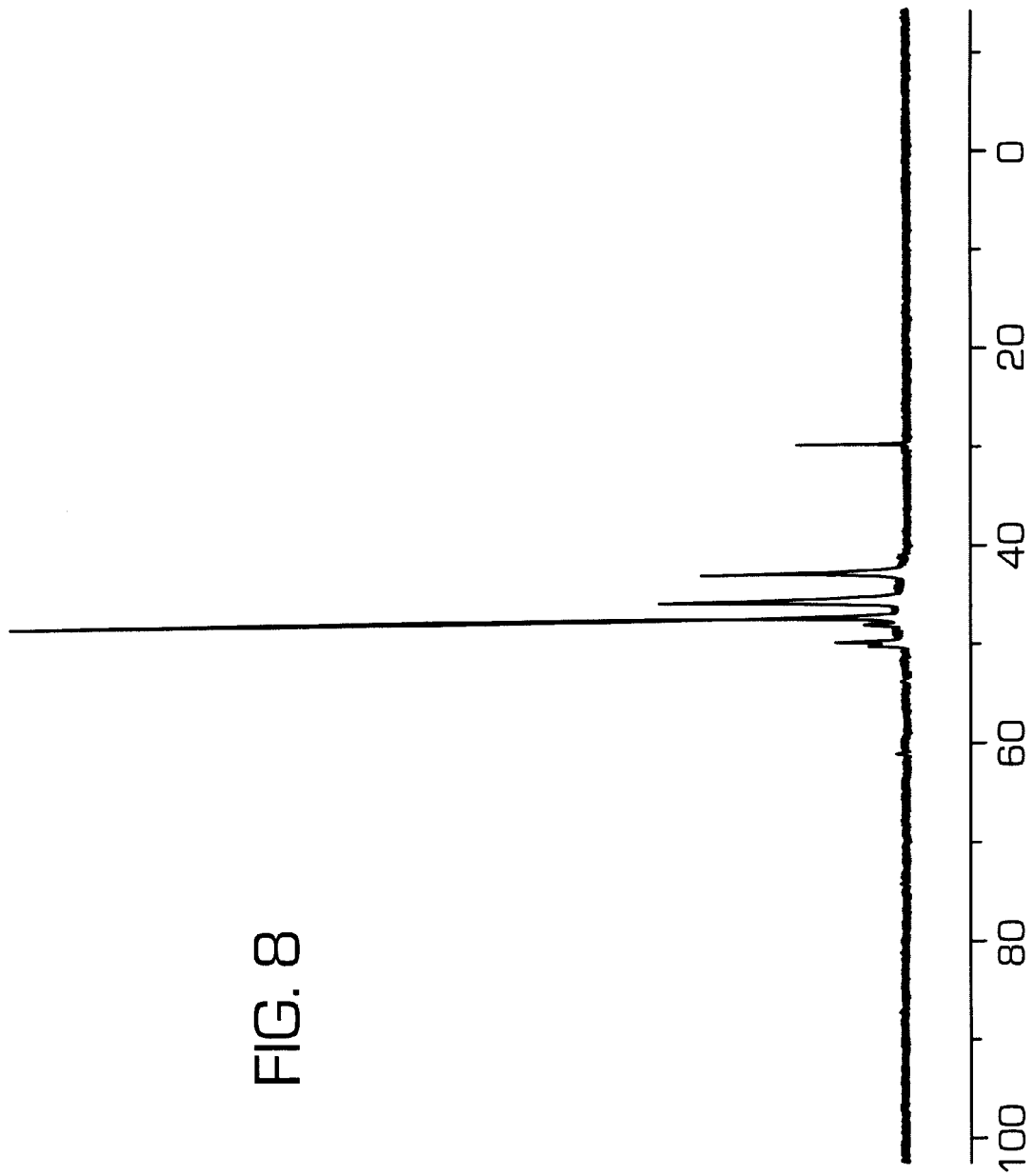
FIG. 8 view showing the $^{31}$P NMR spectrum of a ruthenium-iodo-optically active phosphine complex mixture obtained in Example 58.
Figure 9:
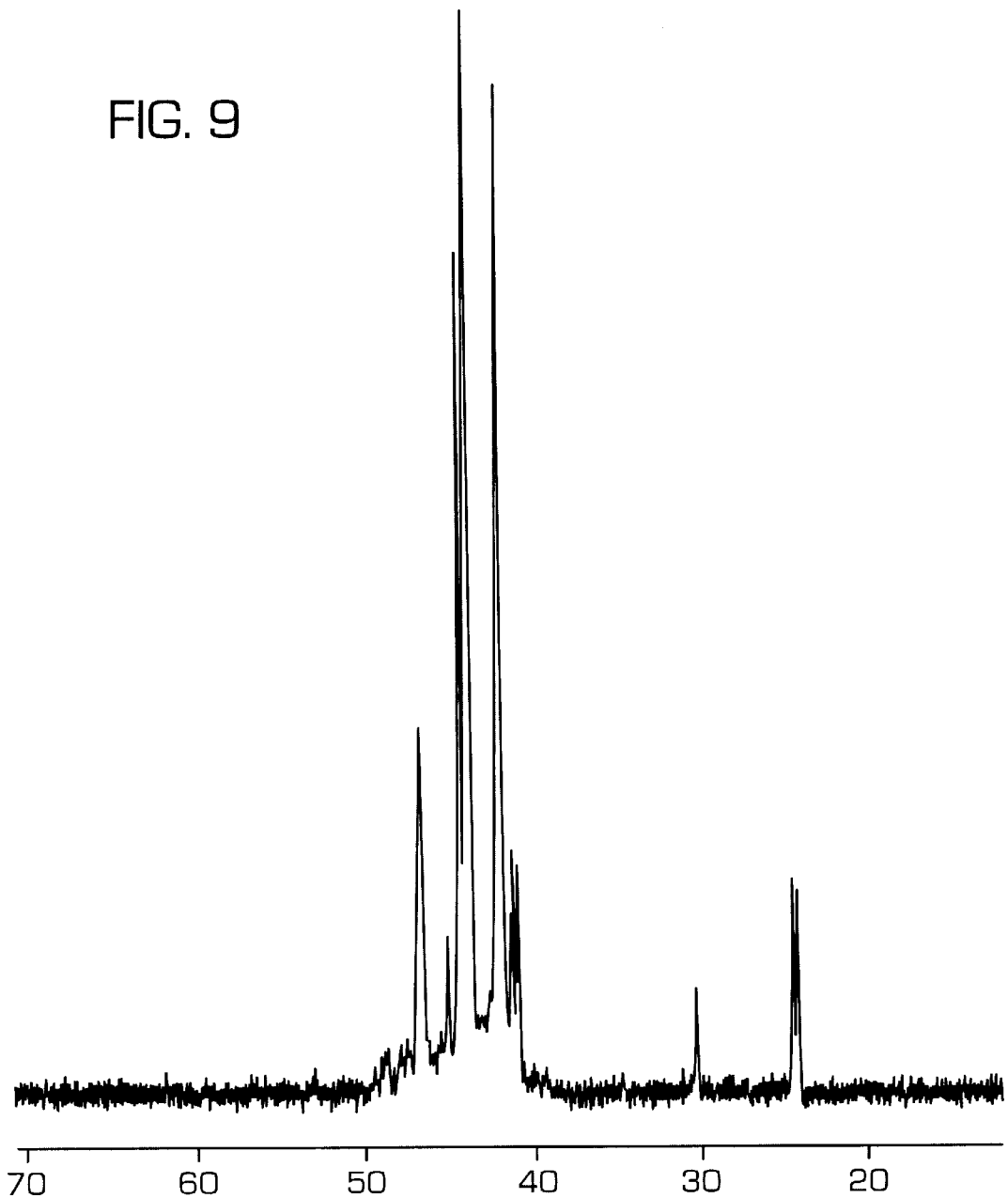
FIG. 9 is a view showing the $^{31}$P NMR spectrum of a ruthenium-iodo-optically active phosphine complex mixture obtained in Example 59.
Figure 10:
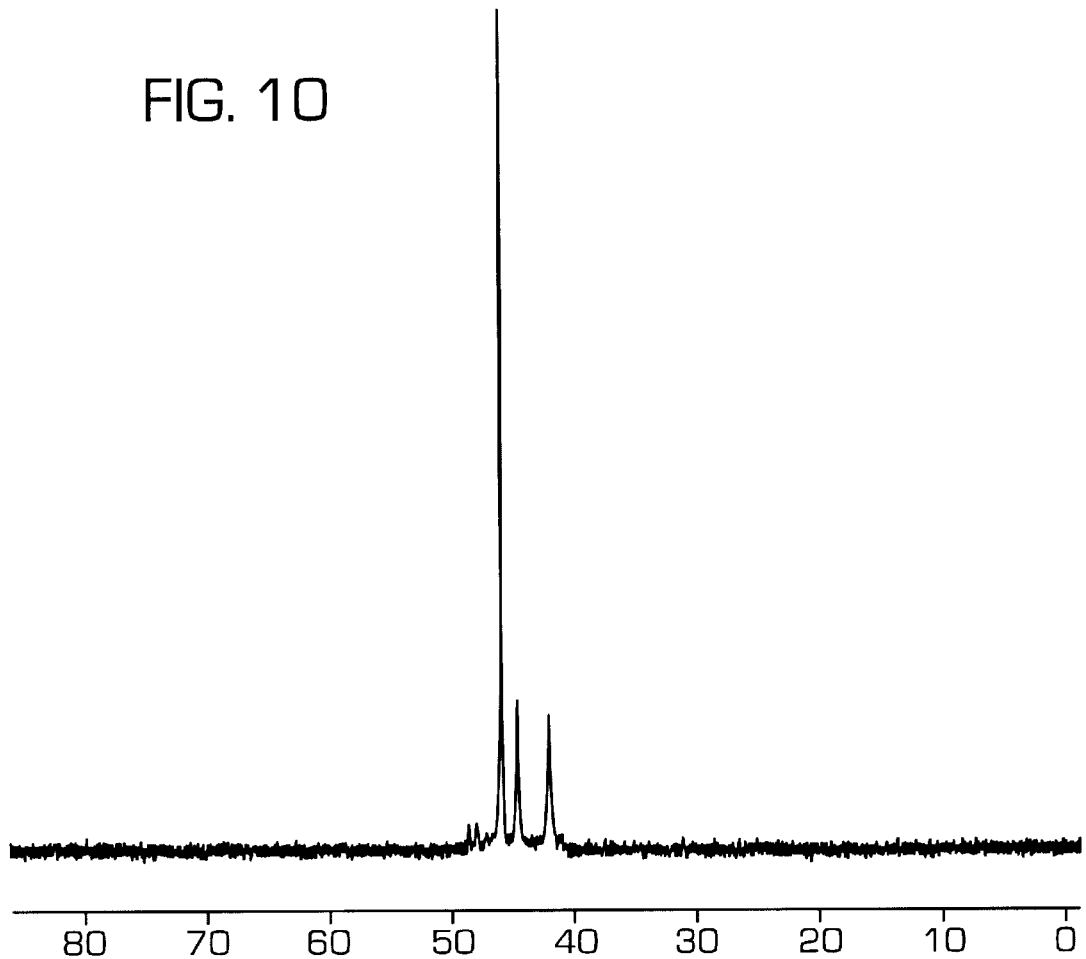
FIG. 10 is a view showing the $^{31}$P NMR spectrum of a ruthenium-iodo-optically active phosphine complex mixture obtained in Example 60.

From FIG. 8, the ratio of the amount of [RuI((S)-DM-SEGPHOS)(CH3CN)3](OhepDf) (at 44.3 and 41.9 ppm) to the total amount of [Ru((S)-DM-SEGPHOS)(CH$_3$CN)$_4$](OhepDf)$_2$, [Ru((S)-DM-SEGPHOS)(CH$_3$CN)$_4$](I)$_2$ and [Ru((S)-DM-SEGPHOS)(CH$_3$CN)$_4$](I)(OhepDf) (at 45.8 ppm) was 49: 51.

EXAMPLE 61

Production of (R)-4-methyl-2-oxetanone

A stainless autoclave with a volume of 500 ml was charged with 16.7 mg (0.0132 mmol) of the mixture catalyst obtained in Example 1, 20.02 g (238.1 mmol) of 4-methylene-2-oxetanone, 80 ml of acetone and 0.45 ml of deaerated water under nitrogen, and the mixture was stirred at a reaction temperature of 60° C. under a hydrogen pressure of 40 kg/cm$^2$ for 16 hours. The resulting reaction solution was distilled using a Claisen tube distiller, to obtain 18.6 g of a fraction having a boiling point of 71–73° C./29 mmHg (3866 Pa). The conversion rate (yield) of this reaction was 93.0% and the turn-over number measured to evaluate the catalytic activity was 16771.

A gas chromatography analysis of the resultant product, by comparison to a standard material, showed that the product obtained was 4-methyl-2-oxetanone. In order to determine the absolute configuration of the resulting product, the product was subjected to a gas chromatography (GC) analysis using an optically active column (Chiraldex G-TA 30 m, manufactured by ASTEC). The result of the analysis showed that the resultant product was an (R) isomer and the optical purity was 91.6% e.e.

EXAMPLE 62

Production of (R)-4-methyl-2-oxetanone

The same procedures as in Example 61 were carried out, except that 21.1 mg (0.0190 mmol) of the complex mixture catalyst obtained in Example 57 and 20.72 g (246.5 mmol) of 4-methylene-2-oxetanone were used, to obtain 18.5 g of the titled compound. The conversion rate (yield) of this reaction was 89.2% and the turn-over number measured to evaluate the catalytic activity was 11594. The measurement of the absolute configuration showed that the resulting product was an (R) isomer and the optical purity was 91.9% e.e.

EXAMPLE 63

Production of (R)-4-methyl-2-oxetanone

The same procedures as in Example 61 were carried out, except that 17.4 mg (0.0119 mmol) of the complex mixture catalyst obtained in Example 58 and 21.01 g (249.9 mmol) of 4-methylene-2-oxetanone were used, to obtain 18.1 g of the titled compound. The conversion rate (yield) of this reaction was 86.2% and the turn-over number measured to evaluate the catalytic activity was 18110. The measurement of the absolute configuration showed that the resulting product was an (R) isomer and the optical purity was 91.9% e.e.

EXAMPLE 64

Production of (R)-4-methyl-2-oxetanone

The same procedures as in Example 61 were carried out, except that 22.9 mg (0.0159 mmol) of the complex mixture catalyst obtained in Example 59 and 20.68 g (246.0 mmol) of 4-methylene-2-oxetanone were used, to obtain 13.5 g of the titled compound. The conversion rate (yield) of this reaction was 65.2% and the turn-over number measured to evaluate the catalytic activity was 10092. The measurement of the absolute configuration showed that the resulting product was an (R) isomer and the optical purity was 91.2%e.e.

EXAMPLE 65

Production of (R)-4-methyl-2-oxetanone

The same procedures as in Example 61 were carried out, except that 20.9 mg (0.0166 mmol) of the complex mixture catalyst obtained in Example 55 and 20.88 g (248.4 mmol) of 4-methylene-2-oxetanone were used and the reaction was performed under a hydrogen pressure of 20 kg/cm$^2$, to obtain 11.8 g of the titled compound. The conversion rate (yield) of this reaction was 56.7% and the turn-over number measured to evaluate the catalytic activity was 8508. The measurement of the absolute configuration showed that the resulting product was an (R) isomer and the optical purity was 93.0% e.e.

EXAMPLE 66

Production of (R)-4-methyl-2-oxetanone

The same procedures as in Example 61 were carried out, except that 18.9 mg (0.0120 mmol) of the complex mixture catalyst obtained in Example 60, and 21.1 g (252 mmol) of 4-methylene-2-oxetanone were used, to obtain 14.9 g of the titled compound. The conversion rate (yield) of this reaction was 68.9% and the turn-over number measured to evaluate the catalytic activity was 14459. The measurement of the absolute configuration showed that the resulting product was an (R) isomer and the optical purity was 89.6% e.e.

Comparative Example 4

Production of (R)-4-methyl-2-oxetanone

The ruthenium-iodo-optically active phosphine complex was prepared as described in JP-A No. H10-139791. Using this phosphine complex as catalyst, optically active 4-methyl-2-oxetanone was produced. Specifically, an 80 ml Schlenk's tube, in which the air was replaced by nitrogen in advance, was charged with 1.0 g (1.02 mmol) of [RuI$_2$(p-cymene)]$_2$, 1.41 g (2.07 mmol) of (S)—T-BINAP and 40 ml of methanol, and the mixture was stirred at 55° C. for 16 hours. After the reaction was completed, methanol was distilled under reduced pressure, to obtain 2.35 g of RuI$_2$\{(S)—T-BINAP\}.

82.0 mg (0.0793 mmol) of the resulting complex RuI$_2$\{(S)—T-BINAP\}, 21.3 g (253 mmol) of 4-methylene-2-oxetanone, 80 ml of tetrahydrofuran and 0.45 ml of deaerated water were mixed, and the mixture was reacted at a temperature of 60° C. under a hydrogen pressure of 40 kg/cm$^2$, to obtain 13.8 g of the titled compound. The conversion rate (yield) of this reaction was 65.0%, and the turn-over number measured to evaluate the catalytic activity was 2073. The measurement of the absolute configuration showed that the resulting product was an (R) isomer and the optical purity was 94.0% e.e.

Comparative Example 5

Production of (R)-4-methyl-2-oxetanone 52.3 mg (0.0476 mmol) of the complex [RuI(p-cymene) ((S)-SEGPHOS)]I were prepared according to the method described in JP-A No. H5-111639. To this, 22.1 g (263 mmol) of 4-methylene-2-oxetanone, 80 ml of acetone and 0.45 ml of deaerated water were mixed, and the mixture was reacted at a temperature of 60° C. under a hydrogen pressure of 40 kg/cm$^2$, to obtain 5.41 g of the titled compound. The conversion rate (yield) of this reaction was 23.9%, and the turn-over number measured to evaluate the catalytic activity was 1318. The measurement of the absolute configuration showed that the resulting product was an (R) isomer and the optical purity was 91.8% e.e.

Comparative Example 6

Production of (R)-4-methyl-2-oxetanone 52.4 mg (0.0476 mmol) of the complex [RuI((S)-BINAP) (CH$_3$CN)$_3$]$^+$I$^-$ were prepared according to the method described in J. Chem. Soc. Dalton Trans., pp. 2099–2107 (1992). To this, 20.8 g (247 mmol) of 4-methylene-2-oxetanone, 80 ml of acetone and 0.45 ml of deaerated water were mixed, and the mixture was reacted at a temperature of 60° C. under a hydrogen pressure of 40 kg/cm$^2$, to obtain 9.31 g of the titled compound. The conversion rate (yield) of this reaction was 43.8%, and the turn-over number measured to evaluate the catalytic activity was 2278. The measurement of the absolute configuration showed that the resulting product was an (R) isomer and the optical purity was 93.5% e.e.

Comparative Example 7

Production of [Ru((S)-SEGPHOS)(CH$_3$CN)$_4$] (OhepDf)$_2$

A 100 ml eggplant-shape flask was, after the air in the flask was replaced by nitrogen, charged with 12.0 mg (0.123 mmol) of [RuI$_2$(p-cymene)]$_2$, 15.2 mg (0.248 mmol) of (S)-SEGPHOS, 277 mg (0.515 mmol) of KOhepDf and 10 ml of deaerated acetonitrile, and the mixture was stirred at 80° C. for 16 hours. The mixture was cooled to 40° C., and acetonitrile was withdrawn under reduced pressure. Then, in the nitrogen atmosphere, 10 ml of methylene chloride and 15 ml of deaerated water were added to the resulting mixture, followed by stirring for 10 minutes. The methylene chloride layer was extracted into a sampling syringe and washed with 15 ml of deaerated water, followed by distilling methylene chloride under reduced pressure. The resulting complex was then dried at 30° C. under reduced pressure for 4 hours, to obtain 360 mg (yield: 78.3%) of the titled compound.

$^{31}$P NMR; δ47.4 ppm

Comparative Example 8

Production of (R)-4-methyl-2-oxetanone

The same procedures as in Example 61 were carried out, except that 22.3 mg (0.119 mmol) of [Ru((S)-SEGPHOS)(CH$_3$CN)$_4$](OhepDf)$_2$ prepared in Comparative Example 7, and 21.6 g (256 mmol) of 4-methylene-2-oxetanone were used, to obtain 8.53 g of the titled compound. The conversion rate (yield) of this reaction was 38.7%, and the turn-over number measured to evaluate the catalytic activity was 8332. The measurement of the absolute configuration showed that the resulting product was an (R) isomer and the optical purity was 85.1% e.e.

The catalytic activity (turn-over number) and the configuration and optical purity (% e.e.) of 4-methyl-2-oxetanone in Examples 61–66 and Comparative Examples 4 to 6 and and 8 are shown collectively in Table 2.

TABLE 2

| | Catalytic activity (Turn-over number) | Configuration | Optical purity (% e.e.) |
| --- | --- | --- | --- |
| Example 61 | 16771 | R-isomer | 91.6 |
| Example 62 | 11594 | R-isomer | 91.9 |
| Example 63 | 18110 | R-isomer | 91.9 |
| Example 64 | 10092 | R-isomer | 91.2 |
| Example 65 | 8508 | R-isomer | 93.0 |
| Example 66 | 14459 | R-isomer | 89.6 |
| Comparative Example 4 | 2073 | R-isomer | 94.0 |
| Comparative Example 5 | 1318 | R-isomer | 91.8 |
| Comparative Example 6 | 2278 | R-isomer | 93.5 |
| Comparative Example 7 | 8332 | R-isomer | 85.1 |

What is claimed:

1. A ruthenium-iodo-optically active bidentate phosphine complex of the formula (1):

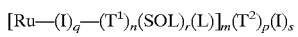

(1)

wherein T¹ represents a carboxylic acid anion, SOL represents a polar solvent, L represents an optically active bidentate phosphine ligand, T² represents an anion different from halogen atom anions and carboxylic acid anions, n denotes 0 or 1, r denotes 0, 3 or 4, m denotes 1 or 2, q denotes 0 or 1, or where m is 2, 1 or 1.5, p denotes 0 or 1, and s denotes 0, 1 or 2.

2. A ruthenium-iodo-optically active bidentate phosphine complex according to claim 1, wherein r and s are each 0, and q is 1, or where m is 2, 1 or 1.5; said ruthenium-iodo-optically active bidentate phosphine complex having the formula (1a):

3. A ruthenium-iodo-optically active bidentate phosphine complex according to claim 1, wherein L is of the formula (2):

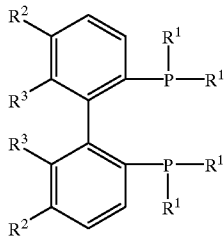

wherein R¹ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms; and R² and R³ which may be the same or different, each represent a hydrogen atom, a halogen atom, a lower alkyl group having 1 to 4 carbon atoms or a lower alkoxy group having 1 to 4 carbon atoms; or R² and R³ may be combined to form a five-membered or six-membered ring.

4. A ruthenium-iodo-optically active bidentate phosphine complex according to claim 2, wherein L is of the formula (2):

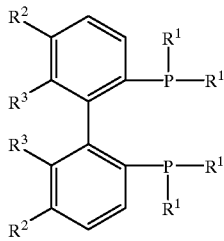

wherein R¹ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms; and R² and R³, which may be the same or different, each represent a hydrogen atom, a halogen atom, a lower alkyl group having 1 to 4 carbon atoms or a lower alkoxy group having 1 to 4 carbon atoms; or R² and R³ may be combined to form a five-membered or six-membered ring.

5. A method of preparing the ruthenium-iodo-optically active bidentate phosphine complex according to claim 2, said method being characterized by reacting, in a polar solvent different from nitrile-type solvents, a ruthenium-iodo-optically active phosphine complex of the formula (3):

wherein arene represents a hydrocarbon having a benzene ring and L represents an optically active bidentate phosphine ligand, either with (i) a carboxylate of the formula (4):

wherein Z¹ represents an alkali metal or an alkali earth metal, a denotes 1 when Z¹ is an alkali metal, or 2 when Z¹ is an alkali earth metal, and T¹ has the same meaning as that defined in the formula (I); or with (ii) a salt of the formula (5):

wherein Z² represents a mono-or di-cation of an alkali metal, an alkali earth metal, an ammonium or the like, T² represents a mono- or di-anion different from halogen atom anions and carboxylic acid anions, in which when Z² is a mono-cation and T² is a mono-anion, b and c are each 1; when Z² is a mono-cation and T² is a di-anion, b and c denote 2 and 1, respectively; when Z² is a di-cation and T² is a di-anion, b and c are each 1, and when Z² is a di-cation and T² is a mono-anion, b and c denote 1 and 2, respectively.

6. A method of preparing the ruthenium-iodo-optically active bidentate phosphine complex according to claim 4, said method being characterized by reacting, in a polar solvent different from nitrile-type solvents, a ruthenium-iodo-optically active phosphine complex of the formula (3):

wherein arene represents a hydrocarbon having a benzene ring and L represents an optically active bidentate phosphine ligand defined in claim 4, either with (i) a carboxylate of the formula (4):

wherein Z¹ represents an alkali metal or an alkali earth metal, a denotes 1 when Z¹ is an alkali metal, or 2 when Z¹ is an alkali earth metal, and T¹ has the same meaning as that defined in the formula (I); or with (ii) a salt of the formula (5):

wherein Z² represents a mono-or di-cation of an alkali metal, an alkali earth metal, an ammonium or the like, T² represents a mono- or di-anion different from halogen atom anions and carboxylic acid anions, in which when Z² is a mono-cation and T² is a mono-anion, b and c are each 1; when Z² is a mono-cation and T² is a di-anion, b and c denote 2 and 1, respectively; when Z² is a di-cation and T² is a di-anion, b and c are each 1, and when Z² is a di-cation and T² is a mono-anion, b and c denote 1 and 2, respectively.

7. A method of preparing the ruthenium-iodo-optically active bidentate phosphine complex according to claim 2, said method being characterized by reacting, in a polar solvent different from nitrile-type solvents, a compound of formula (6):

   [RuI₂(arene)]₂   (6)

wherein arene represents a hydrocarbon having a benzene ring, with an optically active bidentate phosphine ligand L as defined in claim 2, and either with (i) a carboxylate of the formula (4):

   (T¹)ₐZ¹   (4)

wherein Z¹, a and T¹ have the same meaning as those defined in claim 4; or with (ii) a salt of the formula (5):

   Z²_b(T²)_c   (5)

wherein Z², b, T² and c have the same meaning as those defined in claim 2.

8. A method of preparing the ruthenium-iodo-optically active bidentate phosphine complex according to claim 4, said method being characterized by reacting, in a polar solvent different from nitrile-type solvents, a compound of formula (6):

   [RuI₂(arene)]₂   (6)

wherein arene represents a hydrocarbon having a benzene ring, with an optically active bidentate phosphine ligand L as defined in the formula (1a), and either with (i) a carboxylate of the formula (4):

   (T¹)ₐZ¹   (4)

wherein Z¹, a and T¹ have the same meaning as those defined in claim 4; or with (ii) a salt of the formula (5):

   Z²_b(T²)_c   (5)

wherein Z², b, T² and c have the same meaning as those defined in claim 4.

9. A ruthenium-iodo-optically active bidentate phosphine complex according to claim 2, wherein said optically active bidentate phosphine ligand L is a compound selected from the group consisting of an optically active tertiary phosphine (R¹-BINAP), in which R² and R³ in said formula (2) are combined with each other to form a six-membered benzene ring and which is represented by the formula (7):

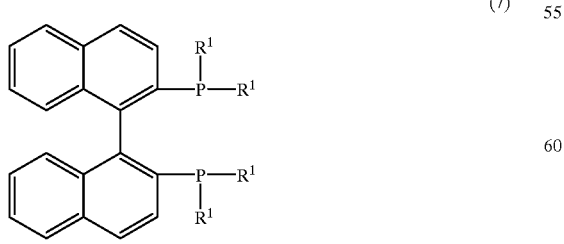

(7)

wherein R¹ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms;

an optically active tertiary phosphine (H⁸—R¹-BINAP), in which R² and R³ in said formula (2) are combined with each other to form a six-membered cyclohexyl ring and which is represented by the formula (8):

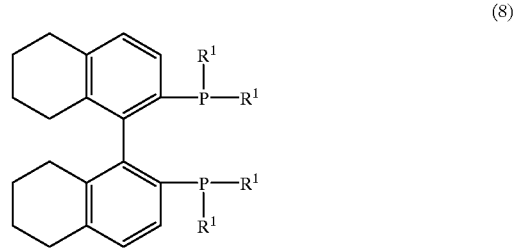

(8)

wherein R¹ is defined as indicated above in said formula (7), and;

an optically active tertiary phosphine (R¹-SEGPHOS), in which R² and R³ in the formula (II) are combined with each other to form a five-membered 1,3-dioxolan ring and which is represented by the formula (9):

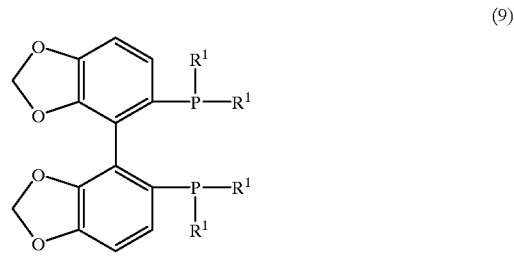

(9)

wherein R¹ is defined as indicated above in said formula (7).

10. A ruthenium-iodo-optically active bidentate phosphine complex according to claim 4, wherein said optically active bidentate phosphine ligand (L) is a compound selected from the group consisting of an optically active tertiary phosphine (R¹-BINAP), in which R² and R³ in said formula (2) are combined with each other to form a six-membered benzene ring and which is represented by the formula (7):

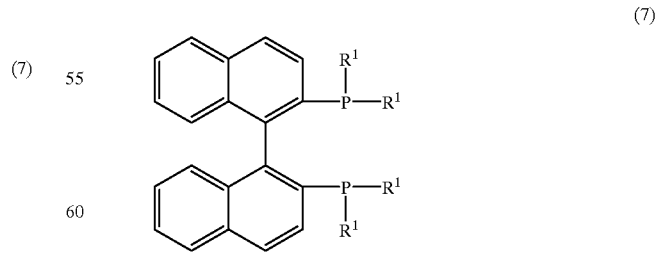

(7)

wherein R¹ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms;

an optically active tertiary phosphine ($H^8$—$R^1$-BINAP), in which $R^2$ and $R^3$ in said formula 2 are combined with each other to form a six-membered cyclohexyl ring and which is represented by the formula (8):

(8)

wherein $R^1$ is defined as indicated above in said formula (7), and;

an optically active tertiary phosphine ($R^1$-SEGPHOS), in which $R^2$ and $R^3$ in the formula (2) are combined with each other to form a five-membered 1,3-dioxolan ring and which is represented by the formula (9):

(9)

wherein $R^1$ is defined as indicated above in said formula (7).

11. A method of preparing the ruthenium-iodo-optically active bidentate phosphine complex according to claim 5, wherein L in the formula (3) represents $R^1$-BINAP as shown in the formula (10):

[RuI(arene)($R^1$-BINAP)]I          (10)

$R^1$-BINAP being defined in the formula (VII).

12. A method of preparing the ruthenium-iodo-optically active bidentate phosphine complex according to claim 6, wherein L in the formula (3) represents $R^1$-BINAP as shown in the formula (10):

[RuI(arene)(R1-BINAP)]I          (10)

$R^1$-BINAP being defined in the formula (7).

13. A method of preparing the ruthenium-iodo-optically active bidentate phosphine complex according to claim 7, wherein L in the formula (1) represents $R^1$-BINAP as defined in the formula (7).

14. A method of preparing the ruthenium-iodo-optically active bidentate phosphine complex according to claim 8, wherein L in the formula (1) represents $R^1$-BINAP as defined in the formula (7).

15. A method of preparing the ruthenium-iodo-optically active bidentate phosphine complex according to claim 5, wherein said ruthenium-optically active phosphine complex of the formula (3), in which L represents $R^1$-SEGPHOS as shown in the formula (11):

[RuI(arene)($R^1$-SEGPHOS)]I          (11)

$R^1$-SEGPHOS being defined in the formula (9); is reacted with said salt of the formula (5).

16. A method of preparing the ruthenium-iodo-optically active bidentate phosphine complex according to claim 6, wherein said ruthenium-optically active phosphine complex of the formula (3), in which L represents $R^1$-SEGPHOS as shown in the formula (XI):

[RuI(arene)($R^1$-SEGPHOS)]I          (11)

$R^1$-SEGPHOS being defined in the formula (9); is reacted with said salt of the formula (5).

17. A method of preparing the ruthenium-iodo-optically active bidentate phosphine complex according to claim 7, wherein L in the formula (1) represents $R^1$-SEGPHOS as defined in the formula (9), and said ruthenium complex and $R^1$-SEGPHOS are reacted with said salt of the formula (5).

18. A method of preparing the ruthenium-iodo-optically active bidentate phosphine complex according to claim 8, wherein L in the formula (1) represents $R^1$-SEGPHOS as defined in the formula (9), and said ruthenium complex and $R^1$-SEGPHOS are reacted with said salt of the formula (5).

19. A ruthenium-iodo-optically active bidentate phosphine complex of formula (1)

[Ru—(I)$_q$—(T$^1$)$_n$(SOL)$_r$(L)]$_m$(T$^2$)$_p$(I)$_s$          (1)

wherein; $T^1$ represents a carboxylic acid anion; SOL represents a polar solvent; L represents $R^1$-SEGPHOS as defined in the formula (9); $T^2$ represents an anion different from halogen atom anions and carboxylic acid anions; n denotes 0; m denotes 1; p denotes 1; q denotes 0 or 1; r denotes 3 or 4; and s denotes 0, 1 or 2.

20. The ruthenium-iodo-optically active bidentate phosphine complex according to claim 19, comprising three different complexes of formulae (12), (13) and (14):

[Ru($R^1$-SEGPHOS)(SOL)$_4$]I$_2$          (12)

[Ru($R^1$-SEGPHOS)(SOL)$_4$]I(anion)          (13)

[RuI($R^1$-SEGPHOS)(SOL)$_3$](anion)          (14)

wherein $R^1$-SEGPHOS represents an optically active tertiary phosphine of the formula (9), SOL represents a nitrile-type polar solvent, and $T_2$ designated as anion represents a perfluoroalkylsulfonyl anion.

21. A method of preparing a ruthenium-iodo-optically active bidentate phosphine complex according to claim 20, wherein a ruthenium-optically active tertiary phosphine complex of the formula (11):

[RuI(arene)($R^1$-SEGPHOS)]I          (11)

wherein arene represents a hydrocarbon having a benzene ring and $R^1$-SEGPHOS has the same meaning as defined for the formula (9); is reacted with a perfluoroalkylsulfonate of the formula (5), in a nitrile-type polar solvent.

22. A method of preparing a ruthenium-iodo-optically active bidentate phosphine complex according to claim 20, wherein a ruthenium complex of the formula (6), an optically active phosphine represented by $R^1$-SEGPHOS of the formula (9), and a perfluoroalkylsulfonate of the formula (5) are reacted in a nitrile-type polar solvent.

23. A process for preparing an optically active 4-methyl-2-oxetanone by asymmetrically hydrogenating 4-methylene-2-oxetanone in the presence of a ruthenium-iodo-optically active bidentate phosphine complex of the formula (1):

[Ru—(I)$_q$—(T$^1$)$_n$(SOL)$_r$(L)]$_m$(T$^2$)$_p$(I)$_s$ (1)

wherein T$^1$ represents a carboxylic acid anion, SOL represents a polar solvent, L represents an optically active bidentate phosphine ligand, T$^2$ represents an anion different from halogen atom anions and carboxylic acid anions, n denotes 0 or 1, r denotes 0,3 or 4, m denotes 1 or 2, q denotes 0 or 1, or where m is 2, 1 or 1.5, p denotes 0 or 1, and s denotes 0, 1 or 2.

24. A process for preparing an optically active 4-methyl-2-oxetanone by asymmetrically hydrogenating 4-methylene-2-oxetanone in the presence of a ruthenium-iodo-optically active bidentate phosphine complex of the formula (1):

[Ru—(I)$_q$—(T$^1$)$_n$(SOL)$_r$(L)]$_m$(T$^2$)$_p$(I)$_s$ (1)

wherein T$^1$ represents a carboxylic acid anion, SOL represents a polar solvent, L represents an optically active bidentate phosphine ligand, T$^2$ represents an anion different from halogen atom anions and carboxylic acid anions, n denotes 0 or 1, r denotes 0, m denotes 1 or 2, q denotes 1, or where m is 2, 1 or 1.5, p denotes 0 or 1, and s denotes 0, and wherein said optically active bidentate phosphine ligand L is a compound selected from the group consisting of an optically active tertiary phosphine (R$^1$-BINAP), in which R$^2$ and R$^3$ in said formula (2) are combined with each other to form a six-membered benzene ring and which is represented by the formula (7):

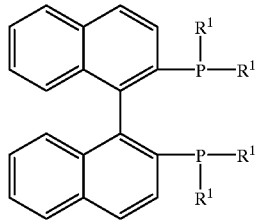

(7)

wherein R$^1$ represents an aryl group which may have a substituent selected from the group consisting of a lower alkyl group having 1 to 4 carbon atoms, a lower alkoxy group having 1 to 4 carbon atoms, a lower alkylamino group having 1 to 4 carbon atoms and a halogen atom, or a cycloalkyl group having 3 to 8 carbon atoms;

an optically active tertiary phosphine (H$^8$—R$^1$-BINAP), in which R$^2$ and R$^3$ in said formula (2) are combined with each other to form a six-membered cyclohexyl ring and which is represented by the formula (8):

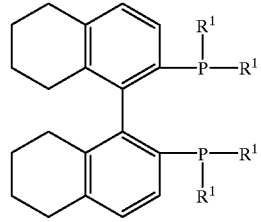

(8)

wherein R$^1$ is defined as indicated above in said formula (7), and;

an optically active tertiary phosphine (R$^1$-SEGPHOS), in which R$^2$ and R$^3$ in the formula (2) are combined with each other to form a five-membered 1,3-dioxolan ring and which is represented by the formula (9):

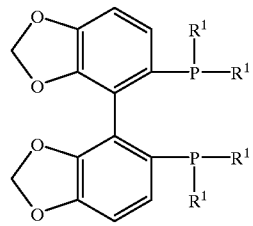

(9)

wherein R$^1$ is defined as indicated above in said formula (7).

25. A process for preparing an optically active 4-methyl-2-oxetanone by asymmetrically hydrogenating 4-methylene-2-oxetanone in the presence of a ruthenium-iodo-optically active bidentate phosphine complex comprising three different complexes of formulae (12), (13) and (14):

[Ru(R$^1$-SEGPHOS)(SOL)$_4$]I$_2$ (12)

[Ru(R$^1$-SEGPHOS)(SOL)$_4$]I(anion) (13)

[RuI(R$^1$-SEGPHOS)(SOL)$_3$](anion) (14)

wherein R$^1$-SEGPHOS represents an optically active tertiary phosphine of the formula (9), SOL represents a nitrile-type polar solvent, and T$^2$ designated as anion represents a perfluoroalkylsulfonyl anion.

* * * * *